United States Patent
Andre et al.

(10) Patent No.: US 10,494,433 B2
(45) Date of Patent: Dec. 3, 2019

(54) COMBINATION OF ANTI-KIR AND ANTI-CS1 ANTIBODIES TO TREAT MULTIPLE MYELOMA

(71) Applicants: BRISTOL-MYERS SQUIBB COMPANY, Princeton, NJ (US); Innate Pharma, Marseilles (FR)

(72) Inventors: Pascale Andre, Marseilles (FR); Mathieu Blery, Marseilles (FR); Cecile Bonnafous, Marseilles (FR); Ashok K. Gupta, Plainsboro, NJ (US); Luisa M. Salter-Cid, Princeton Junction, NJ (US); Michael Darron Robbins, Hillsborough, NJ (US)

(73) Assignees: BRISTOL-MYERS SQUIBB COMPANY, Princeton, NJ (US); Innate Pharma, Marseilles (FR)

( * ) Notice: Subject to any disclaimer, the term of this patent is extended or adjusted under 35 U.S.C. 154(b) by 0 days.

(21) Appl. No.: 15/032,919

(22) PCT Filed: Nov. 5, 2014

(86) PCT No.: PCT/US2014/064153
§ 371 (c)(1),
(2) Date: Apr. 28, 2016

(87) PCT Pub. No.: WO2015/069785
PCT Pub. Date: May 14, 2015

(65) Prior Publication Data
US 2016/0257750 A1 Sep. 8, 2016

Related U.S. Application Data

(60) Provisional application No. 61/900,775, filed on Nov. 6, 2013.

(51) Int. Cl.
*C07K 16/28* (2006.01)
*A61K 39/395* (2006.01)
*A61K 39/00* (2006.01)

(52) U.S. Cl.
CPC ...... *C07K 16/2803* (2013.01); *A61K 39/3955* (2013.01); *A61K 2039/507* (2013.01); *A61K 2039/54* (2013.01); *A61K 2039/545* (2013.01); *C07K 2317/24* (2013.01); *C07K 2317/732* (2013.01); *C07K 2317/76* (2013.01); *C07K 2317/90* (2013.01)

(58) Field of Classification Search
CPC ............ C07K 16/2818; C07K 16/2803; A61K 39/395; A61K 39/3955; A61K 2039/507; A61K 2039/45
See application file for complete search history.

(56) References Cited

U.S. PATENT DOCUMENTS

| 7,041,499 B2 | 5/2006 | Mathew et al. |
| 7,709,610 B2 | 5/2010 | Williams et al. |
| 2010/0189723 A1* | 7/2010 | Wagtmann ....... A61K 39/39541 424/173.1 |

FOREIGN PATENT DOCUMENTS

| WO | 2004/100898 A2 | 11/2004 |
| WO | 2005/003168 A2 | 1/2005 |
| WO | 2005/009465 A1 | 2/2005 |
| WO | 2005/010238 A1 | 2/2005 |
| WO | 2006/003179 A2 | 1/2006 |
| WO | 2006/072626 A1 | 7/2006 |
| WO | 2006072625 A2 | 7/2006 |
| WO | 2007/042573 A2 | 4/2007 |
| WO | 2008/019376 A2 | 2/2008 |
| WO | 2008/019378 A1 | 2/2008 |
| WO | 2008/019379 A2 | 2/2008 |
| WO | 2008/084106 A1 | 7/2008 |
| WO | 2010/051391 A1 | 5/2010 |
| WO | 2010/065939 A1 | 6/2010 |
| WO | 2011/053321 A1 | 5/2011 |
| WO | 2011/053322 A1 | 5/2011 |
| WO | 2012/071411 A2 | 5/2012 |
| WO | 2012160448 A2 | 11/2012 |

OTHER PUBLICATIONS

Nijhof et al., Abstract #1865, Blood 2011: 118:1865.*
Zonder et al, Blood, 120:552-559 (Year: 2012).*
Lonial et al., J Clin Oncol, 30(16):1953-59 (Year: 2012).*
Henricks et al., Cancer Treatment Reviews 41:859-867 (Year: 2015).*
Anderson KC., "Lenalidomide and Thalidomide: Mechanisms of Action—Similarities and Differences," Seminars in Hematology, vol. 42:S3-S8 (2005).
Benson, D. et al., "IPH2101, a novel anti-inhibitory KIR antibody, and lenalidomide combine to enhance the natural killer cell versus multiple myeloma effect," BLOOD, 118(24): 6387-6391 (2011).
Bhat R, et al., "Fine-tuning of immune responses by SLAM-related receptors," Leukoc Biol., 79:417-424 (2006).
Boles, K. et al., "Molecular cloning of CS1, a novel human natural killer cell receptor belonging to the CD2 subset of the immunoglobulin superfamily," Immunogenetic, 52(3-4):302-307 (2001).
Bouchon , A. et al., "Cutting Edge: Activation of NK Cell-Mediated Cytotoxicity by a SAP-Independent Receptor of the CD2 Family," J. Immunol., 167:5517-5521 (2001).
Cambiaggi, A. et al., "Natural killer cell acceptance of H-2 mismatch bone marrow grafts in transgenic mice expressing HLA-Cw3 specific killer cell inhibitory receptor?(CD158b)," Proc. Natl. Acad. Sci., 94:8088-8092 (1997).

(Continued)

*Primary Examiner* — Jessica H Roark
(74) *Attorney, Agent, or Firm* — Nelson Mullins Riley & Scarborough LLP; Jane E. Remillard, Esq.; Jeanne M. DiGiorgio, Esq.

(57) ABSTRACT

Provided are methods for clinical treatment of multiple myeloma using an anti-KIR antibody in combination with an anti-CS 1 antibody.

14 Claims, 42 Drawing Sheets

Specification includes a Sequence Listing.

(56) References Cited

OTHER PUBLICATIONS

Campbell, K. et al., "Structure/function of human killer cell immunoglobulin-like receptors: lessons from polymorphisms, evolution, crystal structures and mutations," Immunology, 132(3):315-325 (2011).
Cartron, G., et al.,"Therapeutic activity of humanized anti-CD20 monoclonal antibody and polymorphism in IgG Fc receptor FcgammaRIIIa gene.," Blood, 99(3): 754-758 (2002).
Congy-Jolivet, N., et al., "Fc gamma RIIIa expression is not increased on natural killer cells expressing the Fc gamma RIIIa-158V allotype," Cancer Res., 68(4): 976-980 (2008).
Crane E. et al., "Immunomodulatory Drugs," Cancer Investigation, 23(7):625-634 (2005).
Current, J., "A Linear Equation for Estimating the Body Surface Area in Infants and Children," Internet Journal of Anesthesiology, 2(2): 4 pages (1998).
Dall'ozzo, S., et al., "Rituximab-Dependent Cytotoxicity by Natural Killer Cells Influence of FCGR3A Polymorphism on the Concentration-Effect Relationship," Cancer Res., 64(13): 4664-4669 (2004).
Fischer A, et al., "Genetic defects affecting lymphocyte cytotoxicity," Current Opinion in Immunology, vol. 19:348-353 (2007).
Gahrton G, et al., "Role of stem cell transplantation in myeloma," Hematology,10 Suppl 1:127-128 (2005).
Godfrey J. et al., "The role of natural killer cells in immunity against multiple myeloma," Leukemia & Lymphoma, vol. 53(9): 1666-1676 (2012).
Greipp P., "Treatment Paradigms for the Newly Diagnosed Patient With Multiple Myeloma," Seminars in Hematolgy, vol. 42:S16-S21(2005).
Hari P, et al.,"Cure of multiple myeloma—more hype, less reality," Bone Marrow Transplant, 37:1-18 (2006).
Haycock GB, et al., "Geometric method for measuring body surface area: a height-weight formula validated in infants, children, and adults," J Pediatr, vol. 93:62-66 (1978).
Hsi, E.D., et al., "CS1, a Potential New Therapeutic Antibody Target for the Treatment of Multiple Myeloma," Clin. Cancer Res., 14(9):2775-2884 (2008).
International Preliminary Report on Patentability, PCT/US2014/064153, dated May 10, 2016, 9 pages.
International Search Report and Written Opinion, PCT/US2014/064153, dated Feb. 20, 2015, 15 pages.
Lee JK, et al.,"CS1 (CRACC, CD319) induces proliferation and autocrine cytokine expression on human B lymphocytes," J Immunol,179:4672-4678 (2007).
Murphy JJ, "A novel immunoglobulin superfamily receptor (19A) related to CD2 is expressed on activated lymphocytes and promotes homotypic B-cell adhesion," Biochem J,361:431-436 (2002).
Murphy WJ, et al., "NK cells—from bench to clinic," Biol Blood Marrow Transplant, 18:S2-S7 (2012).
Purdy AK et al., "Natural killer cells and cancer: Regulation by the killer cell Ig-like receptors (KIR)," Cancer Biology & Therapy, vol. 8(23): 2209-2218 (2009).
Romagne, F. et al., "Preclinical characterization of 1-7F9, a novel human anti-KIR receptor therapeutic antibody that augments natural killer-mediated killing of tumor cells," Blood, 114(13): 2667-2677 (2009).
Smith D. et al., "Multiple myeloma," BMJ, vol. 26:346:11 pages (2013).
Sola C., et al., "Genetic and antibody-mediated reprogramming of natural killer cell missing-self recognition in vivo," PNAS, 106(31): 12879-12884 (2009).
Straat, F.G., et al., "A novel PCR-based method for direct Fc gamma receptor IIIa (CD16) allotyping," J. Immunol Methods, 242(1-2): 127-132 (2000).
Tai Y, et al., "Anti-CS1 humanized monoclonal antibody HuLuc63 inhibits myeloma cell adhesion and induces antibody-dependent cellular cytotoxicity in the bone marrow milieu," Blood, 112:1329-1337 (2008).
Tai Yu-Tzu et al., "CS1 promotes multiple myeloma cell adhesion, clonogenic growth, and tumorigenicity via c-maf-mediated interactions with bone marrow stromal cells," Blood, 113(18): 4309-4318 (2009).
Uhrberg M., et al., "The Repertoire of Killer Cell Ig-Like Receptor and CD94:NKG2A Receptors in T Cells: Clones Sharing Identical alpha beta TCR Rearrangement Express Highly Diverse Killer Cell Ig-Like Receptor Patterns," J. Immunol. ,166:3923-3932 (2001).
Van Rhee, F., et al., "Combinatorial efficacy of anti-CS1 monoclonal antibody elotuzumab (HuLuc63) and bortezomib against multiple myeloma," Mol. Cancer Ther., 8(9):2616-2624 (2009).
Veillette A., "NK cell regulation by SLAM family receptors and SAP-related adapters," Immunological Reviews, vol. 214:22-34 (2006).
Verbraecken, J. et al., "Body surface area in normal-weight, overweight, and obese adults. A comparison study," 55(4):515-24 (2006).
Vivier , E. et al., "Innate or Adaptive immunity? The example of natural killer cells," Science, vol. 331(6013):44-49 (2011).

\* cited by examiner

Characterization of NK cells within PBMC. NK cells are identified as CD3-CD56+ lymphocytes (top row). CD16 expression was measured with different anti-CD16 mAb (3G8 or MEM154) to confirm CD16 PCR typing results (middle row). KIR2DL2, -2DL3, -2DS2 expression was measured with GL183 mAb (CD158b1b2, bottom left panel). KIR2DL1 was measured with 143211 mAb (CD158a, bottom right panel).

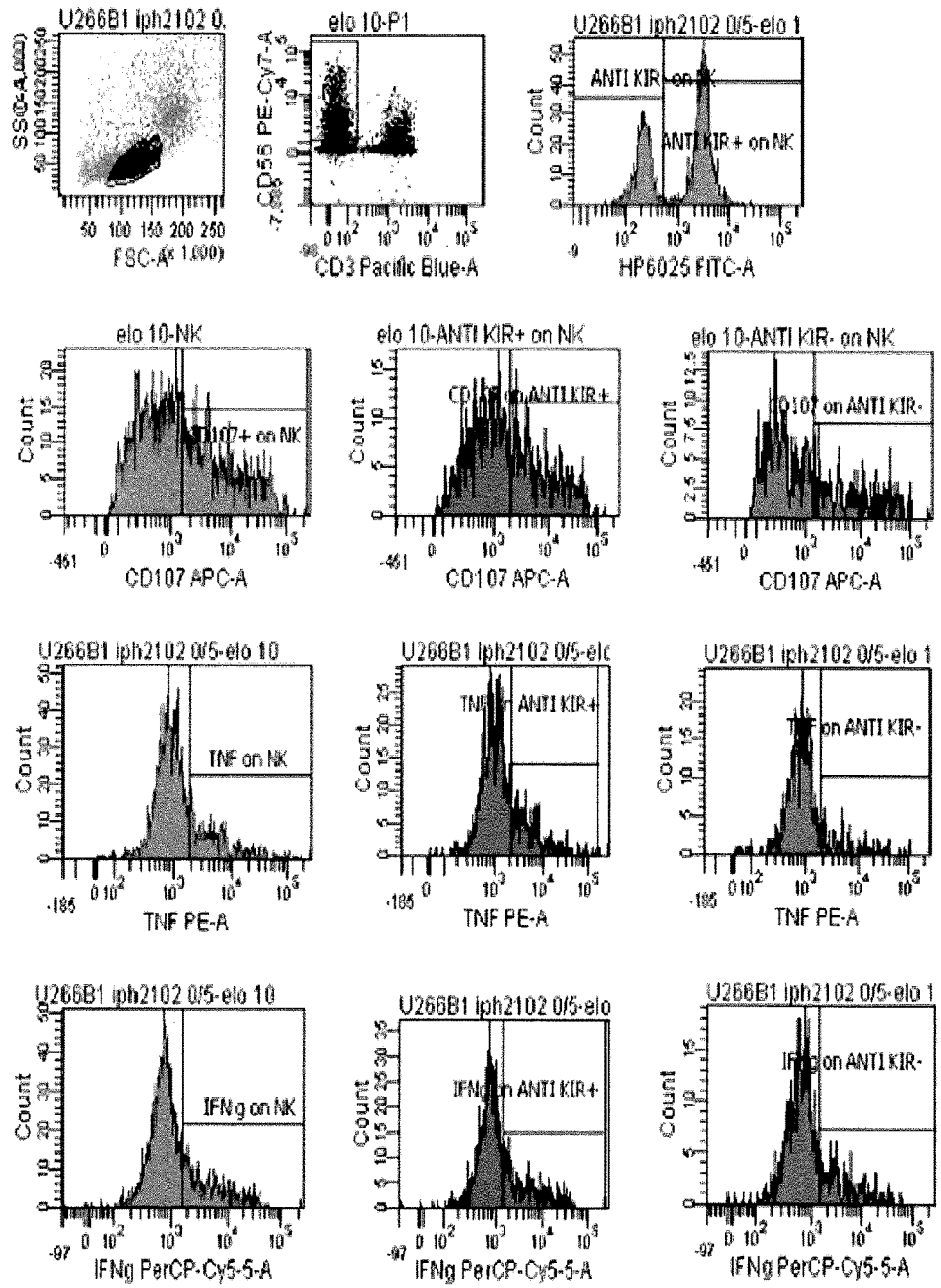

Fig. 3

Gating strategy. Example from 20060411b volunteer's PBMC vs. U266B1 in presence of 10 µg/mL of elotuzumab and 0.5 µg/mL lirilumab. Top row indicates NK cells gating with PBMC identified as CD3- CD56+ lymphocytes. Top right panel indicates identification of lirilumab positive (anti-KIR+ on NK) and negative (anti-KIR- on NK) NK cells. CD107 mobilization, intracellular TNF-α and intracellular IFN-γ are indicated on second, third and fourth row respectively. These stainings are shown on total NK cells (left column), lirilumab positive NK cells (middle column) and lirilumab-negative NK cells (right column).

| Donor ID | Experiment Name/date | PBMC ||||| U266B1 || OPM-2 ||
|---|---|---|---|---|---|---|---|---|---|---|
| | | CD16 typing | CD16 MFI ratio | HLA-C typing | % NK in PBMC | % lirilumab positive NK cells | HLA-ABC MFI ratio | CS-1 MFI ratio | HLA-ABC MFI ratio | CS-1 MFI ratio |
| 20060428b | 120808EB Exp6 | F/V | ND | C1/C2 | 18% | 76% | 400 | 9 | 217 | 35 |
| 20060512b | 120813EB Exp7 | F/F | 122 | C1/C1 | 7% | 37% | 344 | 7 | 147 | 27 |
| 20060512a | 120925EB Exp9 | F/F | 303 | C1/C2 | 7% | 52% | 244 | 7 | 182 | 29 |
| 20060419a | 120925EB Exp9 | F/V | 504 | C1/C2 | 10% | 42% | | | | |
| 20060426b' | 120928EB Exp10 | F/V | 1061 | C2/C2 | 10% | 33% | 466 | 14 | 256 | 53 |
| 2000414a | 121002EB Exp11 | F/F | 266 | C1/C1 | 19% | 52% | 184 | 5 | 144 | 22 |
| 20060420 | 121002EB Exp11 | F/V | 587 | C1/C2 | 28% | 59% | | | | |
| 20060411b | 121004EB Exp12 | F/F | 239 | C1/C2 | 14% | 68% | 254 | 5 | 192 | 25 |
| DVS217 | 130404EB Exp15 | V/V | 550 | ND | 8% | 38% | 380 | 30 | 136 | 78 |
| DS21-S2109 | 130409EB Exp16 | V/V | 633 | C1/C1 | 4% | 39% | 251 | 15 | 216 | 68 |
| DVS647 | 130412EB Exp17 | V/V | 457 | ND | 10% | 51% | 220 | 12 | 220 | 59 |
| 20060413a | 130421EB Exp17 | V/V | 320 | C1/C2 | 22% | 43% | | | | |
| | Mean | | 458 | | 13% | 49% | 305 | 12 | 190 | 44 |
| | SD | | 257 | | 7% | 13% | 96 | 8 | 41 | 21 |

Fig. 4

Figure 4: Summary of target cell lines and effector cells characteristics in each experiment. Outlined value is an outlier according to a Grubb's test for outliers.

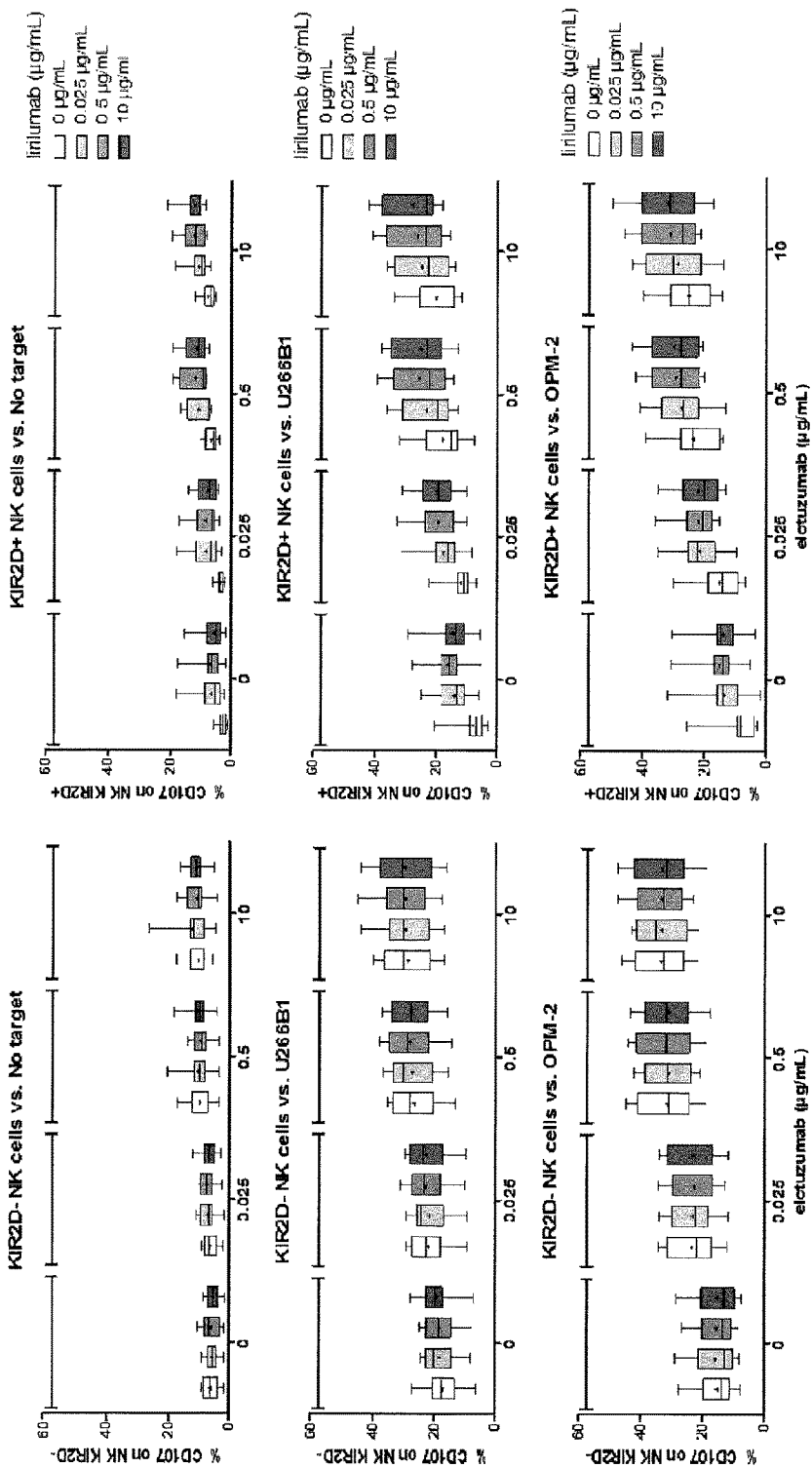

Fig. 5

CD107 mobilization on NK cells expressing KIR2D (KIR2D+ NK cells, right column) targeted by lirilumab or on NK cells not expressing KIR2D (KIR2D- NK cells, left column). CD107 mobilization is measured on indicated NK cells within PBMC in medium only (top panel), within PBMC incubated with U266B1 (middle panel) or with OPM-2 (bottom panel). Box plots indicate the median with the second and third quartiles. Whiskers indicate min. and max. values. + indicates the mean. N=12 healthy volunteers.

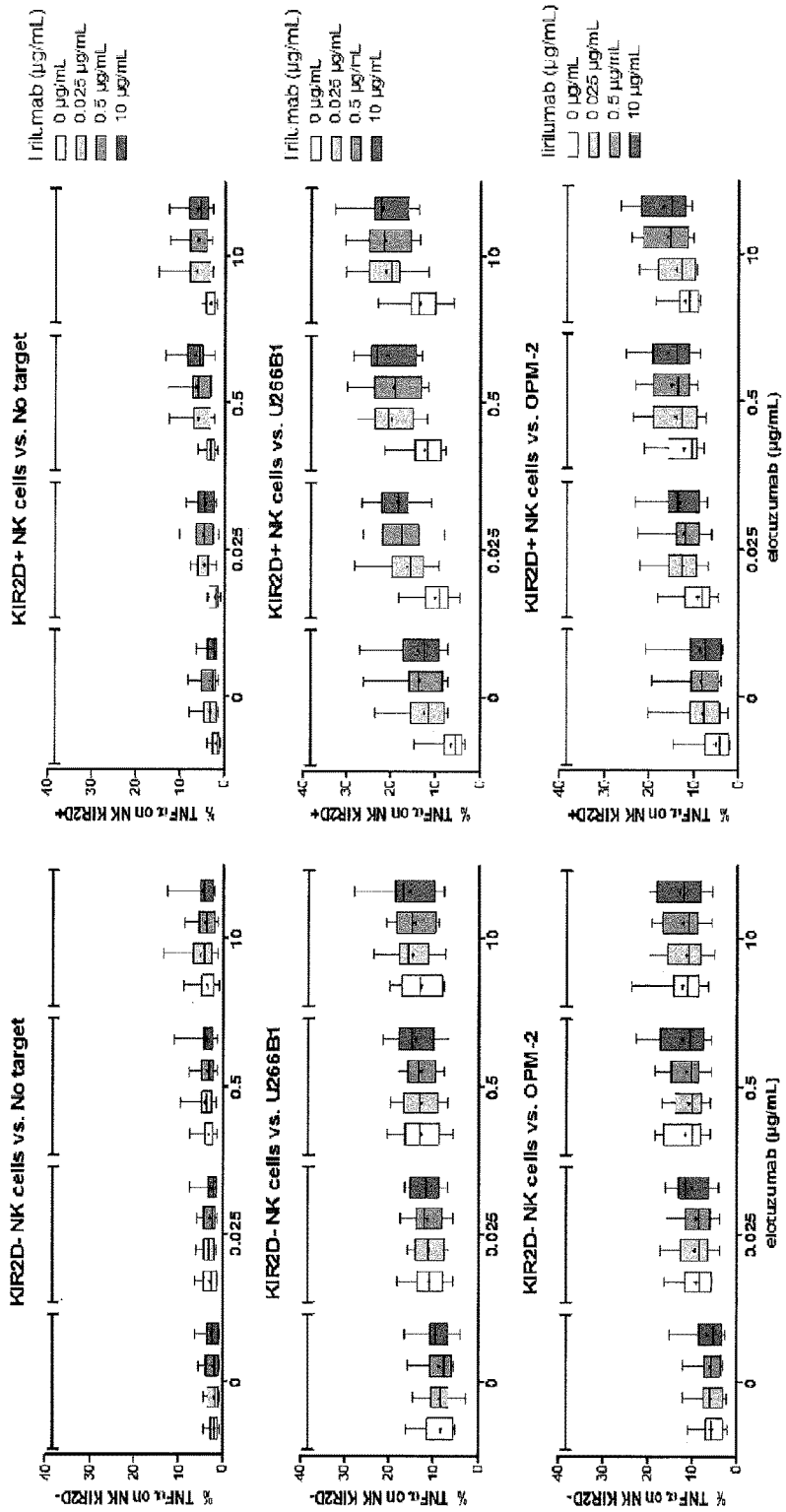

Fig. 6

Intracellular TNF-α production in NK cells expressing KIR2D (KIR2D+ NK cells, right column) targeted by lirilumab or on NK cells not expressing KIR2D (KIR2D- NK cells, left column). Intracellular TNF-α production is measured on indicated NK cells within PBMC in medium only (top panel), within PBMC incubated with U266B1 (middle panel) or with OPM-2 (bottom panel). Box plots indicate the median with the second and third quartiles. Whiskers indicate min. and max. values. + indicates the mean. N=12 healthy volunteers.

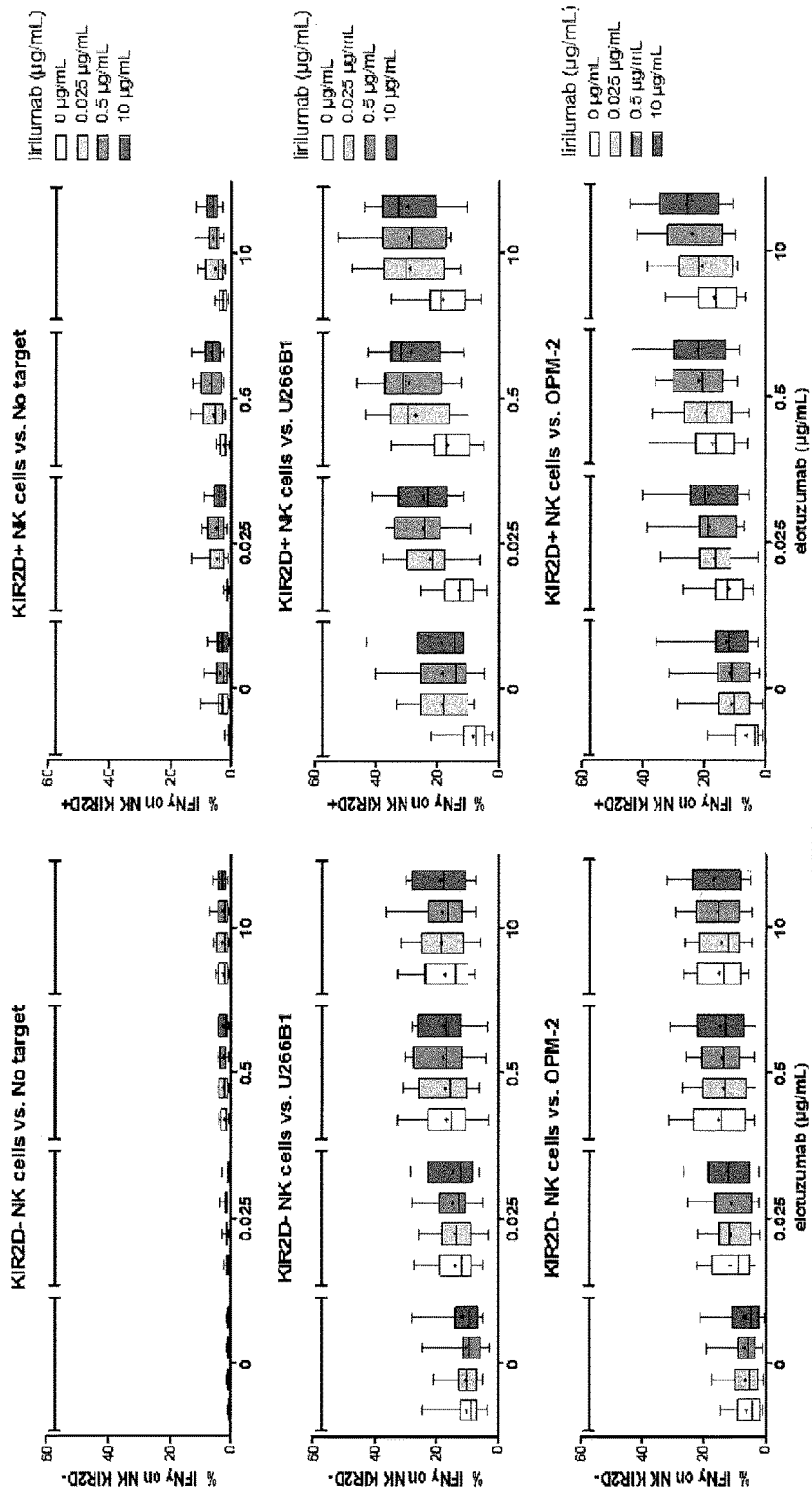

Fig. 7

Intracellular IFN-γ production in NK cells expressing KIR2D (KIR2D+ NK cells, right column) targeted by lirilumab or on NK cells not expressing KIR2D (KIR2D- NK cells, left column). Intracellular IFN-γ production is measured on indicated NK cells within PBMC in medium only (top panel), within PBMC incubated with U266B1 (middle panel) or with OPM-2 (bottom panel). Box plots indicate the median with the second and third quartiles. Whiskers indicate min. and max. values. + indicates the mean. N=12 healthy volunteers.

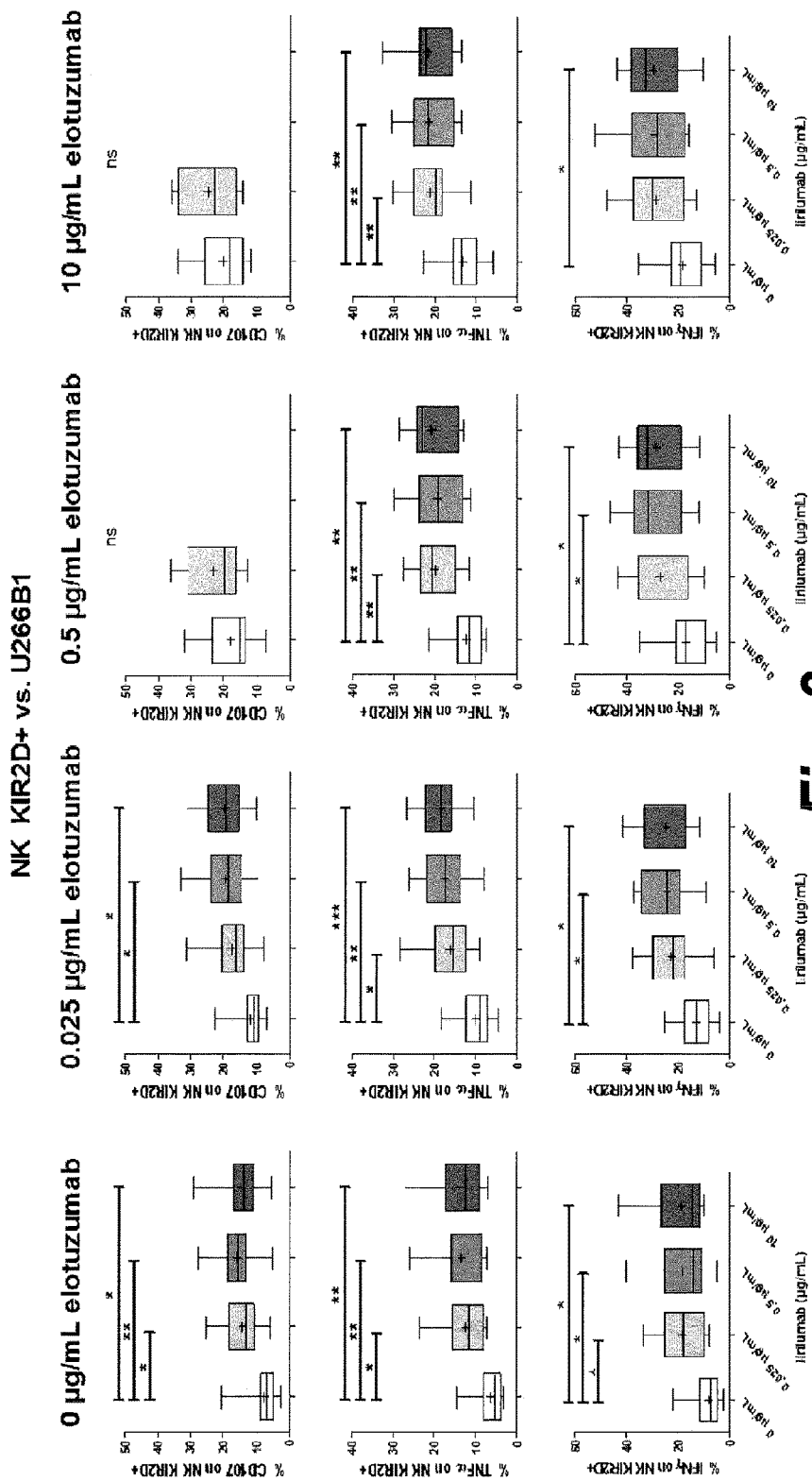

Fig. 8

CD107 mobilization (Top), intracellular TNF-α production (Middle) and intracellular IFN-γ production (bottom) in NK cells expressing KIR2D in response to U266B1 with indicated doses of lirilumab and elotuzumab. Box plots indicate the median with the second and third quartiles. Whiskers indicate min. and max. values. + indicates the mean. N=12 healthy volunteers. Groups were compared using a one-way ANOVA and a Bonferroni multiple comparison test.

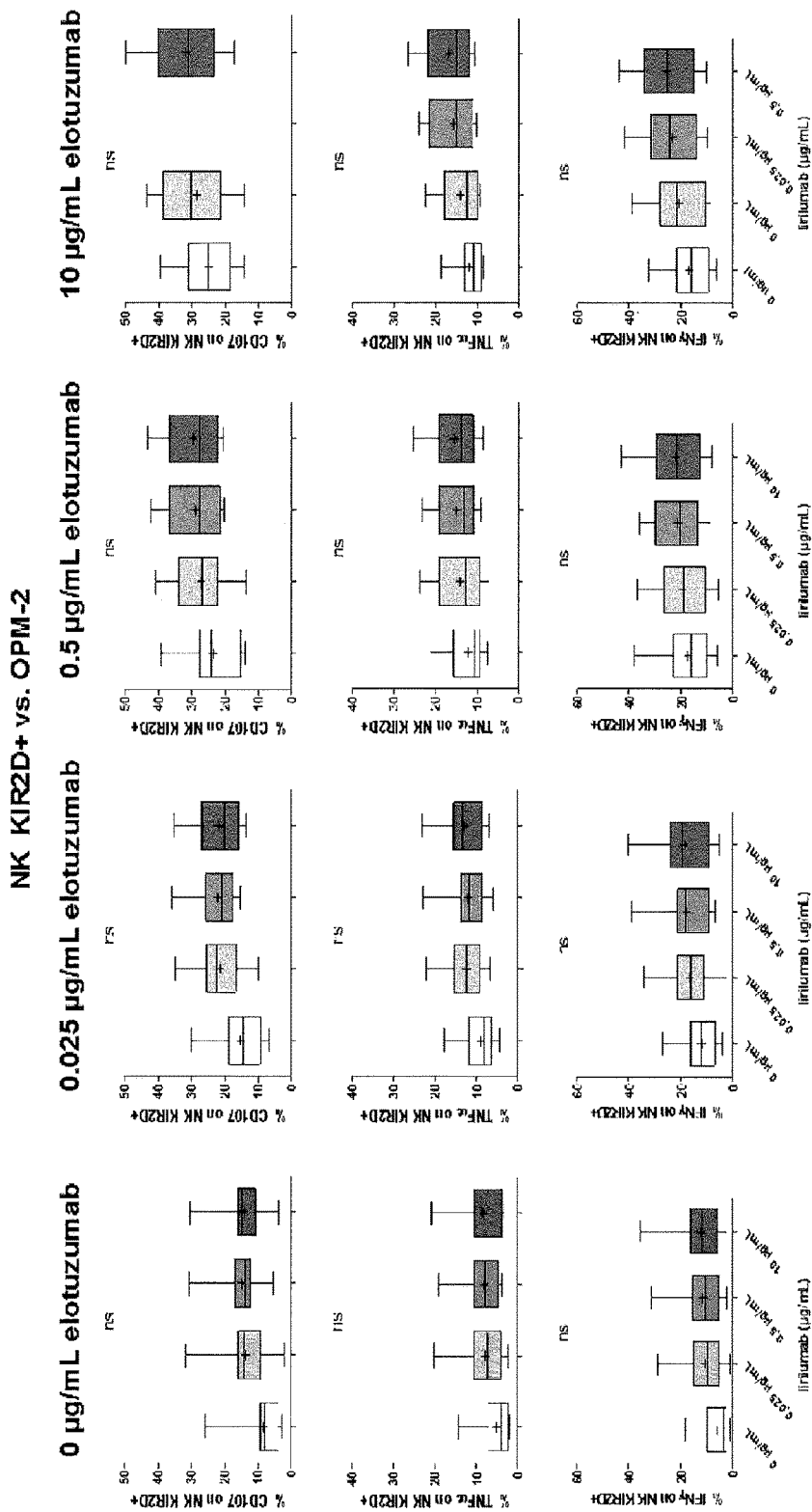

Fig. 9

CD107 mobilization (Top), intracellular TNFα production (Middle) and intracellular IFN-γ production (bottom) in NK cells expressing KIR2D in response to OPM-2 with indicated doses of lirilumab and elotuzumab. Box plots indicate the median with the second and third quartiles. Whiskers indicate min. and max. values. + indicates the mean. N=12 healthy volunteers. Groups were compared using a one-way ANOVA and a Bonferroni multiple comparison test.

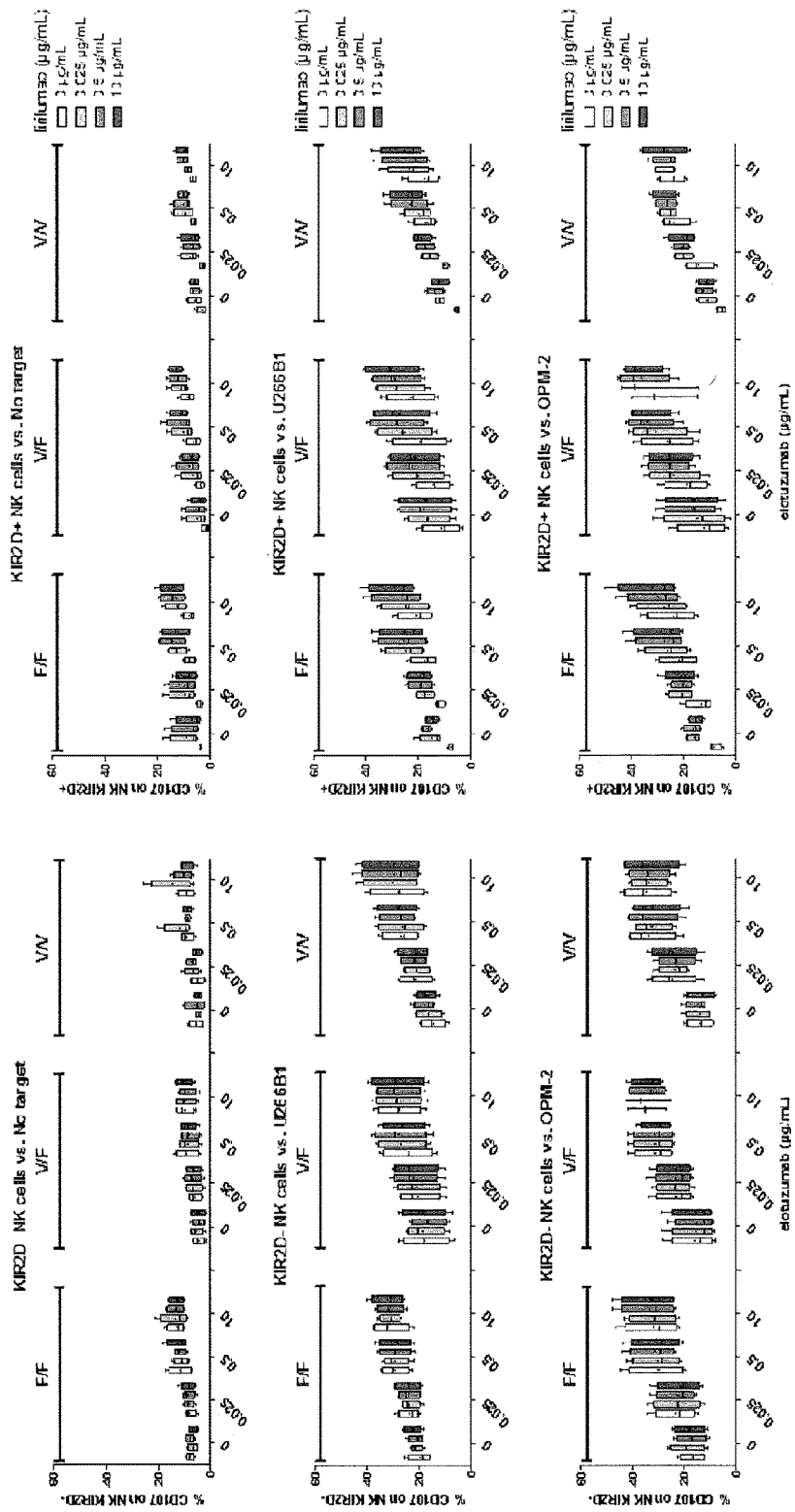

Fig. 10

CD107 mobilization on NK cells expressing KIR2D (KIR2D+ NK cells, right column) targeted by lirilumab or on NK cells not expressing KIR2D (KIR2D- NK cells, left column). CD107 mobilization is measured on indicated NK cells within PBMC in medium only (top panel), within PBMC incubated with U266B1 (middle panel) or with OPM-2 (bottom panel). Box plots indicate the median with the second and third quartiles. Whiskers indicate min. and max. values. + indicates the mean. N=4 healthy volunteers per CD16 genotype (F/F, V/F or V/V).

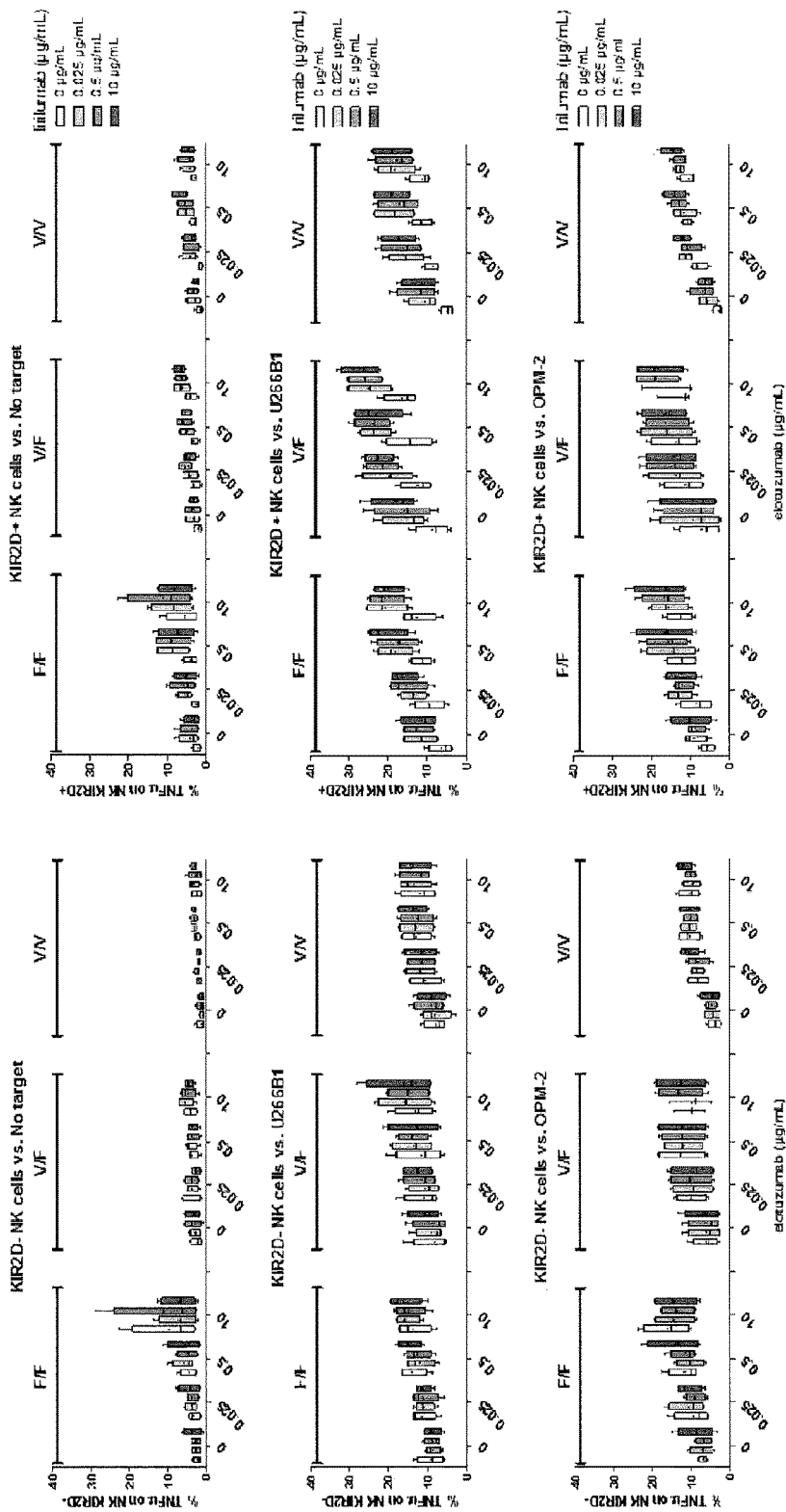

Fig. 11

Intracellular TNF-α production on NK cells expressing KIR2D (KIR2D- NK cells, right column) targeted by lirilumab or on NK cells not expressing KIR2D (KIR2D- NK cells, left column). Intracellular TNF-α production is measured on indicated NK cells within PBMC in medium only (top panel), within PBMC incubated with U266B1 (middle panel) or with OPM-2 (bottom panel). Box plots indicate the median with the second and third quartiles. Whiskers indicate min. and max. values. + indicates the mean. N=4 healthy volunteers per CD16 genotype (F/F, V/F or V/V).

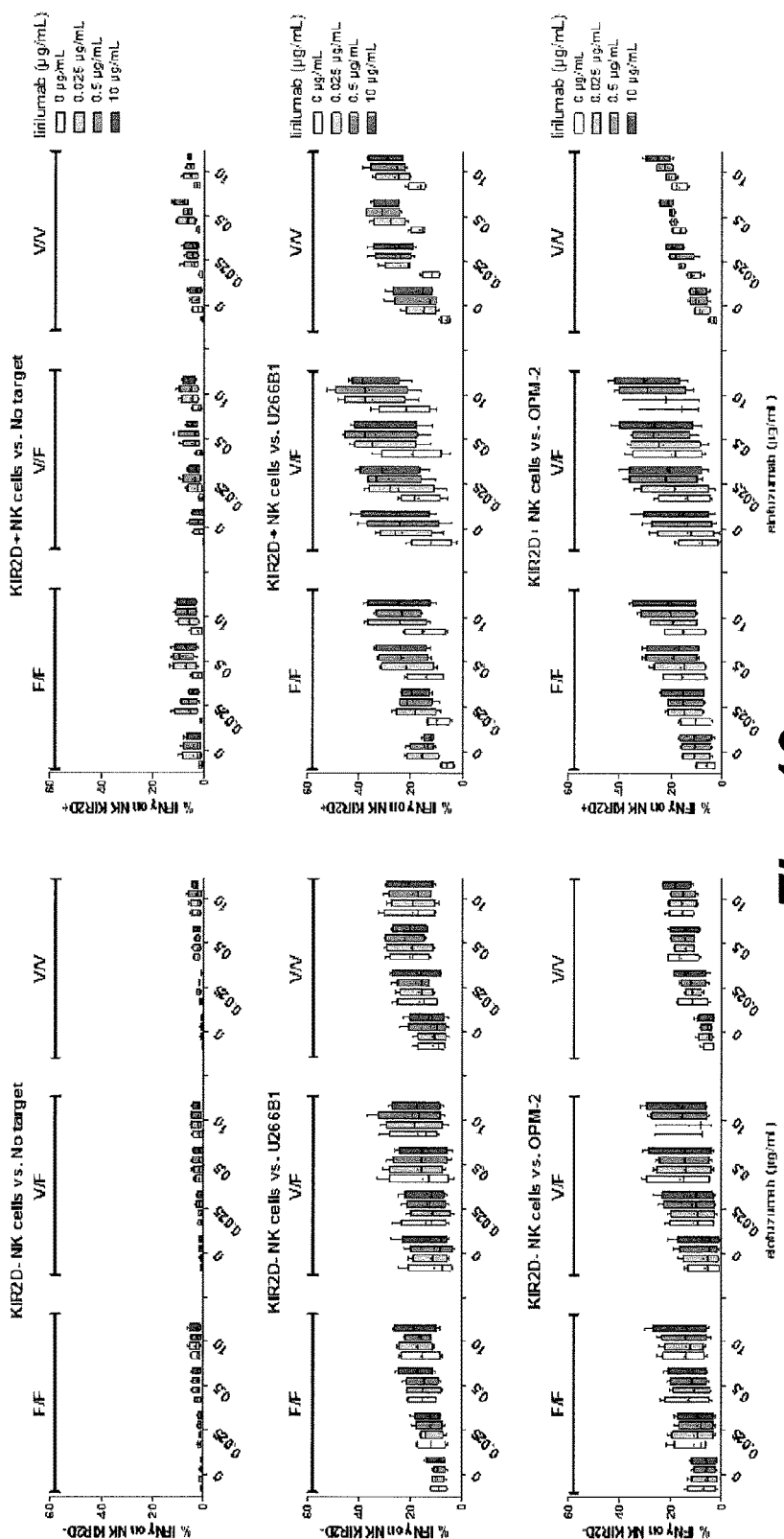

Fig. 12

Intracellular IFN-γ production on NK cells expressing KIR2D (KIR2D+ NK cells, right column) targeted by lirilumab or on NK cells not expressing KIR2D (KIR2D- NK cells, left column). Intracellular IFN-γ production is measured on indicated NK cells within PBMC in medium only (top panel), within PBMC incubated with U266B1 (middle panel) or with OPM-2 (bottom panel). Box plots indicate the median with the second and third quartiles. Whiskers indicate min. and max. values. + indicates the mean. N=4 healthy volunteers per CD16 genotype (F/F, V/F or V/V).

Cell dependent growth of OPM-2 SC engrafted in KIRtg-Rag mice (individual curves). 5, 10 and 15.106 OPM-2 cells were engrafted SC in n=8 mice.

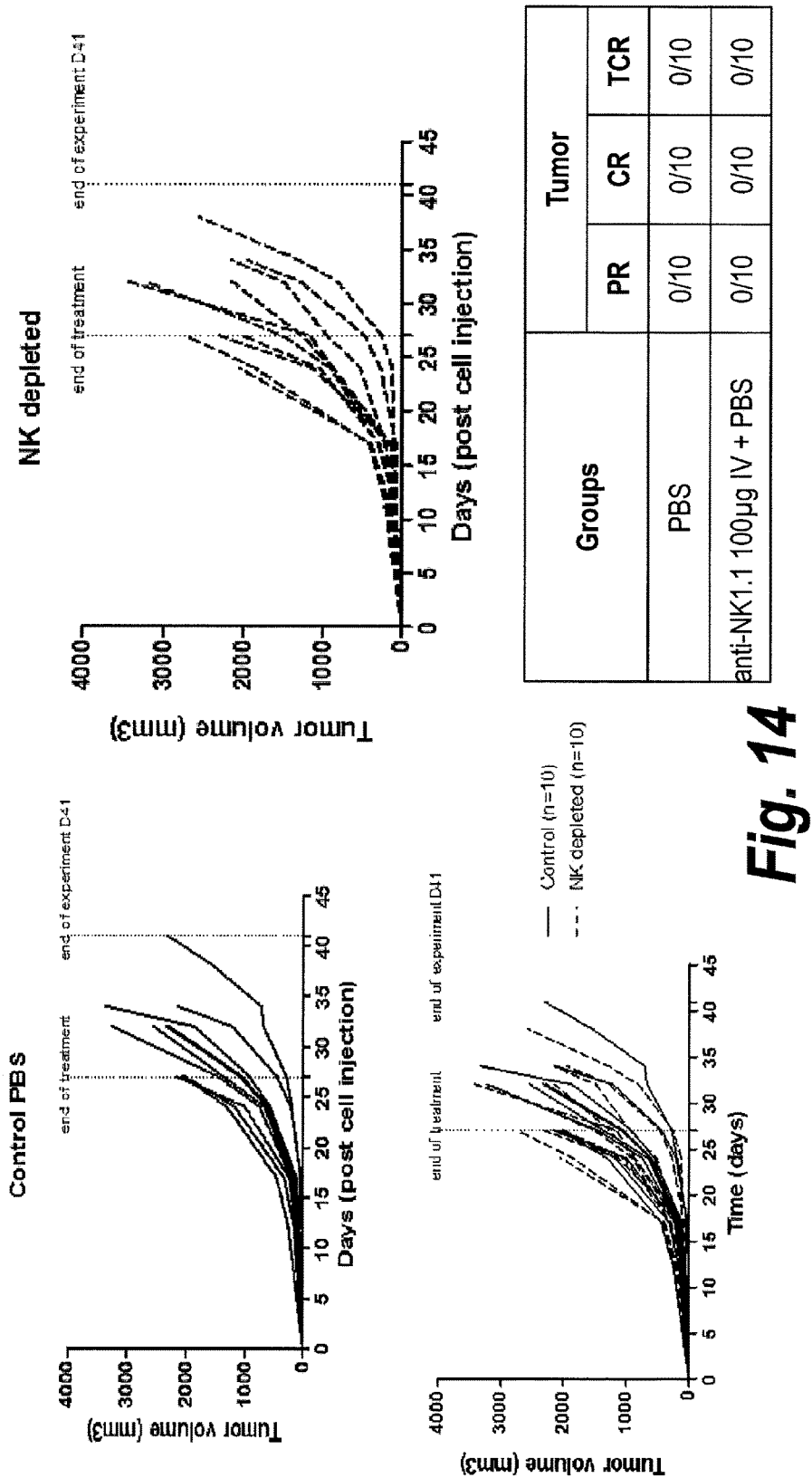

Fig. 14

Effect of NK depletion on SC OPM-2 growth in KIRtg-RAG mice (n=10). Two upper graphs: individual curves of mice engrafted SC with 5.10$^6$ OPM-2 without (left graph) anti-NK1.1 treatment. Lower graph: the superposition of individual curves of both groups. The table represents tumor growth curve profiles in each group: partial regression (PR), complete regression (CR) and temporary complete regression (TCR).

Right panel: Doubling time (DT) of control and NK depleted group (n=10).
Left panel: Tumor Growth Delay (TGD) of NK depleted group related to control group calculated at 4 different tumor volumes.

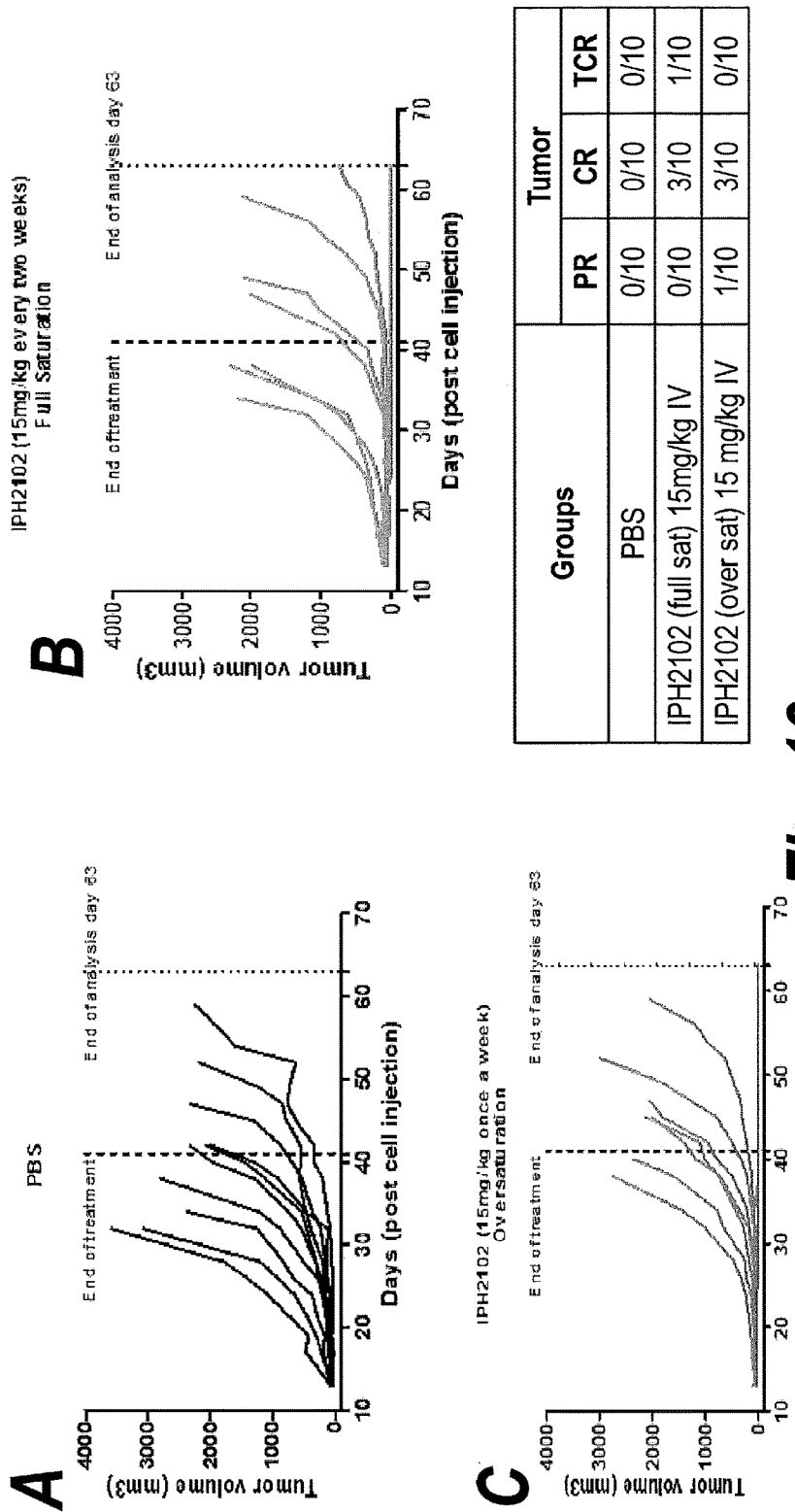

Fig. 16

Antitumoral activity of lirilumab (IPH2102) in KIRtg-RAG mice engrafted with 5.10^6 OPM-2 SC (n=10).
A) Individual curves of PBS treated animals.
B) Individual curves of IPH2102 treated animals at a concentration that saturate KIR receptors.
C) Individual curves of IPH2102 treated animals at a concentration above the concentration that saturate KIR receptors.
Lower right graph: individual curves of IPH2102 treated animals at a concentration above the concentration that saturate KIR receptors.
The table represents tumor growth curve profiles in each group: partial regression (PR), complete regression (CR) and temporary complete regression (TCR).

Efficacy of lirilumab on the survival of KIRtg-RAG mice engrafted with 5.10⁶ OPM-2 SC (n=10). Kaplan Meier survival curves and Mantel-Cox statistical analysis : Gating strategy for OPM-2 and tumor infiltrating NK.
In KIRtg-RAG mice, T and B lymphocytes are present but not functional because of the lack of RAG enzyme. Lymphocytes are gated on the basis on FSC (forward side scatter) SSC (side scatter) parameters and then discriminated on their expression of mCD45

Correlation between CS1 and Class-I expression and tumor volume (left graph) or time post engraftment (right graph).

Correlation between NK infiltrated the tumor and tumor volume.

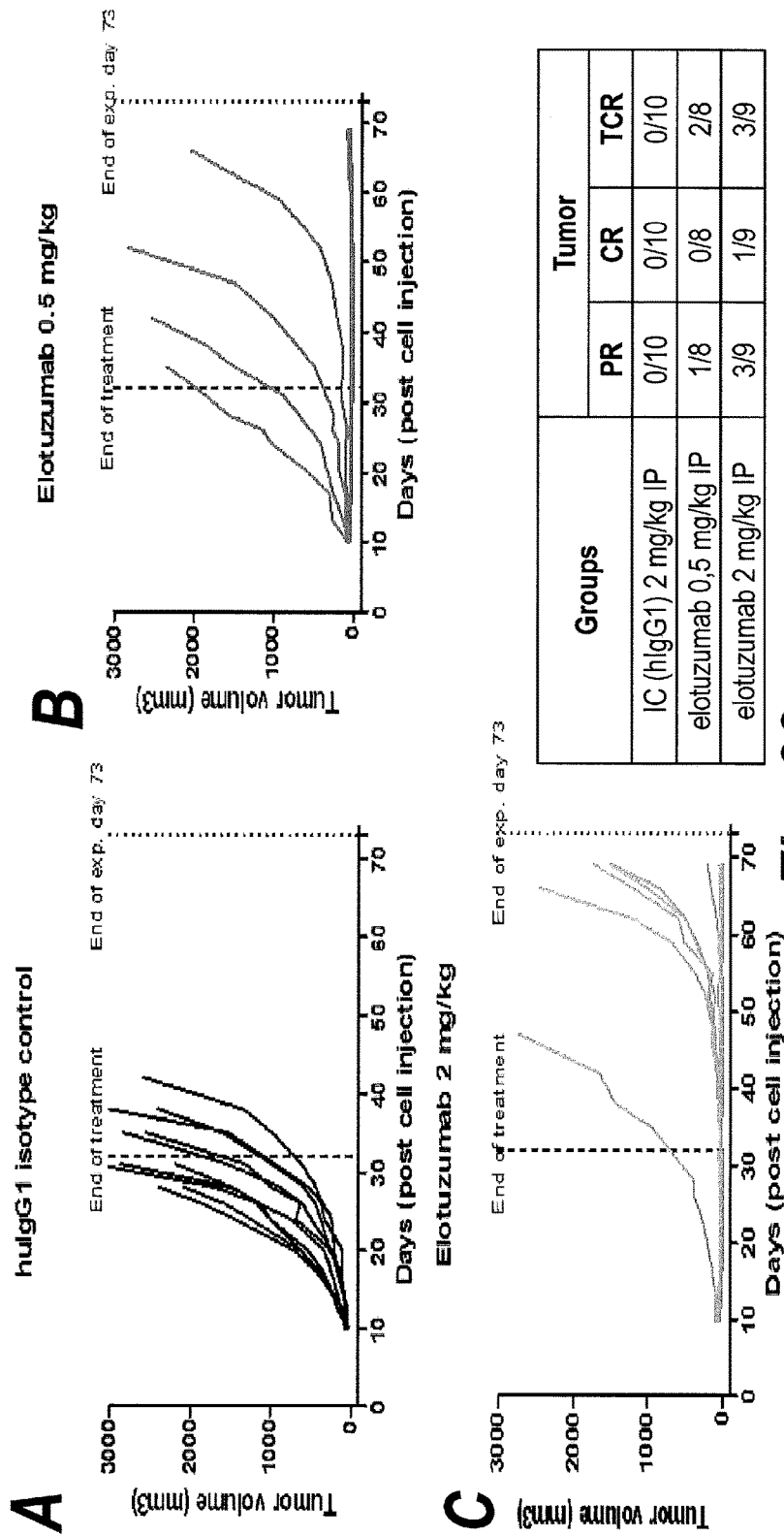

Fig. 22

Antitumoral activity of elotuzumab in KIRtg-RAG mice engrafted with 5.106 OPM-2 SC.
A) Individual curves of huIgG1 IP treated animals (n=10)
B) Individual curves of elotuzumab treated animals at a dose of 0.5mg/kg IP (n=8)
C) Individual curves of elotuzumab treated animals at a dose of 2mg/kg IP (n=9)
The table represents tumor growth curve profiles in each group: partial regression (PR), complete regression (CR) and temporary complete regression (TCR).

Comparison of elotuzumab treated groups with the control at day 28 post graft.
Data are expressed as individual tumor volume and median. huIgG1 IP n=10; elotuzumab 0.5mg/kg IP n=8; elotuzumab 2mg/kg IP n=9. Statistical analysis: Kruskal-Wallis non parametric test followed by a Dunn's multiple comparison test. * for p<0.05; ** for p<0.01

: Efficacy of elotuzumab on the survival of KIRtg-RAG mice engrafted with 5.10⁶ OPM-2 SC. Kaplan Meier survival curves, median survival can not be determined. huIgG1 IP n=10; elotuzumab 0.5mg/kg IP n=8; elotuzumab 2mg/kg IP n=9

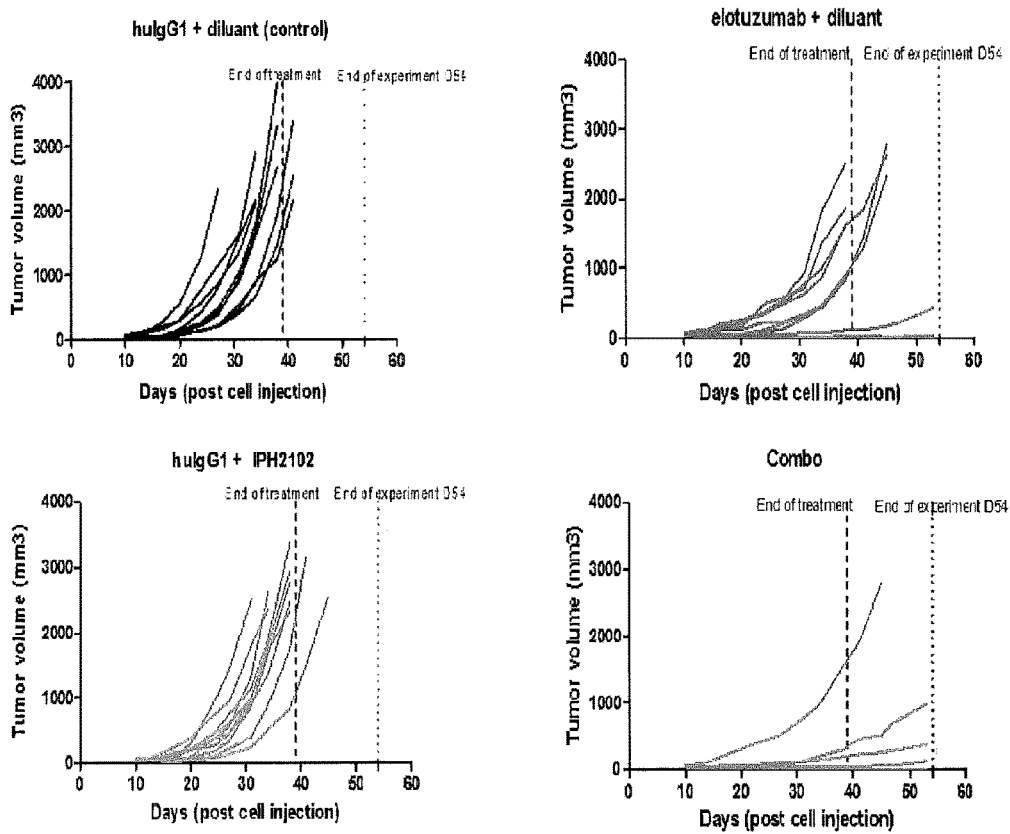

Fig. 25

Combined activity of elotuzumab and lirilumab (IPH2102) in KIRtg-RAG mice engrafted with 5.106 OPM-2 SC (n=10).
Upper left graph: individual curves of huIgG1 IP + diluent IV treated animals. Upper right graph: individual curves of elotuzumab 0.5mg/kg IP + diluent IV treated animals. Lower left graph: individual curves of huIgG1 IP + IPH2102 "full sat" 15mg/kg IV treated animals. Lower right graph: individual curves of elotuzumab 0.5mg/kg IP + IPH2102 "full sat" 15mg/kg IV treated animals
The table represents tumor growth curve profiles in each group: partial regression (PR), complete regression (CR) and temporary complete regression (TCR).

Comparison of elotuzumab, IPH2102 and combined treated groups with the control at day 27 post graft. Data are expressed as individual tumor volume and medianStatistical analysis: Kruskal-Wallis non parametric test followed by a Dunn's multiple comparison test. ** for $p<0.01$ Efficacy of elotuzumab, IPH2102 and combined treatments on the survival of KIRtg-RAG mice engrafted with 5.106 OPM-2 SC. Kaplan Meier survival curves.

Involvement of NK in the combined activity of elotuzumab and lirilumab (IPH2102) in KIRtg-RAG mice engrafted with 5.106 OPM-2 SC (n=10).
A: Curves of huIgG1 IP + diluent IV treated animals
The table represents tumor growth curve profiles in each group: partial regression (PR), complete regression (CR) and temporary complete regression (TCR).

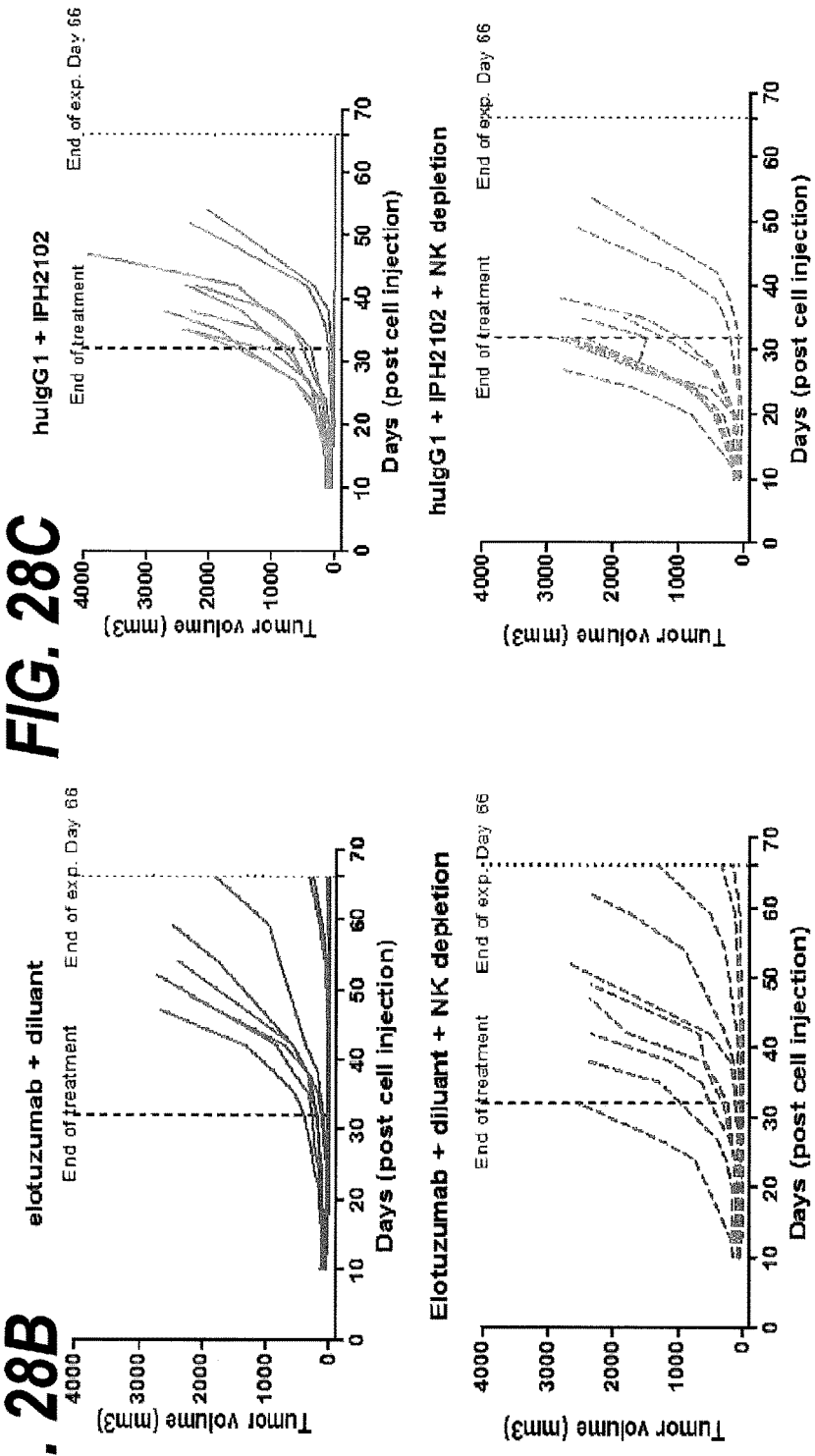

Involvement of NK in the combined activity of elotuzumab and lirilumab (IPH2102) in KIRtg-RAG mice engrafted with 5.106 OPM-2 SC (n=10).
B: Individual curves of elotuzumab 0.5mg/kg IP + diluent IV treated animals without (upper graph) or with (lower graph) anti-NK1.1 treatment.
C: Individual curves of huIgG1 IP + IPH2102 "full sat" 15mg/kg IV treated animals without (upper graph) or with (lower graph) anti-NK1.1 treatment.
The table represents tumor growth curve profiles in each group: partial regression (PR), complete regression (CR) and temporary complete regression (TCR).

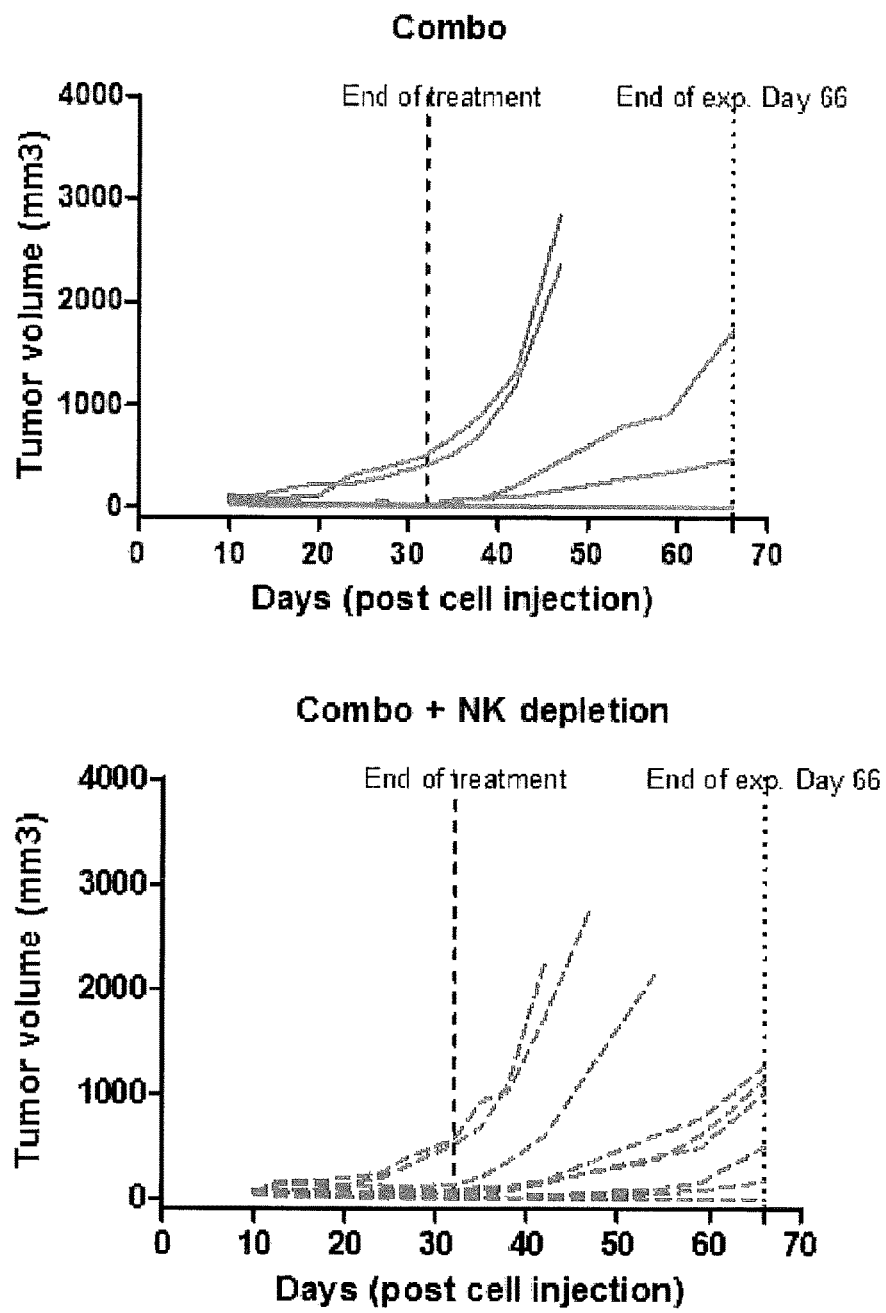

Fig. 28D

Involvement of NK in the combined activity of elotuzumab and lirilumab (IPH2102) in KIRtg-RAG mice engrafted with 5.106 OPM-2 SC (n=10).
D: Individual curves of elotuzumab 0.5mg/kg IP + IPH2102 "full sat" 15mg/kg IV treated animals without (upper graph) or with (lower graph) anti-NK1.1 treatment.
The table represents tumor growth curve profiles in each group: partial regression (PR), complete regression (CR) and temporary complete regression (TCR).

Tumor growth delay of the different treated groups related to the control (huIgG1 + diluent) calculated at 4 predetermined tumor volumes. For elotuzumab and IPH2102, TGD was calculated with n=8 mice Doubling time of the different treated groups.
Box plots indicate the median with the second and third
quartiles. Whiskers indicate min. and max. values.
DT for combo could not be determined. Statistical analysis:
One way ANOVA + Dunnett's multiple comparison test.

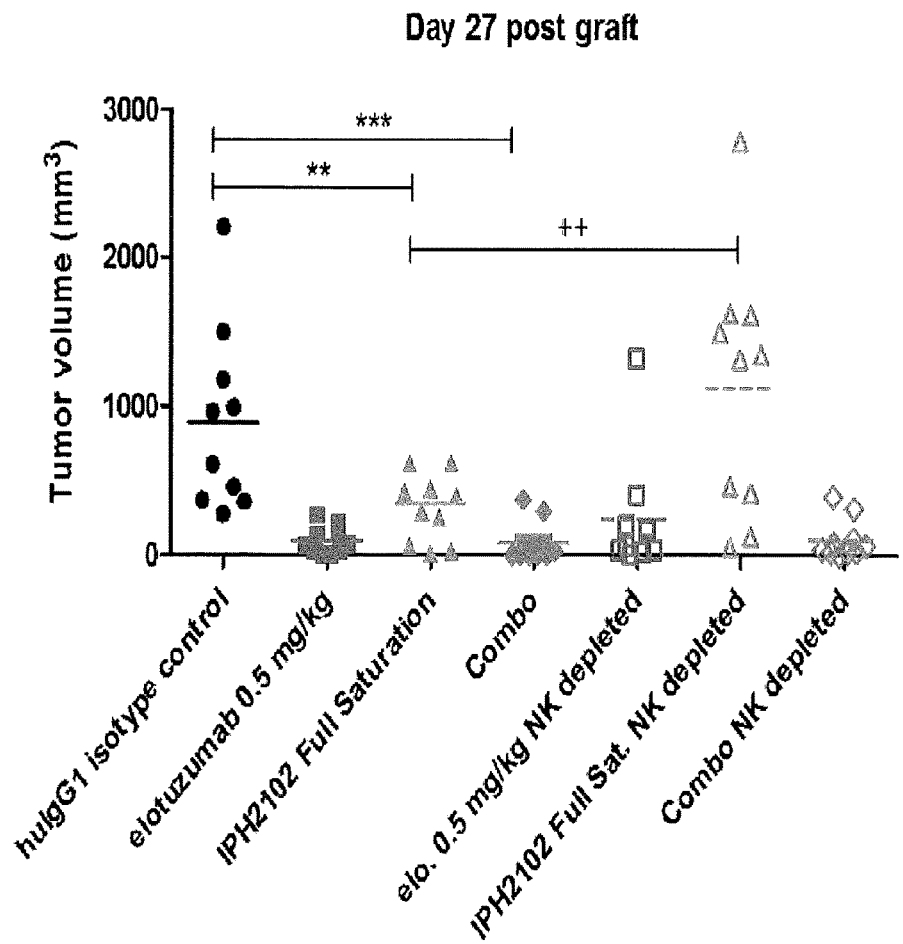

Fig. 31

Comparison of the different treated groups at day 27 post graft. Data are expressed as individual tumor volume and median. Statistical analysis: all groups were compared to the control with a Kruskal-Wallis non parametric test followed by a Dunn's multiple comparison test. ** for p<0.01. NK depleted groups were compared to their corresponding non depleted groups with unpaired t'test ++<0.05

Involvement of NK in the combined activity elotuzumab, IPH2102 and combined treatment on the survival of KIRtg-RAG mice engrafted with 5.106 OPM-2 SC. Kaplan Meier survival curves (n=10). Kaplan Meier survival curves and median survival analysis

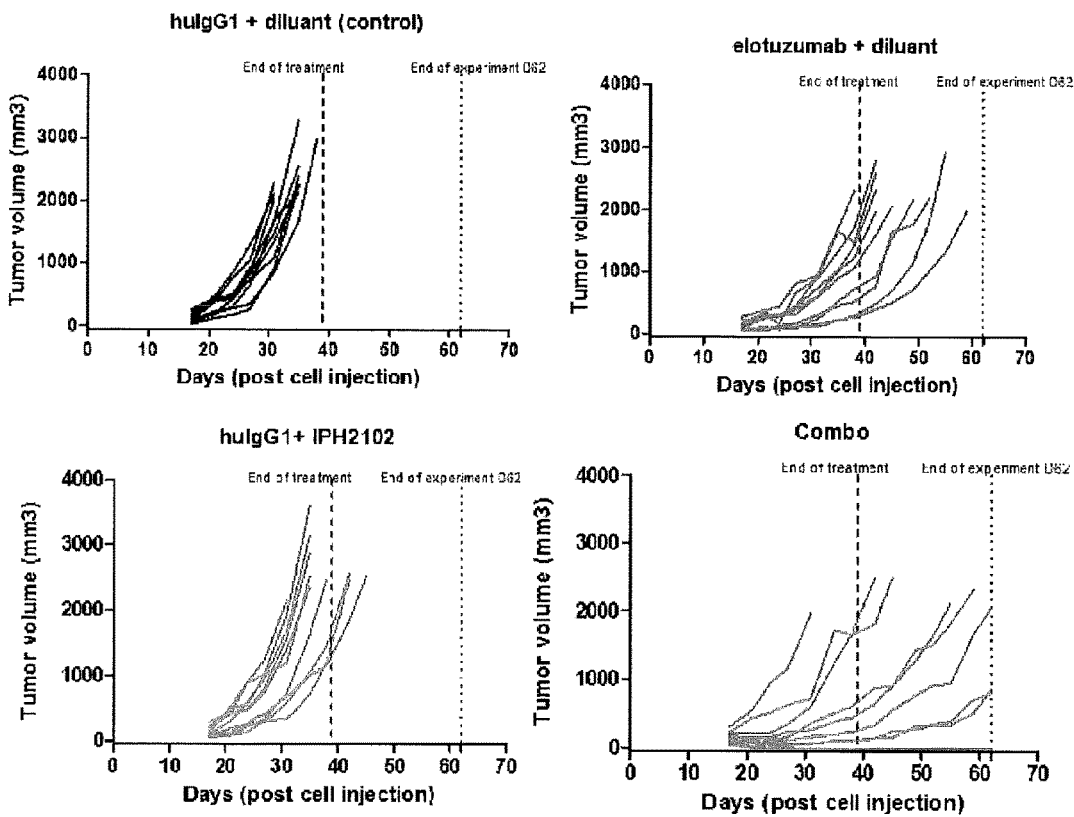

*Fig. 33*

Combined activity of elotuzumab and lirilumab (IPH2102) on high tumoral volume in KIRtg-RAG mice engrafted with 5.106 OPM-2 SC (n=10). Upper left graph: individual curves of huIgG1 IP + diluent IV treated animals. Upper right graph: individual curves of elotuzumab 0.5mg/kg IP + diluent IV treated animals. Lower left graph: individual curves of huIgG1 IP + IPH2102 "full sat" 15mg/kg IV treated animals. Lower right graph: individual curves of elotuzumab 0.5mg/kg IP + IPH2102 "full sat" 15mg/kg IV treated animals. The table represents tumor growth curve profiles in each group: partial regression (PR), complete regression (CR) and temporary complete regression (TCR).

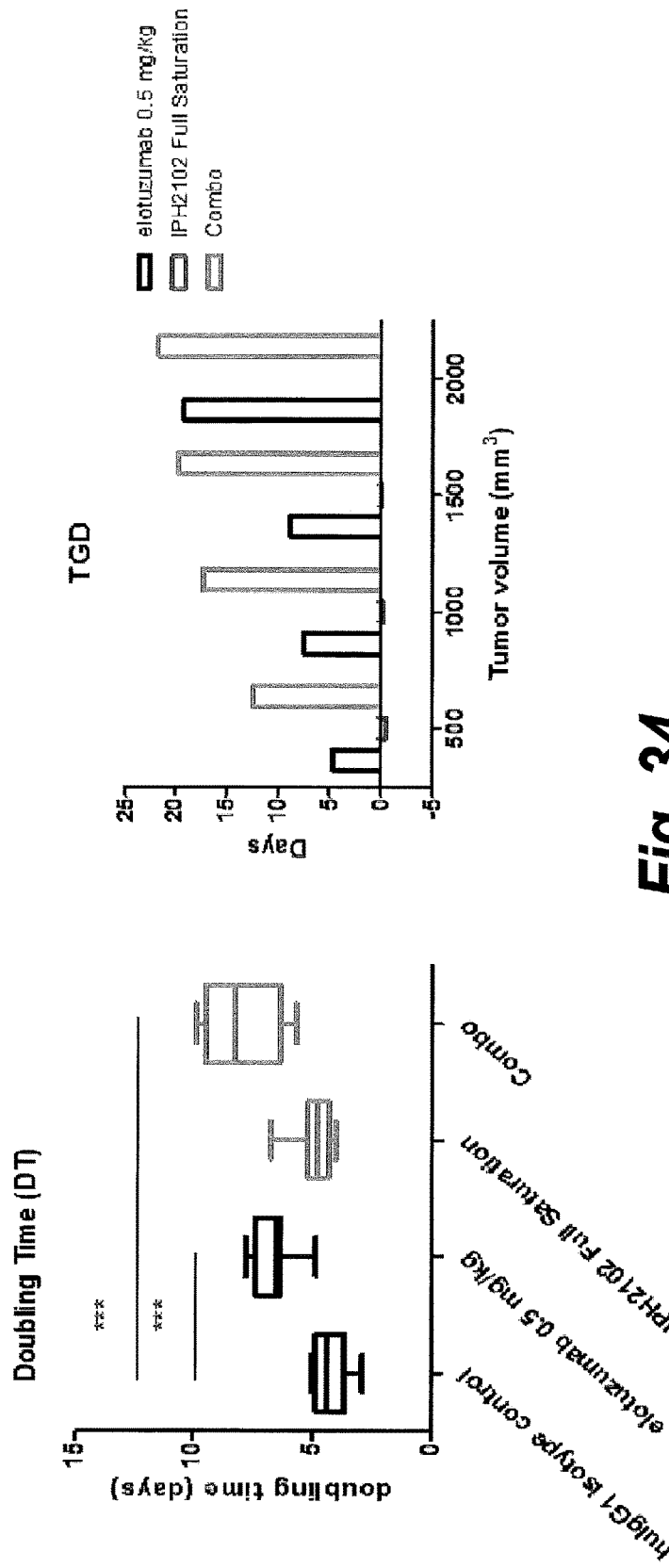

Fig. 34

Doubling time and tumor growth delay of the different treated groups related to the control (huIgG1 + diluent) calculated at 4 predetermined tumor volumes. For the combined group DT was calculated with n=8 mice. Box plots indicate the median with the second and third quartiles. Whiskers indicate min. and max. values. Statistical analysis: One way ANOVA + Dunnett's multiple comparison test.

Comparison at day 27 post graft of the different groups treated at high tumoral volume. Data are expressed as individual tumor volume and median. Statistical analysis: One way ANOVA + Dunnett's multiple comparison test.* for p<0.05, ** for p<0.01.

Efficacy of elotuzumab, IPH2102 and combined treatments, administered at high tumoral volume, on the survival of KIRtg-RAG mice engrafted with 5.10⁶ OPM-2 SC. Kaplan Meier survival curves.

COMBINATION OF ANTI-KIR AND ANTI-CS1 ANTIBODIES TO TREAT MULTIPLE MYELOMA

CROSS REFERENCE TO RELATED APPLICATIONS

This application is a 35 U.S.C. 371 national stage filing of International Application No. PCT/US2014/064153, filed on Nov. 5, 2014, which claims priority from U.S. Provisional Application No. 61/900,775, filed on Nov. 6, 2013. The contents of the aforementioned applications are hereby incorporated by reference in their entireties.

SEQUENCE LISTING

The instant application contains a Sequence Listing which has been submitted electronically in ASCII format and is hereby incorporated by reference in its entirety. Said ASCII copy, created on Apr. 7, 2016, is named MXI_533US_SL.txt and is 24,227 bytes in size.

BACKGROUND

Natural killer (NK) cells constitute 15% of peripheral blood lymphocytes and play an important role in the ability of the innate immune system to fight off viral infections and also cancer (see, e.g., Purdy A K et al., *Cancer Biol Ther* 2009; 8:13-22) and Vivier et al., *Science* 2011 Jan. 7; 331(6013):44-9). NK cells bind to target cells through multiple receptors, including natural cytotoxicity receptors (NCR), the Fc receptor CD16, NKG2D, and others. Binding of ligand to receptor initiates tyrosine phosphorylation and recruitment of accessory signaling molecules. This cascade results in activation of the NK cell, release of preformed granules containing perforin and granzymes into the target cell, and apoptosis. The concurrent release of cytokines and chemokines results in a micro-environmental milieu that recruits other immune cells. NK cells have the capability of binding every cell in the body (Murphy W J, et al., *Biol Blood Marrow Transplant* 2012; 18:S2-S7). However, binding of normal cells does not result in cytotoxic activity because of the ability of NK cells to simultaneously utilize a different set of receptors to bind major histocompatibility complex (MHC) class I molecules. Binding of human leukocyte antigen (HLA) E to the NKG2A/CD94 heterodimeric receptor, or of HLA-A, B and C molecules to inhibitory killer Ig-like receptors (KIRs), results in tyrosine phosphorylation, recruitment of the signaling adaptors SHP-1 or SHP-2, and downstream signaling. The end result is a dominant signal that suppresses normal activation signals. Thus, KIR/HLA interaction can impact NK cell responsiveness and also the development of the total number of mature responsive NK cells, known as licensing.

There are seven inhibitory KIRs and seven activating KIRs, which is one factor that results in diversity of KIR inheritance and expression. KIR is also expressed on natural killer T (NKT) cells and a small subset of T cells (Uhrberg M, et al., *J. Immunol.* 2001; 166:3923-3932). Thus, mechanistically, blockade of inhibitory KIR could induce antitumor effects by allowing for activation of NK cell and possibly also some T cells.

CS1 (also known as SLAMF7, SLAM Family Member 7, CD2 Subset, CRACC, CD2-Like Receptor-Activating Cytotoxic Cells, 19A24 Protein, 19A, CD2-Like Receptor Activating Cytotoxic Cells, CD319, Novel LY9 (Lymphocyte Antigen 9) Like Protein, Membrane Protein FOAP-12, CD319 Antigen, Protein 19A, APEX-1, FOAP12, and Novel Ly93) is a cell surface glycoprotein that is highly expressed on multiple myeloma (MM) cells. CS1 is expressed at high levels in normal and malignant plasma cells, but not normal organs, solid tumors, or $CD34^+$ stem cells. Only a small subset of resting lymphocytes, including NK cells and a subset of $CD8^+$ T cells, express detectable but low levels of CS1 (Hsi E D, et al., *Clin. Cancer Res.* 2008; 14:2775-2784 and Murphy J J, et al., *Biochem J.* 2002; 361:431-436). CS1 was isolated and cloned by Boles et al. (*Immunogenetics.* 2001; 52(3-4):302-7).

Multiple myeloma (also known as myeloma or plasma cell myeloma) is a hematological cancer formed by malignant plasma cells. Normal plasma cells are a type of white blood cell that are found in the bone marrow and make antibodies. MM is characterized by excessive numbers of abnormal plasma cells in the bone marrow and overproduction of intact monoclonal immunoglobulin (IgG, IgA, IgD, or IgE) or Bence-Jones protein (free monoclonal light chains). In MM, neoplastic plasma cells accumulate in the bone marrow and produce a monoclonal protein that causes organ and/or tissue impairment (Smith D, Yong K, *BMJ.* 2013 Jun. 26; 346: f3863). Common clinical manifestations of MM include hypercalcemia, anemia, renal damage, increased susceptibility to bacterial infection, impaired production of normal immunoglobulin, and diffuse osteoporosis (usually in the pelvis, spine, ribs, and skull).

MM is the second most common (10-15% of all) hematological cancer. It is responsible for 15-20% of deaths from hematological cancer and about 2% of all deaths from cancer (Smith D, Yong K, *BMJ.* 2013 Jun. 26; 346:f3863). Despite advances in therapy, MM is still considered an incurable disease (Hsi E, et al., *Clin. Cancer Res.*, May 1, 2008 14; 2775; Hari P, et al., *Bone Marrow Transplant* 2006; 37:1-18; Greipp P., *Semin Hematol* 2005; 42:S16-21; Crane E, List A., *Cancer Invest* 2005; 23:625-34; Gahrton G, et al. *Hematology* 2005; 10 Suppl 1:127-8; Anderson K C., *Semin Hematol* 2005; 42:S3-8). Accordingly, it is an object of the present invention to provide improved methods for treating subjects with MM.

SUMMARY

Provided herein are methods for treating cancer, e.g., a hematological cancer, particularly multiple myeloma (MM), in a human patient, comprising administering to the patient a combination of an anti-KIR antibody and an anti-CS1 antibody. In one embodiment, the MM is smoldering multiple myeloma (e.g., high risk smoldering MM).

An exemplary anti-KIR antibody is lirilumab (also previously referred to as BMS-986015 or IPH2102) comprising the heavy and light chains having the sequences shown in SEQ ID NOs:1 and 2, respectively, or antigen binding fragments and variants thereof. In other embodiments, the antibody comprises the heavy and light chain complementarity determining regions (CDRs) or variable regions (VRs) of lirilumab. Accordingly, in one embodiment, the antibody comprises the CDR1, CDR2, and CDR3 domains of the heavy chain variable (VH) region of lirilumab having the sequence shown in SEQ ID NO:3, and the CDR1, CDR2 and CDR3 domains of the light chain variable (VL) region of LIRILUMAB having the sequence shown in SEQ ID NO:5. In another embodiment, the antibody comprises CDR1, CDR2 and CDR3 heavy chain sequences as set forth in SEQ ID NOs:7, 8, and 9, respectively, and CDR1, CDR2 and CDR3 light chain sequences as set forth in SEQ ID NOs:10, 11, and 12, respectively. In another embodiment, the antibody comprises VH and/or VL regions having the amino acid sequences set forth in SEQ ID NO:3 and/or SEQ ID NO:5, respectively. In another embodiment, the antibody comprises the VH and/or VL regions encoded by the nucleic acid sequences set forth in SEQ ID NO:4 and/or SEQ ID NO:6, respectively. In another embodiment, the antibody competes for binding with, and/or binds to the same epitope on KIR as, the above-mentioned antibodies. In another embodiment, the antibody has at least about 90% variable region amino acid sequence identity with the above-mentioned antibodies (e.g., at least about 90%, 95% or 99% variable region identity with SEQ ID NO:3 or SEQ ID NO:5).

An exemplary anti-CS1 antibody is elotuzumab (also referred to as BMS-901608 or HuLuc63) comprising the CDR1, CDR2, and CDR3 domains of the VH region of elotuzumab having the sequence shown in SEQ ID NO:19, and the CDR1, CDR2 and CDR3 domains of the VL region of elotuzumab having the sequence shown in SEQ ID NO:21. In another embodiment, the antibody comprises the heavy chain CDR1, CDR2 and CDR3 domains having the sequences set forth in SEQ ID NOs:23, 24, and 25, respectively, and the light chain CDR1, CDR2 and CDR3 domains having the sequences set forth in SEQ ID NOs: 26, 27, and 28, respectively. In another embodiment, the antibody comprises VH and/or VL regions having the amino acid sequences set forth in SEQ ID NO: 19 and/or SEQ ID NO:21, respectively. In another embodiment, the antibody competes for binding with, and/or binds to the same epitope on CS1 as, the above-mentioned antibodies. In another embodiment, the antibody has at least about 90% variable region amino acid sequence identity with the above-mentioned antibodies (e.g., at least about 90%, 95% or 99% variable region identity with SEQ ID NO:19 or SEQ ID NO:21).

Accordingly, in one aspect, methods of treating MM in a human patient are provided, the methods comprising administering to the patient an effective amount of each of an anti-KIR and an anti-CS1 antibody.

In another aspect, methods of treating MM in a human patient are provided, the methods comprising administering to the patient an effective amount of each of: (a) an antibody that binds with high affinity and specificity to, and blocks the inhibitory activity of, an inhibitory KIR receptor on a NK cell, and (b) an antibody that binds with high affinity and specificity to CS1 on the surface of a multiple myeloma cell.

In a further aspect, methods of treating MM in a human patient are provided, the methods comprising administering to the patient, an effective amount of each of:

(a) an anti-KIR antibody comprising the CDR1, CDR2 and CDR3 domains in a heavy chain variable region having the sequence set forth in SEQ ID NO:3, and the CDR1, CDR2 and CDR3 domains in a light chain variable region having the sequence set forth in SEQ ID NO:5, and (b) an anti-CS1 antibody comprising the CDR1, CDR2 and CDR3 domains in a heavy chain variable region having the sequence set forth in SEQ ID NO:19, and the CDR1, CDR2 and CDR3 domains in a light chain variable region having the sequence set forth in SEQ ID NO:21.

In another aspect, methods of treating MM in a human patient are provided, the methods comprising administering to the patient, an effective amount of each of:

(a) an anti-KIR antibody comprising the CDR1, CDR2 and CDR3 domains in a heavy chain variable region having the sequence set forth in SEQ ID NO:3, and the CDR1, CDR2 and CDR3 domains in a light chain variable region having the sequence set forth in SEQ ID NO:5, and (b) an anti-CS1 antibody comprising the CDR1, CDR2 and CDR3 domains in a heavy chain variable region having the sequence set forth in SEQ ID NO:19, and the CDR1, CDR2 and CDR3 domains in a light chain variable region having the sequence set forth in SEQ ID NO:21, wherein (A) the anti-CS1 antibody is administered weekly for a total of 8 doses over 8 weeks and the anti-KIR antibody is administered every 4 weeks for a total of 2 doses over 8 weeks during an induction phase, followed by (B) administration of the anti-CS1 antibody every 2 weeks and administration of the anti-KIR antibody every 4 weeks during a maintenance phase, and wherein the anti-KIR antibody is administered at a dose of 0.1-20 mg/kg body weight and the anti-CS1 antibody is administered at a dose of 0.1-20 mg/kg body weight during both the induction and maintenance phases.

In certain embodiments, each dose of the anti-KIR antibody is administered at 0.1, 0.3, 1, 3, 6, 10 or 20 mg/kg. In preferred embodiments, each dose of the anti-KIR antibody is administered at 0.3, 1 or 3 mg/kg. In other embodiments, each dose of the anti-CS1 antibody is administered at 0.1, 0.3, 1, 3, 6, 10 or 20 mg/kg body weight. In a preferred embodiment, each dose of the anti-CS1 antibody is administered at 10 mg/kg.

In one embodiment, the anti-KIR antibody and anti-CS1 antibody are administered at the following doses during either the induction or maintenance phase:

(a) 0.3 mg/kg anti-KIR antibody and 10 mg/kg of anti-CS1 antibody;

(b) 1 mg/kg anti-KIR antibody and 10 mg/kg of anti-CS1 antibody; or (c) 3 mg/kg anti-KIR antibody and 10 mg/kg of anti-CS1 antibody.

Accordingly, in one embodiment, the dose of the anti-KIR and/or anti-CS1 antibody is calculated per mg/kg body weight. However, in another embodiment, the dose of the anti-KIR and/or anti-CS1 antibody is a flat-fixed dose that is fixed irrespective of the weight of the patient. For example, the anti-KIR and/or anti-CS1 antibody may be administered at a fixed dose of 5, 20, 75, 200, 400, 750 or 1500 mg, without regard to the patient's weight. In certain embodiments, dosage regimens are adjusted to provide the optimum desired response (e.g., an effective response).

In one embodiment, the anti-CS1 antibody is administered on (1) day 1, week 1, (2) day 1, week 2, (3), day 1, week 3, (4), day 1, week 4, (5) day 1, week 5, (6) day 1, week 6, (7) day 1, week 7, and (8) day 1, week 8, of the induction phase. In another embodiment, the anti-KIR antibody is administered on (1) day 1, week 1 and (2) day 1, week 5 of the induction phase. In one embodiment, the anti-CS1 antibody is administered on (1) day 1, week 10 and (2) day 1, week 15 of the maintenance phase. In one embodiment, the anti-KIR antibody is administered on day 1, week 10 of the maintenance phase.

In another embodiment, the anti-KIR antibody is administered at a dose and/or frequency to fully saturate the KIR. For example, in one embodiment, the anti-KIR antibody is administered at a dose and a dosing frequency to achieve at least about 90%, preferably at least about 95% KIR occupancy on NK cells in plasma for at least about one, two, three or six months, thereby having sustained saturation for an extended period of time (e.g., at least 3 months, 6 months). In another embodiment, the dose is in the range from about 0.1 to about 3 mg/kg, from about 0.3 to about 3 mg/kg, from about 0.1 to about 1 mg/kg and from about 1 to about 3 mg/kg. The dosing frequency may be in the range of once per day to once per 2 months, from about once per week to about once per 2 months; or about once per month. Alternatively, the dosing frequency can be selected from about three times, about twice, and about once per day; about five times, about four times, about three times, and about twice per week; and about once every two, four, and six weeks.

In another, a dose of anti-KIR antibody resulting in substantially complete receptor saturation (e.g., at least about 90% or 95% receptor occupancy) is administered from about 2 times per week to about once per month, from about 2 times per week to about once per 2 months, or from about once per month to about once per 2 months. The dose can be, e.g., administered at least 3 times, at least 6 times, or more. For example, the method may comprise administering an anti-KIR antibody at a dose and a dosing frequency achieving at least about 90% or 95% KIR occupancy on NK cells for at least about two weeks, one month, 6 months, 9 months or 12 months.

In another embodiment, a regimen results in sustained substantially complete receptor saturation. A dose of anti-KIR antibody resulting in substantially complete receptor saturation for a period of at least about 1 week, 2 weeks or 1 month is administered. When the dose results in substantially complete receptor saturation (e.g., at least about 90% or 95% receptor occupancy) for about one week, the dose may be administered for example between once per week and once every two weeks; when the dose results in substantially complete receptor saturation for about two weeks, the dose may be administered for example between once every two weeks and once per month. When the dose results in substantially complete receptor saturation for about two weeks to about one month, the dose may be administered for example about once per month. In each regimen, the dose can be, e.g., administered at least 3 times, at least 6 times, or more. For example, the method may comprise administering an anti-KIR antibody at a dose and a dosing frequency achieving at least about 95% KIR occupancy on NK cells for at least about 6 months, 9 months or 12 months.

In one embodiment, the anti-CS1 antibody and anti-KIR antibody are administered as a first ("front") line of treatment (e.g., the initial or first treatment). In another embodiment, the anti-CS1 antibody and anti-KIR antibody are administered as a second line of treatment (e.g., after initial treatment with the same or a different therapeutic, including after relapse and/or where the first treatment has failed).

The anti-KIR and anti-CS1 antibodies can be administered to a subject by any suitable means. In one embodiment, the antibodies are formulated for intravenous administration. In another embodiment, the antibodies are administered simultaneously (e.g., in a single formulation or concurrently as separate formulations). Alternatively, in another embodiment, the antibodies are administered sequentially (e.g., as separate formulations).

The efficacy of the treatment methods provided herein can be assessed using any suitable means. In one embodiment, the treatment produces at least one therapeutic effect selected from the group consisting of complete response, very good partial response, partial response, and stable disease. In another embodiment, administration of the anti-KIR and anti-CS1 antibodies has a synergistic effect on treatment compared to administration of either antibody alone. In another embodiment, the combination therapy exhibits therapeutic synergy in a patient having a high tumor burden or advanced stage cancer. In another embodiment, the combination therapy exhibits therapeutic synergy in a patient having one or more tumors (e.g., a solid tumor) that have been infiltrated by NK cells. In a further embodiment, the synergistic anti-tumoral activity is mediated by NK cells. In yet another embodiment, the combination therapy exhibits therapeutic synergy in prolonging survival of the patient.

Also provided are compositions comprising:

(a) an anti-KIR antibody comprising the CDR1, CDR2 and CDR3 domains in a heavy chain variable region having the sequence set forth in SEQ ID NO:3, and the CDR1, CDR2 and CDR3 domains in a light chain variable region having the sequence set forth in SEQ ID NO:5, and (b) an anti-CS1 antibody comprising the CDR1, CDR2 and CDR3 domains in a heavy chain variable region having the sequence set forth in SEQ ID NO:19, and the CDR1, CDR2 and CDR3 domains in a light chain variable region having the sequence set forth in SEQ ID NO:21.

The invention further provides kits that include a pharmaceutical composition containing an anti-KIR antibody, such as lirilumab, and an anti-CS1 antibody, such as elotuzumab, and a pharmaceutically-acceptable carrier, in a therapeutically effective amount adapted for use in the methods described herein. In one embodiment, the kit comprises:

(a) a dose of an anti-KIR antibody comprising the CDR1, CDR2 and CDR3 domains in a heavy chain variable region having the sequence set forth in SEQ ID NO:3, and the CDR1, CDR2 and CDR3 domains in a light chain variable region having the sequence set forth in SEQ ID NO:5;

(b) a dose of an anti-CS1 antibody comprising the CDR1, CDR2 and CDR3 domains in a heavy chain variable region having the sequence set forth in SEQ ID NO:19, and the CDR1, CDR2 and CDR3 domains in a light chain variable region having the sequence set forth in SEQ ID NO:21; and (c) instructions for using the anti-KIR antibody and anti-CS1 antibody in a method of the in the invention.

In another aspect, an anti-KIR antibody is provided, the anti-KIR antibody comprising the CDR1, CDR2 and CDR3 domains in a heavy chain variable region having the sequence set forth in SEQ ID NO:3, and the CDR1, CDR2 and CDR3 domains in a light chain variable region having the sequence set forth in SEQ ID NO:5, for co-administration with an anti-CS1 antibody comprising the CDR1, CDR2 and CDR3 domains in a heavy chain variable region having the sequence set forth in SEQ ID NO:19, and the CDR1, CDR2 and CDR3 domains in a light chain variable region having the sequence set forth in SEQ ID NO:21.

In a further aspect, an anti-KIR antibody is provided, the anti-KIR antibody comprising the CDR1, CDR2 and CDR3 domains in a heavy chain variable region having the sequence set forth in SEQ ID NO:3, and the CDR1, CDR2 and CDR3 domains in a light chain variable region having the sequence set forth in SEQ ID NO:5, for co-administration with an anti-CS1 antibody comprising the CDR1, CDR2 and CDR3 domains in a heavy chain variable region having the sequence set forth in SEQ ID NO:19, and the CDR1, CDR2 and CDR3 domains in a light chain variable region having the sequence set forth in SEQ ID NO:21, wherein (A) the anti-CS1 antibody is administered weekly for a total of 8 doses over 8 weeks and the anti-KIR antibody is administered every 4 weeks for a total of 2 doses over 8 weeks during an induction phase, followed by (B) administration of the anti-CS1 antibody every 2 weeks and administration of the anti-KIR antibody every 4 weeks during a maintenance phase, and wherein the anti-KIR antibody is administered at a dose of 0.1-20 mg/kg body weight and the anti-CS1 antibody is administered at a dose of 0.1-20 mg/kg body weight during both the induction and maintenance phases.

BRIEF DESCRIPTION OF THE DRAWINGS

FIG. 3 provides an example of the gating strategy results (from a volunteer's PBMCs), as assessed by flow cytometry.

FIG. 4 is a table which summarizes the target cell lines and effector cell characteristics in each experiment.

FIG. 5 is a read-out which shows CD107 mobilization on NK cells within PBMCs incubated with U266B1 or with OPM-2.

FIG. 6 is a read-out which shows intracellular TNF-α production in NK cells within PBMCs incubated with U266B1 or with OPM-2.

FIG. 7 is a read out which shows intracellular IFN-γ production in NK cells within PBMCs incubated with U266B1 or with OPM-2.

FIG. 8 is a read out which shows CD107 mobilization, intracellular TNF-α production and intracellular IFN-γ production in NK cells expressing KIR2D in response to U266B1.

FIG. 9 is a read out which shows CD107 mobilization, intracellular TNF-α production and intracellular IFN-γ production in NK cells expressing KIR2D in response to OPM-2.

FIG. 10 is a read out which shows CD107 mobilization on NK cells, within PBMCs incubated with U266B1 or with OPM-2 on healthy volunteers per CD16 genotype (F/F, V/F or V/V).

FIG. 11 is a read out which shows intracellular TNF-α production on NK cells within PBMCs incubated with U266B1 or with OPM-2 on healthy volunteers per CD16 genotype (F/F, V/F or V/V).

FIG. 12 is a read out which shows intracellular IFN-γ production on NK cells within PBMCs incubated with U266B1 or with OPM-2 on healthy volunteers per CD16 genotype (F/F, V/F or V/V).

FIG. 14 is a series of graphs depicting the effect of NK cell depletion on OPM-2 growth in KIRtg-RAG mice (n=10).

FIGS. 16A-C are a series of graphs depicting the anti-tumoral activity of lirilumab (IPH2102) in KIRtg-RAG mice engrafted with 5×10$^6$ OPM-2 SC (n=10).

FIGS. 22A-C are a series of graphs which show the anti-tumoral activity of elotuzumab in KIRtg-RAG mice engrafted with 5×10$^6$ OPM-2 SC.

FIG. 25 is a series of graphs which show the combined activity of elotuzumab and lirilumab (IPH2102) in KIRtg-RAG mice.

FIGS. 28A-D is a series of graphs which show the involvement of NK cells in the combined activity of elotuzumab and lirilumab (IPH2102).

FIG. 31 is a plot which shows the comparison of different treated groups at day 27 post graft.

FIG. 33 is a series of graphs which show the combined activity of elotuzumab and lirilumab (IPH2102) on high tumoral volume.

FIG. 34 are graphs which show the doubling time and tumor growth delay of the different treated groups related to the control (huIgG1+diluent) calculated at 4 predetermined tumor volumes. For the combined group DT was calculated with n=8 mice.

DETAILED DESCRIPTION

I. Definitions

Figure 1:
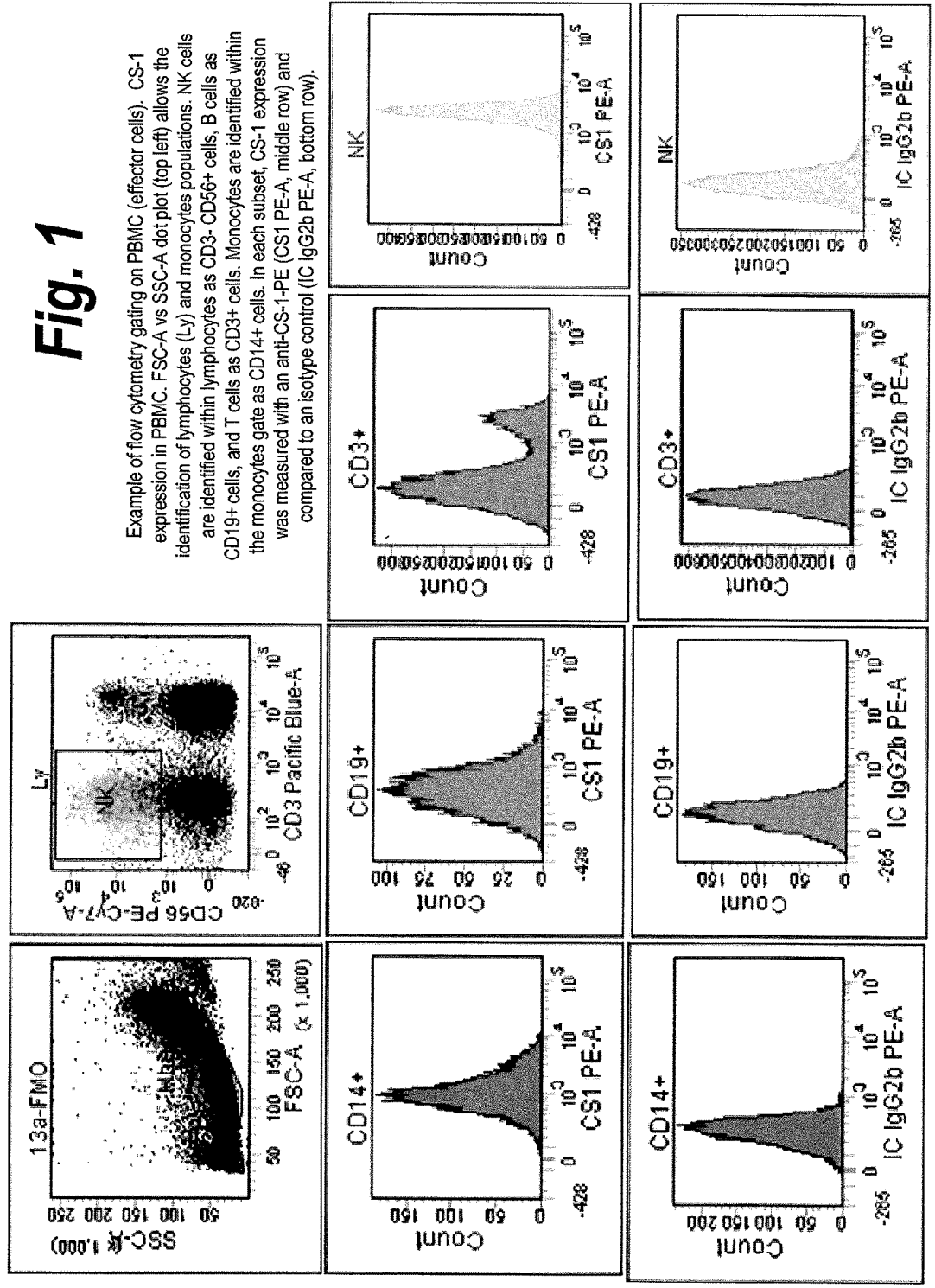
FIG. 1 depicts CS-1 expression in PBMCs, as assessed by flow cytometry gating.

As used herein, the term "subject" or "patient" is a human cancer patient (e.g., a patient having a hematological malignancy, such a MM).

As used herein, "cancer" is a term used for diseases in which abnormal cells divide without control and are able to invade other tissues. Cancers include solid tumors and hematological malignancies.

Solid tumors are neoplasms (new growth of cells) or lesions (damage of anatomic structures or disturbance of physiological functions) formed by an abnormal growth of body tissue cells other than blood, bone marrow or lymphatic cells. A solid tumor consists of an abnormal mass of cells, which may stem from different tissue types such as liver, colon, breast, or lung, and which initially grows in the organ of its cellular origin. However, solid tumors may spread to other organs through metastatic tumor growth in advanced stages of the disease.

Hematological malignancies are cancer types affecting the blood, bone marrow, and lymph nodes. Hematological malignancies can derive from either of the two major blood cell lineages, i.e., myeloid and lymphoid cell lines. The myeloid cell line normally produces granulocytes, erythrocytes, thrombocytes, macrophages, and mast cells, whereas the lymphoid cell line produces B, T, NK and plasma cells. Lymphomas (e.g., Hodgkin's Lymphoma), lymphocytic leukemias, and myeloma are derived from the lymphoid line, while acute and chronic myelogenous leukemia (AML, CML), myelodysplastic syndromes and myeloproliferative diseases are myeloid in origin.

Multiple myeloma (also known as myeloma or plasma cell myeloma) is a hematological cancer formed by malignant plasma cells. Normal plasma cells (also called plasma B cells, plasmocytes, and effector B cells) are a type of white blood cell that are found in the bone marrow and make antibodies. MM is characterized by excessive numbers of abnormal plasma cells in the bone marrow and overproduction of intact monoclonal immunoglobulin (IgG, IgA, IgD, or IgE) or Bence-Jones protein (free monoclonal light chains). MM represents a malignant proliferation of plasma cells derived from a single clone. In MM, neoplastic plasma cells accumulate in the bone marrow and produce a monoclonal protein that causes organ and/or tissue impairment (Smith D, Yong K, *BMJ.* 2013 Jun. 26; 346: f3863). Common clinical manifestations of MM include hypercalcemia, anemia, renal damage, increased susceptibility to bacterial infection, impaired production of normal immunoglobulin, and diffuse osteoporosis (usually in the pelvis, spine, ribs, and skull). In one embodiment, the MM is smoldering MM (e.g., high risk smoldering MM).

MM disease response or progression is typically measured according to the size of reduction (or rise) in paraproteins. As used herein, the term "paraprotein" (also known as "M proteins") refers to an immunoglobulin or immunoglobulin light-chain that is produced in excess by the clonal proliferation of plasma cells. An excess of paraproteins in the blood is known as paraproteinemia. Paraproteins form a narrow band, or 'spike' in protein electrophoresis as they are all exactly the same protein.

Another factor that may be considered in monitoring MM disease response or progression is the degree of "plasmacytosis" in the bone marrow. Plasmacytosis is the presence of large numbers of plasma cells in bone or other tissue where one would not normally expect to encounter them. The existence of soft tissue plasmacytomas (a malignant plasma cell tumor growing within soft tissue) is also considered (Smith D, Yong K, *BMJ.* 2013 Jun. 26; 346: f3863).

As used herein, "effective treatment" refers to treatment producing a beneficial effect, e.g., amelioration of at least one symptom of a disease or disorder. A beneficial effect can take the form of an improvement over baseline, i.e., an improvement over a measurement or observation made prior to initiation of therapy according to the method. A beneficial effect can also take the form of arresting, slowing, retarding, or stabilizing of a deleterious progression of a marker of cancer. Effective treatment may refer to alleviation of at least one symptom of a cancer. Such effective treatment may, e.g., reduce patient pain, reduce the size and/or number of lesions, may reduce or prevent metastasis, and/or may slow tumor growth.

The term "effective amount" refers to an amount of an agent that provides the desired biological, therapeutic, and/or prophylactic result. That result can be reduction, amelioration, palliation, lessening, delaying, and/or alleviation of one or more of the signs, symptoms, or causes of a disease, or any other desired alteration of a biological system. In one example, an "effective amount" is the amount of anti-KIR antibody and the amount of anti-CS1 antibody, in combination, clinically proven to effect a significant decrease in cancer or slowing of progression of cancer, e.g., a hematological cancer, such as MM.

An effective amount can be administered in one or more administrations. The effective amount of the drug or composition may relieve to some extent one or more of the symptoms associated with the cancer.

As used herein, the terms "induction" and "induction phase" are used interchangeably and refer to the first phase of treatment in the clinical trial. For example, during induction, subjects may receive intravenous doses of an anti-KIR antibody in combination with an anti-CS1 antibody.

As used herein, the terms "maintenance" and "maintenance phase" are used interchangeably and refer to the second phase of treatment in the clinical trial. For example, during maintenance, subjects may receive an anti-KIR antibody in combination with an anti-CS1 antibody. In certain embodiments, treatment is continued as long as clinical benefit is observed or until unmanageable toxicity or disease progression occurs.

As used herein, the terms "fixed dose", "flat dose" and "flat-fixed dose" are used interchangeably and refer to a dose that is administered to a patient without regard for the weight or body surface area (BSA) of the patient. The fixed or flat dose is therefore not provided as a mg/kg dose, but rather as an absolute amount of the agent (e.g., the anti-KIR antibody and/or anti-CS1 antibody).

As used herein, a "body surface area (BSA)-based dose" refers to a dose (e.g., of the anti-KIR antibody and/or anti-CS1 antibody) that is adjusted to the body-surface area (BSA) of the individual patient. A BSA-based dose may be provided as mg/kg body weight. Various calculations have been published to arrive at the BSA without direct measurement, the most widely used of which is the Du Bois formula (see Du Bois D, Du Bois E F (June 1916) *Archives of Internal Medicine* 17 (6): 863-71; and Verbraecken, J. et al. (April 2006). *Metabolism—Clinical and Experimental* 55 (4): 515-24). Other exemplary BSA formulas include the Mosteller formula (Mosteller R D. *N Engl J Med.,* 1987; 317:1098), the Haycock formula (Haycock G B, et al., *J*

*Pediatr* 1978, 93:62-66), the Gehan and George formula (Gehan E A, George S L, *Cancer Chemother Rep* 1970, 54:225-235), the Boyd formula (Current, J D (1998), *The Internet Journal of Anesthesiology* 2 (2); and Boyd, Edith (1935), University of Minnesota. The Institute of Child Welfare, Monograph Series, No. x. London: Oxford University Press), the Fujimoto formula (Fujimoto S, et al., Nippon Eiseigaku Zasshi 1968; 5:443-50), the Takahira formula (Fujimoto S, et al., Nippon Eiseigaku Zasshi 1968; 5:443-50), and the Schlich formula (Schlich E, et al., Ernährungs Umschau 2010; 57:178-183).

The term "antibody" describes polypeptides comprising at least one antibody derived antigen binding site (e.g., VH/VL region or Fv, or CDR). Antibodies include known forms of antibodies. For example, the antibody can be a human antibody, a humanized antibody, a bispecific antibody, or a chimeric antibody. The antibody also can be a Fab, Fab'2, ScFv, SMIP, Affibody®, nanobody, or a domain antibody. The antibody also can be of any of the following isotypes: IgG1, IgG2, IgG3, IgG4, IgM, IgA1, IgA2, IgAsec, IgD, and IgE. The antibody may be a naturally occurring antibody or may be an antibody that has been altered (e.g., by mutation, deletion, substitution, conjugation to a non-antibody moiety). For example, an antibody may include one or more variant amino acids (compared to a naturally occurring antibody) which changes a property (e.g., a functional property) of the antibody. For example, numerous such alterations are known in the art which affect, e.g., half-life, effector function, and/or immune responses to the antibody in a patient. The term antibody also includes artificial polypeptide constructs which comprise at least one antibody-derived antigen binding site.

As used herein, a "Killer Ig-like Receptor", "Killer Inhibitory Receptor", or "KIR", refers to a protein or polypeptide encoded by a gene that is a member of the KIR gene family or by a cDNA prepared from such a gene. A detailed review of the KIR gene family, including the nomenclature of KIR genes and KIR gene products, and Genbank accession numbers for exemplary KIRs, is "The KIR Gene Cluster" by M. Carrington and P. Norman, available at the NCBI website called "Bookshelf" (accessible via the World-Wide Web (WWW) address ncbi.nlm.nih.gov/books; see also Campbell et al., *Immunology*, 132(3):315-25; March 2011). The sequences of human KIR genes and cDNAs, as well as their protein products, are available in public databases, including GenBank. Non-limiting exemplary GenBank entries of human KIRs have the following accession numbers: KIR2DL1: Genbank accession number U24076, NM_014218, AAR16197, or L41267; KIR2DL2: Genbank accession number U24075 or L76669; KIR2DL3: Genbank accession number U24074 or L41268; KIR2DL4: Genbank accession number X97229; KIR2DS1: Genbank accession number X89892; KIR2DS2: Genbank accession number L76667; KIR2DS3: Genbank accession number NM_012312 or L76670 (splice variant); KIR3DL1: Genbank accession number L41269; and KIR2DS4: Genbank accession number AAR26325. A KIR may comprise from 1 to 3 extracellular domains, and may have a long (i.e., more than 40 amino acids) or short (i.e., less than 40 amino acids) cytoplasmic tail. As previously described herein, these features determine the nomenclature of a KIR. Exemplary KIR2DL1, KIR2DL2, KIR2DL3, and KIR2DS4 molecules comprise polypeptides having the following respective amino acid sequences:

```
KIR2DL1 extracellular domain:
                                         (SEQ ID NO: 13)
HEGVHRKPSLLAHPGXLVKSEETVILQCWSDVMFEHFLLHREGMFNDTLR

LIGEHHDGVSKANFSISRMTQDLAGTYRCYGSVTHSPYQVSAPSDPLDIV

IIGLYEKPSLSAQXGPTVLAGENVTLSCSSRSSYDMYHLSREGEAHERRL

PAGPKVNGTFQADFPLGPATHGGTYRCFGSFHDSPYEWSKSSDPLLVSVT

GNPSNSWPSPTEPSSKTGNPRHLH, where "X" at position 16 is P or R, and where "X" at position 114 is P or

L, representing allelic variants.

KIR2DL2 extracellular domain:
                                         (SEQ ID NO: 14)
HEGVHRKPSLLAHPGRLVKSEETVILQCWSDVRFEHFLLHREGKFKDTLH

LIGEHHDGVSKANFSIGPMMQDLAGTYRCYGSVTHSPYQLSAPSDPLDIV

ITGLYEKPSLSAQPGPTVLAGESVTLSCSSRSSYDMYHLSREGEAHECRF

SAGPKVNGTFQADFPLGPATHGGTYRCFGSFRDSPYEWSNSSDPLLVSVI

GNPSNSWPSPTEPSSKTGNPRHLH

KIR2DL3 extracellular domain:
                                         (SEQ ID NO: 15)
HEGVHRKPSLLAHPGPLVKSEETVILQCWSDVRFQHFLLHREGKFKDTLH

LIGEHHDGVSKANFSIGPMMQDLAGTYRCYGSVTHSPYQLSAPSDPLDIV

ITGLYEKPSLSAQPGPTVLAGESVTLSCSSRSSYDMYHLSREGEAHERRF

SAGPKVNGTFQADFPLGPATHGGTYRCFGSFRDSPYEWSNSSDPLLVSVT

GNPSNSWPSPTEPSSETGNPRHLH

KIR2DS4 extracellular domain:
                                         (SEQ ID NO: 16)
QEGVHRKPSFLALPGHLVKSEETVILQCWSDVMFEHFLLHREGKFNNTLH

LIGEHHDGVSKANFSIGPMMPVLAGTYRCYGSVPHSPYQLSAPSDPLDMV
```

The term "KIR2DL2/3" refers to either or both of the KIR2DL2 and KIR2DL3 receptors. These two receptors have a very high homology, are encoded by allelic forms of the same gene, and are considered by the art to be functionally similar.

As used herein, the terms CS1, SLAMF7, SLAM Family Member 7, CD2 Subset, CRACC, CD2-Like Receptor-Activating Cytotoxic Cells, 19A24 Protein, 19A, CD2-Like Receptor Activating Cytotoxic Cells, CD319, Novel LY9 (Lymphocyte Antigen 9) Like Protein, Membrane Protein FOAP-12, CD319 Antigen, Protein 19A, APEX-1, FOAP12, and Novel Ly93 are used interchangeably, and include variants, isoforms, species homologs of human CS1, and analogs having at least one common epitope with CS1.

CS1 is a cell surface glycoprotein that is highly expressed on MM cells. CS1 is characterized by two extracellular immunoglobulin (Ig)-like domains and an intracellular signaling domain with immune receptor tyrosine-based switch motifs (Yu-Tzu Tai, et al., *Blood*. 2009 Apr. 30; 113(18): 4309-4318; Bhat R, et al., *J Leukoc Biol*. 2006; 79:417-424; Fischer A, et al., *Curr Opin Immunol*. 2007; 19:348-353; Boles K S, et al., *Immunogenetics*. 2001; 52:302-307; Lee J K, et al., *J Immunol*. 2007; 179:4672-4678; and Veillette A., *Immunol Rev*. 2006; 214:22-34). CS1 is expressed at high levels in normal and malignant plasma cells, but not normal organs, solid tumors, or $CD34^+$ stem cells. Only a small subset of resting lymphocytes, including NK cells and a subset of $CD8^+$ T cells, express detectable but low levels of CS1 (Hsi E D, et al., *Clin. Cancer Res.* 2008; 14:2775-2784 and Murphy J J, et al., *Biochem J.* 2002; 361:431-436).

CS1 was isolated and cloned by Boles et al. (*Immunogenetics.* 2001; 52(3-4):302-7). The complete CS1 sequence can be found under GenBank Accession No.: NM_021181.3 and is as follows:

(SEQ ID NO: 29)
MAGSPTCLTLIYILWQLTGSAASGPVKELVGSVGGAVTFPLKSKVKQVDS

IVWTFNTTPLVTIQPEGGTIIVTQNRNRERVDFPDGGYSLKLSKLKKNDS

GIYYVGIYSSSLQQPSTQEYVLHVYEHLSKPKVTMGLQSNKNGTCVTNLT

CCMEHGEEDVIYTWKALGQAANESHNGSILPISWRWGESDMTFICVARNP

VSRNFSSPILARKLCEGAADDPDSSMVLLCLLLVPLLLSLFVLGLFLWFL

KRERQEEYIEEKKRVDICRETPNICPHSGENTEYDTIPHTNRTILKEDPA

NTVYSTVEIPKKMENPHSLLTMPDTPRLFAYENV

IIa. Anti-KIR Antibodies

Anti-human-KIR antibodies (or VH/VL domains derived therefrom) suitable for use in the invention can be generated using methods well known in the art. Alternatively, art recognized anti-KIR antibodies can be used. In preferred embodiments, the anti-KIR antibody is cross-reactive with multiple inhibitory KIR receptors and potentiates the cytotoxicity of NK cells bearing one or more of these receptors. For example, the anti-KIR antibody may bind to each of KIR2D2DL1, KIR2DL2, and KIR2DL3, and potentiate NK cell activity by reducing, neutralizing and/or reversing inhibition of NK cell cytotoxicity mediated by any or all of these KIRs. In further embodiments, the anti-KIR antibody does not bind KIR2DS4 and/or KIR2DS3. For example, monoclonal antibodies 1-7F9 (also known as IPH2101), 14F1, 1-6F1 and 1-6F5, described in WO 2006/003179, the teachings of which are hereby incorporated by reference, can be used. Antibodies that compete with any of these art-recognized antibodies for binding to KIR also can be used. Additional art-recognized anti-KIR antibodies which can be used include, for example, those disclosed in WO 2005/003168, WO 2005/009465, WO 2006/072625, WO 2006/072626, WO 2007/042573, WO 2008/084106, WO 2010/065939, WO 2012/071411 and WO/2012/160448.

An exemplary anti-KIR antibody is lirilumab comprising heavy and light chains having the sequences shown in SEQ ID NOs:1 and 2, respectively, or antigen binding fragments and variants thereof. Lirilumab is also referred to as BMS-986015, IPH2102, or in WO 2008/084106 as 1-7F9(S241P), and the terms "lirilumab," "IPH2102" and "BMS-986015" are used interchangeable herein. Lirilumab is a fully human anti-KIR antibody that comprises the same heavy and light chain variable regions as 1-7F9 (described in WO 2006/003179; also known as IPH2101), and thus binds to the same epitope as 1-7F9, but differs from 1-7F9 in that (1) it is prepared in Chinese hamster ovary (CHO) cells, whereas 1-7F9 is prepared from hybridoma cells, and (2) a stabilizing hinge mutation (S231P) has been introduced into lirilumab (WO 2008/084106).

In other embodiments, the antibody comprises the heavy and light chain CDRs or variable regions of lirilumab. Accordingly, in one embodiment, the antibody comprises the CDR1, CDR2, and CDR3 domains of the VH region of lirilumab having the sequence set forth in SEQ ID NO:3, and the CDR1, CDR2 and CDR3 domains of the VL region of lirilumab having the sequence set forth in SEQ ID NO:5. In another embodiment, the antibody comprises heavy chain CDR1, CDR2 and CDR3 domains having the sequences set forth in SEQ ID NOs:7, 8, and 9, respectively, and light chain CDR1, CDR2 and CDR3 domains having the sequences set forth in SEQ ID NOs:10, 11, and 12, respectively. In another embodiment, the antibody comprises VH and/or VL regions having the amino acid sequences set forth in SEQ ID NO:3 and/or SEQ ID NO: 5, respectively. In another embodiment, the antibody comprises the heavy chain variable (VH) and/or light chain variable (VL) regions encoded by the nucleic acid sequences set forth in SEQ ID NO:4 and/or SEQ ID NO:6, respectively. In another embodiment, the antibody competes for binding with, and/or binds to the same epitope on KIR as, the above-mentioned antibodies. In another embodiment, the antibody has at least about 90% variable region amino acid sequence identity with the above-mentioned antibodies (e.g., at least about 90%, 95% or 99% variable region identity with SEQ ID NO:3 or SEQ ID NO:5).

IIb. Anti-CS1 Antibodies

Anti-human-CS1 antibodies (or VH and/or VL domains derived therefrom) suitable for use in the invention can be generated using methods well known in the art. Alternatively, art recognized anti-CS1 antibodies can be used. For example, the monoclonal antibody mAb 162 described in Bouchon et al., *J. Immunol.*, 167:5517-5521 (2001) can be used, the teachings of which are hereby incorporated by reference herein in their entirety, and in particular, those portions directly related to this antibody. Another known CS1 antibody includes the anti-CS1 antibody described in Matthew et al, (U.S. Pat. No. 7,041,499), the teachings of which are hereby incorporated by reference herein in their entirety, and in particular, those portions directly related to this antibody. Other known CS1 antibodies include the anti-CS1 antibody, Luc 63 and other antibodies that share the same epitope, including Luc 4, Luc 12, Luc 23, Luc 29, Luc 32 and Luc 37, the anti-CS1 antibody Luc 90 and other antibodies that share the same epitope, including Luc 34, Luc 69 and Luc X, and the anti-CS1 antibodies Luc2, Luc3, Luc15, Luc22, Luc35, Luc38, Luc39, Luc56, Luc60, LucX.1, LucX.2, and PDL-241, described in Williams et al, (U.S. Pat. No. 7,709,610), the teachings of which are hereby incorporated by reference herein in their entirety, and in particular, those portions directly related to these antibodies. Antibodies that compete with any of these art-recognized antibodies for binding to CS1 also can be used.

An exemplary anti-CS1 antibody is elotuzumab (also referred to as BMS-901608 or HuLuc63) comprising heavy and light chains having the sequences shown in SEQ ID NOs:17 and 18, respectively, or antigen binding fragments and variants thereof. Elotuzumab is a humanized IgG1 anti-CS-1 monoclonal antibody described in WO2004/100898, WO2005/10238, WO2008/019376, WO2008/019378, WO2008/019379, WO2010/051391, WO2011/053321, and WO2011/053322, the teachings of which are hereby incorporated by reference. Elotuzumab is known to mediate ADCC through NK cells (van Rhee, F., et al., 2009; *Mol. Cancer Ther.*, 8(9): 2616-24).

In other embodiments, the antibody comprises the heavy and light chain CDRs or variable regions of elotuzumab. Accordingly, in one embodiment, the antibody comprises the CDR1, CDR2, and CDR3 domains of the VH of elotuzumab having the sequence set forth in SEQ ID NO:19, and the CDR1, CDR2 and CDR3 domains of the VL of elotuzumab having the sequences set forth in SEQ ID NO:21. In another embodiment, the antibody comprises heavy chain CDR1, CDR2 and CDR3 domains having the sequences set forth in SEQ ID NOs:23, 24, and 25, respectively, and light chain CDR1, CDR2 and CDR3 domains having the sequences set forth in SEQ ID NOs:26, 27, and 28, respectively. In another embodiment, the antibody comprises VH and/or VL regions having the amino acid sequences set forth in SEQ ID NO: 19 and/or SEQ ID NO: 21, respectively. In another embodiment, the antibody competes for binding with, and/or binds to the same epitope on CS1 as, the above-mentioned antibodies. In another embodiment, the antibody has at least about 90% variable region amino acid sequence identity with the above-mentioned antibodies (e.g., at least about 90%, 95% or 99% variable region identity with SEQ ID NO:19 or SEQ ID NO:21).

III. Compositions

Provided herein are compositions comprising an anti-KIR antibody and an anti-CS1 antibody. In one embodiment, the composition comprises (a) an anti-KIR antibody comprising the CDR1, CDR2 and CDR3 domains in a heavy chain variable region having the sequence set forth in SEQ ID NO:3, and the CDR1, CDR2 and CDR3 domains in a light chain variable region having the sequence set forth in SEQ ID NO:5, and (b) an anti-CS1 antibody comprising the CDR1, CDR2 and CDR3 domains in a heavy chain variable region having the sequence set forth in SEQ ID NO:19, and the CDR1, CDR2 and CDR3 domains in a light chain variable region having the sequence set forth in SEQ ID NO:21.

Compositions suitable for administration to human patients are typically formulated for parenteral administration, e.g., in a liquid carrier, or suitable for reconstitution into liquid solution or suspension for intravenous administration.

In general, such compositions typically comprise a pharmaceutically acceptable carrier. As used herein, the term "pharmaceutically acceptable" means approved by a government regulatory agency or listed in the U.S. Pharmacopeia or another generally recognized pharmacopeia for use in animals, particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil, glycerol polyethylene glycol ricinoleate, and the like. Water or aqueous solution saline and aqueous dextrose and glycerol solutions may be employed as carriers, particularly for injectable solutions (e.g., comprising an anti-KIR or anti-CS1 antibody). Liquid compositions for parenteral administration can be formulated for administration by injection or continuous infusion. Routes of administration by injection or infusion include intravenous, intraperitoneal, intramuscular, intrathecal and subcutaneous. In one embodiment, the anti-KIR and/or anti-CS1 antibodies are administered intravenously (e.g., separately or together, each, e.g., over the course of one hour, 90 minutes, or two hours).

IV. Patient Populations

Provided herein are effective methods for treating cancer (e.g., a hematological cancer) in a human patient using a combination of an anti-KIR antibody and an anti-CS1 antibody. In a particular embodiment, the human patient suffers from multiple myeloma.

V. Combination Therapy

Combination therapies provided herein involve administration of an anti-KIR antibody and an anti-CS1 antibody, to treat subjects afflicted with cancer (e.g., a hematological cancer). In one embodiment, the invention provides an anti-KIR antibody and an anti-CS1 antibody in combination to treat subjects having MM. In a particular embodiment, the anti-KIR antibody is lirilumab. In another embodiment, the anti-CS1 antibody is elotuzumab.

As used herein, adjunctive or combined administration (coadministration) includes simultaneous administration of the compounds in the same or different dosage form, or separate administration of the compounds (e.g., sequential administration). Thus, the anti-KIR and anti-CS1 antibodies can be simultaneously administered in a single formulation. Alternatively, the anti-KIR and anti-CS1 antibodies can be formulated for separate administration and are administered concurrently or sequentially.

For example, the anti-CS1 antibody can be administered first followed by (e.g., immediately followed by) the administration of the anti-KIR antibody, or vice versa. Such concurrent or sequential administration preferably results in both antibodies being simultaneously present in treated patients.

VI. Treatment Protocols

In one aspect, methods of treating MM in a human patient are provided, the methods comprising administering to the patient an effective amount of each of an anti-KIR and an anti-CS1 antibody.

In another aspect, methods of treating MM in a human patient are provided, the methods comprising administering to the patient an effective amount of each of: (a) an antibody that binds with high affinity and specificity to, and blocks the inhibitory activity of, an inhibitory KIR receptor on a NK cell, and (b) an antibody that binds with high affinity and specificity to CS1 on the surface of a multiple myeloma cell.

Suitable treatment protocols for treating a human patient afflicted with MM include, for example, administering to the patient an effective amount of each of:

(a) an anti-KIR antibody comprising the CDR1, CDR2 and CDR3 domains in a heavy chain variable region having the sequence set forth in SEQ ID NO:3, and the CDR1, CDR2 and CDR3 domains in a light chain variable region having the sequence set forth in SEQ ID NO:5, (b) an anti-CS1 antibody comprising the CDR1, CDR2 and CDR3 domains in a heavy chain variable region having the sequence set forth in SEQ ID NO:19, and the CDR1, CDR2 and CDR3 domains in a light chain variable region having the sequence set forth in SEQ ID NO:21.

In another aspect, methods of treating MM in a human patient are provided, the methods comprising administering to the patient, an effective amount of each of:

(a) an anti-KIR antibody comprising the CDR1, CDR2 and CDR3 domains in a heavy chain variable region having the sequence set forth in SEQ ID NO:3, and the CDR1, CDR2 and CDR3 domains in a light chain variable region having the sequence set forth in SEQ ID NO:5, and (b) an anti-CS1 antibody comprising the CDR1, CDR2 and CDR3 domains in a heavy chain variable region having the sequence set forth in SEQ ID NO:19, and the CDR1, CDR2 and CDR3 domains in a light chain variable region having the sequence set forth in SEQ ID NO:21, wherein (A) the anti-CS1 antibody is administered weekly for a total of 8 doses over 8 weeks and the anti-KIR antibody is administered every 4 weeks for a total of 2 doses over 8 weeks during an induction phase, followed by (B) administration of the anti-CS1 antibody every 2 weeks and administration of the anti-KIR antibody every 4 weeks during a maintenance phase, and wherein the anti-KIR antibody is administered at a dose of 0.1-20 mg/kg body weight and the anti-CS1 antibody is administered at a dose of 0.1-20 mg/kg body weight during both the induction and maintenance phases.

In certain embodiments, each dose of the anti-KIR antibody is administered at 0.1, 0.3, 1, 3, 6, 10 or 20 mg/kg. In preferred embodiments, each dose of the anti-KIR antibody is administered at 0.3, 1 or 3 mg/kg.

In other embodiments, each dose of the anti-CS1 antibody is administered at 0.1, 0.3, 1, 3, 6, 10 or 20 mg/kg body weight. In a preferred embodiment, each dose of the anti-CS1 antibody is administered at 10 mg/kg.

In one embodiment, the anti-KIR antibody and anti-CS1 antibody are administered at the following doses during either the induction or maintenance phase:

(a) 0.3 mg/kg anti-KIR antibody and 10 mg/kg of anti-CS1 antibody;

(b) 1 mg/kg anti-KIR antibody and 10 mg/kg of anti-CS1 antibody; or (c) 3 mg/kg anti-KIR antibody and 10 mg/kg of anti-CS1 antibody.

In another embodiment, the dose of the anti-KIR and/or anti-CS1 antibody is varied over time. For example, the anti-KIR antibody and/or anti-CS1 antibody may be initially administered at a high dose and may be lowered over time. In another embodiment, the anti-KIR antibody and/or anti-CS1 antibody is initially administered at a low dose and increased over time.

In another embodiment, the amount of the anti-KIR and/or anti-CS1 antibodies administered is constant for each dose. In another embodiment, the amount of antibody administered varies with each dose. For example, the maintenance (or follow-on) dose of the antibody can be higher or the same as the loading dose which is first administered. In another embodiment, the maintenance dose of the antibody can be lower or the same as the loading dose.

In one embodiment, the anti-CS1 antibody is administered on (1) day 1, week 1, (2) day 1, week 2, (3), day 1, week 3, (4), day 1, week 4, (5) day 1, week 5, (6) day 1, week 6, (7) day 1, week 7, and (8) day 1, week 8, of the induction phase. In another embodiment, the anti-KIR antibody is administered on (1) day 1, week 1 and (2) day 1, week 5 of the induction phase. In another embodiment, the anti-CS1 antibody is administered on (1) day 1, week 10 and (2) day 1, week 15 of the maintenance phase. In another embodiment, the anti-KIR antibody is administered on day 1, week 10 of the maintenance phase.

In another embodiment, 8 doses of the anti-CS1 antibody are administered per eight week cycle during the induction phase. In another embodiment, 2 doses of the anti-KIR antibody are administered per eight week cycle during the induction phase.

In other embodiments, the anti-KIR and/or anti-CS1 antibodies are administered once per week, once every two or three weeks, once per month for as long as a clinical benefit is observed or until there is a complete response, confirmed progressive disease or unmanageable toxicity.

In another embodiment, the anti-CS1 antibody and anti-KIR antibody are administered as a first line of treatment (e.g., the initial or first treatment). In another embodiment, the anti-CS1 antibody and anti-KIR antibody are administered as a second line of treatment (e.g., after the initial or first treatment, including after relapse and/or where the first treatment has failed).

In another embodiment, the dose of the anti-KIR antibody is selected to provide substantially complete saturation in human patients. As used herein, the term "substantially complete saturation" of "full saturation" refers to at least 90% occupancy of the targeted KIR and preferably at least 95% receptor occupancy. The method optionally includes assessing the patient for NK cell potentiation and/or anti-tumor activity (which may be performed by use of any suitable technique, several of which being known in the art, including, e.g., KIR occupancy level, CD107a marker, etc., as described herein).

For example, an anti-KIR antibody is administered at a dose and a dosing frequency achieving at least about 90%, preferably at least about 95% KIR occupancy on NK cells in plasma for at least about one, two, three or six months, thereby having sustained saturation for an extended period of time (e.g., at least 3 months, 6 months). In another embodiment, the dose is in the range from about 0.1 to about 3 mg/kg, from about 0.3 to about 3 mg/kg, from about 0.1 to about 1 mg/kg and from about 1 to about 3 mg/kg. The dosing frequency is in the range of once per day to once per 2 months, from about once per week to about once per 2 months; or about once per month. Alternatively, the dosing frequency is selected from about three times, about twice, and about once per day; about five times, about four times, about three times, and about twice per week; and about once every two, four, and six weeks.

In one preferred embodiment, a dose of anti-KIR antibody resulting in substantially complete receptor saturation (e.g., at least about 90% or 95% receptor occupancy) is administered from about 2 times per week to about once per month, from about 2 times per week to about once per 2 months, or from about once per month to about once per 2 months. The dose can be, e.g., administered at least 3 times, at least 6 times, or more. For example, the method may comprise administering an anti-KIR antibody at a dose and a dosing frequency achieving at least about 90% or 95% KIR occupancy on NK cells for at least about two weeks, one month, 6 months, 9 months or 12 months.

In another embodiment, a regimen results in sustained substantially complete receptor saturation. A dose of anti-KIR antibody resulting in substantially complete receptor saturation for a period of at least about 1 week, 2 weeks or 1 month is administered. When the dose results in substantially complete receptor saturation (e.g., at least about 90% or 95% receptor occupancy) for about one week, the dose may be administered for example between once per week and once every two weeks; when the dose results in substantially complete receptor saturation for about two weeks, the dose may be administered for example between once every two weeks and once per month. When the dose results in substantially complete receptor saturation for about two weeks to about one month, the dose may be administered for example about once per month. In each regimen, the dose can be, e.g., administered at least 3 times, at least 6 times, or more. For example, the method may comprise administering an anti-KIR antibody at a dose and a dosing frequency achieving at least about 95% KIR occupancy on NK cells for at least about 6 months, 9 months or 12 months.

VII. Outcomes

Provided herein are methods for treating MM in a patient comprising administering to the patient an anti-CS1 antibody and an anti-KIR antibody. Preferably, the combination therapy exhibits therapeutic synergy. "Therapeutic synergy" refers to a phenomenon where treatment of patients with a combination of therapeutic agents manifests a therapeutically superior outcome to the outcome achieved by each individual constituent of the combination used at its optimum dose (T. H. Corbett et al., 1982, *Cancer Treatment Reports*, 66, 1187). For example, a therapeutically superior outcome is one in which the patients either a) exhibit fewer incidences of adverse events while receiving a therapeutic benefit that is equal to or greater than that where individual constituents of the combination are each administered as monotherapy at the same dose as in the combination, or b) do not exhibit dose-limiting toxicities while receiving a therapeutic benefit that is greater than that of treatment with each individual constituent of the combination when each constituent is administered at the same doses in the combination(s) as is administered as individual components.

Accordingly, in one embodiment, administration of the anti-KIR and anti-CS1 antibodies has a synergistic effect on treatment compared to administration of either antibody alone. In one embodiment, the combination therapy exhibits therapeutic synergy in a patient having a high tumor burden or advanced stage cancer. In another embodiment, the combination therapy exhibits therapeutic synergy in a patient having one or more tumors (e.g., a solid tumor) that have been infiltrated by NK cells. In a further embodiment, the combination therapy exhibits a synergistic anti-tumoral activity that is mediated by NK cells. In yet another embodiment, the combination therapy exhibits therapeutic synergy in prolonging survival of the patient.

Alternatively, the combination therapy of an anti-CS1 antibody and an anti-KIR antibody may have an additive or superadditive effect on suppressing MM, as compared to monotherapy with either antibody alone. By "additive" is meant a result that is greater in extent than the best separate result achieved by monotherapy with each individual component, while "superadditive" is used to indicate a result that exceeds in extent the sum of such separate results. In one embodiment, the additive effect is measured as, e.g., reduction in paraproteins, reduction of plasmacytosis, reduction of bone lesions over time, increase in overall response rate, or increase in median or overall survival.

MM disease response or progression, in particular, is typically measured according to the size of reduction (or rise) in paraproteins. However, the degree of plasmacytosis in the bone marrow (increase in percentage of plasma cells in the bone marrow), progression of bone lesions, and the existence of soft tissue plasmacytomas (malignant plasma cell tumors growing within soft tissue) are also considered (Smith D, Yong K, *BMJ*. 2013 Jun. 26; 346: f3863). Responses to therapy may include:
Complete Response
No detectable paraprotein and disappearance of any soft tissue plasmacytomas and <5% plasma cells in bone marrow.
Very Good Partial Response
Greater than 90% reduction in paraproteins or paraproteins detectable but too low to measure.
Partial Response
Greater than 50% reduction in paraproteins.
No Change or Stable Disease
Not meeting criteria for disease response or progression.
Progressive Disease
At least a 25% increase in paraproteins (increase of at least 5 g/L), development of new bone lesions or plasmacytomas, or hypercalcemia.
(corrected serum calcium >2.65 mmol/L)

Patients treated according to the methods disclosed herein preferably experience improvement in at least one sign of MM. In one embodiment, the patient treated exhibits a complete response (CR), a very good partial response (VGPR), a partial response (PR), or stable disease (SD).

In one embodiment, improvement is measured by a reduction in paraprotein and/or decrease or disappearance of soft tissue plasmacytomas. In another embodiment, lesions can be measured by radiography. In another embodiment, cytology or histology can be used to evaluate responsiveness to a therapy.

In other embodiments, administration of effective amounts of the anti-KIR antibody and anti-CS1 antibody according to any of the methods provided herein produces at least one therapeutic effect selected from the group consisting of reduction in paraprotein, decrease or disappearance of soft tissue plasmacytomas, CR, VGPR, PR, or SD. In still other embodiments, the methods of treatment produce a comparable clinical benefit rate (CBR=CR+PR+SD≥6 months) better than that achieved by an anti-KIR antibody or anti-CS1 antibody alone. In other embodiments, the improvement of clinical benefit rate is about 20% 20%, 30%, 40%, 50%, 60%, 70%, 80% or more compared to an anti-KIR antibody or anti-CS1 antibody alone.

VIII. Kits and Unit Dosage Forms

Also provided herein are kits which include a pharmaceutical composition containing an anti-KIR antibody, such as lirilumab, and an anti-CS1 antibody, such as elotuzumab, and a pharmaceutically-acceptable carrier, in a therapeutically effective amount adapted for use in the preceding methods. The kits optionally also can include instructions, e.g., comprising administration schedules, to allow a practitioner (e.g., a physician, nurse, or patient) to administer the composition contained therein to administer the composition to a patient having MM. The kit also can include a syringe.

Optionally, the kits include multiple packages of the single-dose pharmaceutical compositions each containing an effective amount of the anti-KIR or anti-CS1 antibody for a single administration in accordance with the methods provided above. Instruments or devices necessary for administering the pharmaceutical composition(s) also may be included in the kits. For instance, a kit may provide one or more pre-filled syringes containing an amount of the anti-KIR or anti-CS1 antibody.

In one embodiment, the present invention provides a kit for treating MM in a human patient, the kit comprising:
(a) a dose of an anti-KIR antibody comprising the CDR1, CDR2 and CDR3 domains in a heavy chain variable region having the sequence set forth in SEQ ID NO:3, and the CDR1, CDR2 and CDR3 domains in a light chain variable region having the sequence set forth in SEQ ID NO:5;
(b) a dose of an anti-CS1 antibody comprising the CDR1, CDR2 and CDR3 domains in a heavy chain variable region having the sequence set forth in SEQ ID NO:19, and the CDR1, CDR2 and CDR3 domains in a light chain variable region having the sequence set forth in SEQ ID NO:21; and
(c) instructions for using the anti-KIR antibody and anti-CS1 antibody in the methods described herein.

The following examples are merely illustrative and should not be construed as limiting the scope of this disclosure in any way as many variations and equivalents will become apparent to those skilled in the art upon reading the present disclosure.

The contents of all references, Genbank entries, patents and published patent applications cited throughout this application are expressly incorporated herein by reference.

EXAMPLES

Example 1

In Vitro Studies—Combination of Elotuzumab and Lirilumab

In vitro studies were performed to determine the effect of a combination of various doses of elotuzumab and lirilumab on the activation of primary NK cells by MM cell lines. Studies were also performed to assess whether the CD16 genotype or HLA-C genotype of an individual is predictive of NK cell responses. A summary of the materials and methods used in these experiments is set forth below.

Materials and Methods
Products

CD16 Genotyping by PCR

The Two FcγRIIIA allotypes (V158 or F158) result from a single-nucleotide polymorphism (SNP) from the FCGR3A gene. FcγRIIIA-158 V/F polymorphism is associated with an efficacy of treatments by monoclonal antibodies involving ADCC. CD16 genotyping by PCR was performed according to the technique described by Leppers-van de Straat, F. G., et al. (*J. Immunol Methods*, 2000. 242(1-2): p. 127-32).

HLA-C Genotyping by qPCR

HLA-C genotyping was performed according to the protocol described by Schellekens, J., et al. (*Tissue Antigens*, 2007. 69(4): p. 334-7). A mix was prepared for each C1 or C2 allele groups in a final volume of 250 with the following reagents: 12.50 SYBR® green (kit Biorad), 250 pmol primers Reverse C1 or C2, 250 pmol primer Forward and 0.5 µg DNA. Samples were amplified and quantified according to the following program: 10 min at 95° C. following 45 cycles of 15 s at 95° C. and 1 min at 60° C. The following primers were used:

| Specificity | Conjuguate | Clone | Supplier | Volume (FACS) |
|---|---|---|---|---|
| CD107a | APC | H4A3 | Becton Dickinson Cat No. 641581 | 5 µl/test |
| CD107b | Alexa647 | H4B4 | ebioscience Cat No. 51-1078-42 | 5 µl/test |
| IFN-γ | PerCp-Cy5.5 | 4S.B3 | ebioscience Cat No. 45-7319 | 5 µl/test |
| TNF-α | PE | Mab11 | Becton Dickinson Cat No. 554513 | 10 µl/test |
| elotuzumab (25 mg/ml) | Not applicable | Not applicable | BMS Batch No. 1B68974 expired on May 2012 | Not applicable |
| IPH2102 (10 mg/ml) | Not applicable | Not applicable | Innate pharma Batch No. IPH2102-01C-01 LIRILUMAB | Not applicable |
| anti-CS-1 | PE | Not applicable | ebioscience Cat No. 12-2229 | 5 µl/test |
| CD3 | pacific blue | SP34-2 | Becton Dickinson Cat No. 558124 | 3 µl/test |
| CD56 | PE-Cy7 | HCD56 | Biolegend Cat No. BLE318318 | 5 µl/test |
| Human IgG4 | FITC | HP6025 | Southern Biotech Cat No. 9200-09 | 1.66 µl/test |
| HLA-ABC | FITC | B9.12.1 | Beckman Coulter Cat No. IM1838U | 5 µl/test |
| CD14 | APC | RMO52 | Beckman Coulter Cat No. IM2580 | 5 µl/test |
| CD19 | FITC | J4.119 | Beckman Coulter Cat No. AO7768 | 5 µl/test |
| CD16 | PE | 3G8 | Beckman Coulter Cat No. AO7766 | 10 µl/test |
| CD16 | PE | MEM 154 | Santa Cruz Cat No. 51525 | 20 µl/test |
| CD158b1/b2/j (2DL3/2DL2/2DS2) | PE | GL183 | Beckman Coulter Cat No. IM2278U | 5 µl/test |
| CD158a (2DL1) | PE | 143211 | RD Systems Cat No. FAB1844P | 5 µl/test |

Medium according to MOT-0246
RPMI 1640 (Gibco # 31870)
Sodium Pyruvate (Gibco #11360) 1 mM
MEM Non Essential AminoAcids (Gibco #11140) 1%
L-Glutamine (Gibco #25030) 2 mM
Penicillin Streptomycin (Gibco#15070) 1%
Fetal Bovine Serum (PAN #3302-batch P231002) 10%
FACS Staining Buffer (PBS 1x, 0.2% BSA, 0.02% NaN$_3$, EDTA 2 mM)
Phosphate Buffer Saline (PBS) 10 x (Gibco Invitrogen, ref: 14200-067).
"MilliQ" Water
Bovine Serum Albumine (BSA) (Sigma, ref: A-9418).
Sodium azide stock solution NaN$_3$ 20% (p/v) in PBS (NaN$_3$ Prolabo, ref 27967.150)
EDTA (Invitrogen 0.5M ref: 155775038).

```
Generic Forward Primer
                                    (SEQ ID NO: 30)
5'-TATTGGGACCGGGAGACACA-3'

HLA-C Group 1 Reverse Primer
                                    (SEQ ID NO: 31)
5'-CGCAGGTTCCGCAGGC-3'

HLA-C Group 2 Reverse Primer
                                    (SEQ ID NO: 32)
5'-GCGCAGTTTCCGCAGGT-3'
```

Cell Lines (Target Cells)

Two MM cell lines expressing CS-1 and MHC class I (OPM-2 and U266B1) were used for NK cell stimulation. U266 B1 cells were obtained from ATCC (ref # TIB-196). OPM-2 cells were obtained from DSMZ (ref # ACC50). HLA-C typing was performed on these two cell lines:

|  | HLA-C Typing |
|---|---|
| OPM2 | C1/C2 |
| U266B1 | C1/C1 |

Cells were counted and passed every two days in complete medium. Viability was measured and had to be over 80%. The cells were kept in culture up to 10 passages (P10). On the day of the experiment, cells were counted and adjusted to 100,000 cells/wells. CS-1 and HLA-ABC expression were analyzed on target cell lines in each experiment.

PBMCs (Effector Cells)

Figure 2:
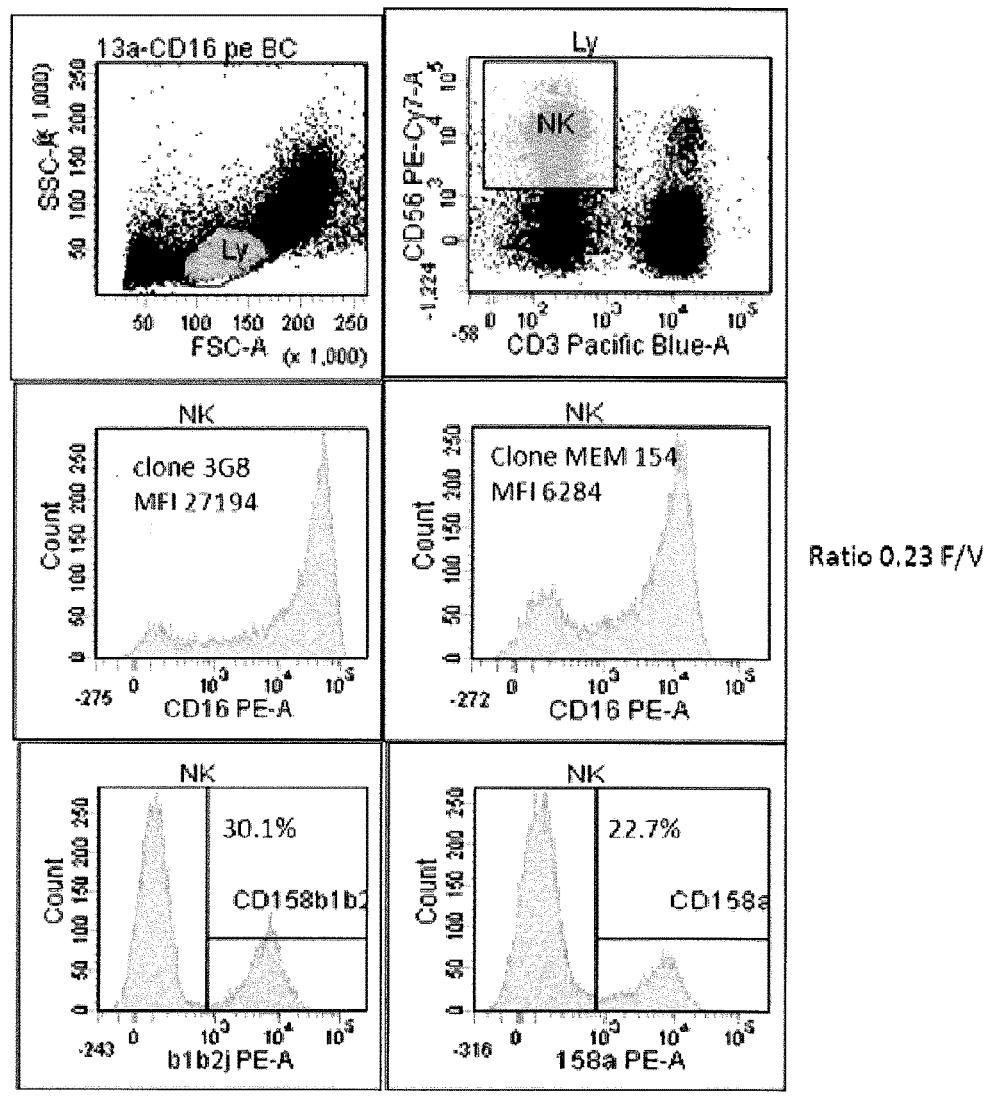
FIG. 2 depicts the characterization of NK cells within PBMCs, as assessed by flow cytometry gating.

PBMCs isolated from healthy volunteers whole blood (origin: Etablissement Français du Sang, (EFS), Marseille) were used as effectors cells. Frozen PBMCs (available from Innate Pharma) were analysed by PCR to determine their CD16 genotype (i.e., F/V heterozygous, F/F homozygous or V/V homozygous). During the course of the present study, 21 additional donors were screened in order to find enough healthy volunteers with V/V genotype. In parallel, CD16 expression on PBMCs was assessed by flow cytometry to confirm the PCR results. Four samples of PBMCs from each CD16 genotype described above were selected. On the day of the experiment, PBMCs were thawed and incubated for one hour at 37° C. to discard apoptotic cells. Viability was measured (with Malassez in trypan blue) and had to be over 80% (i.e., experiments were not performed were viability was below 80%). Cells were counted and adjusted to 250,000 cells/wells. CS-1 expression was measured on effector lines, CD14$^+$ cells, CD19$^+$ cells, and NK cells (CD3$^-$ CD56$^+$ gating) (FIG. 1). KIR expression (CD158b1/b2/j; CD158a) was measured on NK cells (FIG. 2).

In Vitro Functional Assay

NK cells function was assessed using a CD107 mobilization assay coupled with intracytoplasmic staining for TNF-α, and IFN-γ. The ratio of effectors cells to targets cells was 2.5/1. Concentrations were determined using dose ranges of elotuzumab and lirilumab. Increasing concentrations of elotuzumab and lirilumab (0 µg/mL, 0.025 µg/mL, 0.5 µg/mL and 10 µg/mL) were used in combination to detect a combined effect of both antibodies.

Gating Strategy in Functional Assay

In each experiment, FACS data was analyzed as follows. First, a gate on the lymphocytes was made (FIG. 3, left quadrant top line). Then NK cells were identified as CD3$^-$ CD56$^+$ lymphocytes (FIG. 3, middle quadrant top line) and NK cells were divided between NK cells that stained positively with lirilumab (Anti-KIR$^+$ on NK, FIG. 3, right quadrant top line) and NK cells that did not stain with lirilumab (Anti-KIR$^-$ on NK, FIG. 3, right quadrant top line). Cells that stained positively for CD107, TNF-α, and IFN-γ on total NK, lirilumab positive NK cells, and lirilumab negative NK cells were identified (FIG. 3).

Statistics

To detect outliers in a set of values, a Grubb's test was performed using www.graphpad.com/quickcalcs/grubbs1/. One-way ANOVA was performed when indicated using Graphpad Prism software. Due to the low number of sample (n=12), a Gaussian distribution was assumed. Variance equality was tested with a Bartlett's test as a condition for the use of the ANOVA. Bonferroni multiple comparison test was applied post-ANOVA in order to compare each group. *=p<0.05, =p<0.01, *=p<0.001

Results

HLA Class I and CS-1 Expression

In each experiment, expression of HLA class I (HLA-C is the ligand for KIR2D targeted by lirilumab) and CS-1 (targeted by elotuzumab) was measured on the MM target cell lines, U266B1 and OPM-2. For both markers in each experiment, a ratio of the mean intensity of fluorescence (MFI) between the specific staining and the background staining was calculated (FIG. 3). This control was performed to detect major changes in phenotype of the target cell lines over the duration of the study. A 2-3-fold variation in these ratios was detected from experiment to experiment, reflecting the expected biological variation due to cell culture. To detect unexpected variations, a Grubb's test to detect outliers was performed. On the target cell lines, only one value was unexpectedly high: the CS-1 ratio on U266B1 in experiment 15 on donor "DSV217" (outlined value in 2). In this experiment CS-1 is expressed at a higher density on U266B1 than in the other experiments. Overall, OPM-2 expresses more CS-1 and less HLA class I than U266B1 (FIG. 4). In parallel, the percentages of NK cells present in each donor's PBMCs, as well as the percentage of NK cells expressing KIR2D molecules (targeted by lirilumab) was measured (FIG. 4). As for target cells, a Grubb's test to detect outliers was performed. No outlier values were detected and the observed variations reflect inter-individual variations in the human population.

The surface expression of CD16 was also measured by flow cytometry with the anti-CD16 clone 3G8 antibody. This clone recognizes both V158 and F158 isoforms of CD16. As for the expression of CS-1, a ratio of the mean intensity of fluorescence (MFI) between the specific staining and the background staining was calculated (FIG. 4) and no outliers were detected using the Grubb's test.

Activation of NK Cells by Combination of Elotuzumab and Lirilumab

Three read-outs were measured on NK cells at the end of a 4-hour incubation of the PBMCs from 12 healthy volunteers, with or without MM cell lines (U266B1 or OPM-2). These three read-outs represent the mobilization of CD107 at the cell surface of NK cells and the intracellular production of IFN-γ and TNF-α, cytokines. Overall, results were similar with the three read-outs (FIGS. 5-7).

The open (white) boxes on FIGS. 5-7 represent the response of NK cells in presence of increasing doses of elotuzumab with the indicated stimulation. There is an increase in the responses (either CD107, IFN-γ or TNF-α), which is dose-dependent. The functional response induced by elotuzumab always increased with increasing doses of lirilumab added to NK cells expressing KIR2D molecules ("KIR2D$^+$ NK cells" in FIGS. 5-7). This increase in NK cell response induced by lirilumab is observed even at a high concentration of elotuzumab (up to 10 µg/mL). The beneficial effect of lirilumab is seen from the first concentration used in the assay (0.025 µg/mL) with a moderate dose-response effect, indicating that lirilumab is probably already partly saturating KIR at 0.025 µg/mL.

In contrast, on NK cells not expressing KIR2D molecules (which are not targeted by lirilumab), the effect of elotuzumab is not increased, thereby demonstrating the specificity of lirilumab ("KIR2D⁻ NK cells" in FIGS. 5-7).

The best combinational effect of elotuzumab and lirilumab was seen on U266B1 with the CD107 TNF-α and IFN-γ read-outs on NK expressing KIR2D (FIG. 7). On U266B1 cells, the significant effect of adding lirilumab was seen on TNF-α, production at all doses of elotuzumab (FIG. 8). However, the significant effect of lirilumab was partly masked by concentrations above 0.5 µg/mL of elotuzumab for the IFN-γ production. In addition, above 0.025 µg/mL of elotuzumab, the significant effect of lirilumab on the CD107 mobilization was masked (FIG. 8). On OPM-2 cells, there is a non-significant trend towards a benefit of adding lirilumab to elotuzumab (FIG. 9). U266B1 cells express moderate levels of CS-1 compared to OPM-2 cells, indicating that in patients with low CS-1 expression, lirilumab treatment could greatly increase the therapeutic effect of elotuzumab.

When PBMCs are incubated without MM cell lines, a basal NK cell activation is detected with increasing doses of elotuzumab (FIGS. 5-7). This probably reflects the recognition of endogenous CS-1 (expressed at low levels on autologous NK cells, CD8⁺ T cells, activated monocytes and DC present within PBMCs) by NK cells (Hsi, E. D., et al., 2009, *Clin. Cancer Res.*, 14(9): p. 2775-84). In the experimental settings used, lirilumab also induced some activation of NK cells expressing KIR. In a larger study including 40 healthy volunteers using a similar in vitro assay, it was demonstrated that this basal activation induced by lirilumab is a combination of crosslinking KIR2DS activating receptors and of recognition of autologous stressed cells (data not shown). This level of in vitro activation is induced by the experimental protocol used on PBMCs and has no consequences in physiological conditions as demonstrated by the safety observed in clinical trials using lirilumab or IPH2101.

No clear effect of CD16 genotype could be demonstrated in this study. Results are presented in FIGS. 10-12. This is probably due to the heterogeneity of CD16 surface expression between healthy volunteers and to the low number of volunteers included. In addition, in vitro assays may not be appropriate to demonstrate an effect of CD16 genotype observed in clinical trials (Cartron, G., et al., 2002, *Blood*, 99(3): p. 754-8). Indeed, it was demonstrated that at optimal doses of rituximab, the in vitro lysis of CD20⁺ target cells is not affected by CD16 genotype and the effect of the genotype is moderate at sub-saturating doses of rituximab (Congy-Jolivet, N., et al., 2008, *Cancer Res.*, 68(4): p. 976-80 and Dall'Ozzo, S., et al., *Cancer Res.*, 2004. 64(13): p. 4664-9).

Conclusion

NK cell activation by CS-1 and HLA-C positive MM cell lines (OPM-2 and U266B1) in the presence of increasing doses of elotuzumab and/or lirilumab was assessed by three read-outs (CD107 mobilization on NK cells surface and intracellular production of the cytokines IFN-γ and TNF-α) as discussed above. Based on these studies, it was determined that NK cell responses to MM cell lines in the presence of elotuzumab or lirilumab are dose-dependent.

Additionally, the functional response induced by elotuzumab was consistently enhanced by adding increasing doses of lirilumab on NK cells expressing KIR2D molecules (targeted by lirilumab). As expected, the effect of elotuzumab was not modified on NK cells not expressing KIR2D molecules. The significant effect of lirilumab was more pronounced with the U266B1 cell line as compared to OPM-2 and some read-outs, such as CD107 mobilization and IFN-γ production were masked with a high dose of elotuzumab (>0.5 µg/mL).

The best combinational effect was seen in response to tumor cells (U266B1) expressing a low density of CS-1 and on NK expressing KIR2D, suggesting that in patients with low CS-1 expression, lirilumab treatment could greatly increase the therapeutic effect of elotuzumab. A clear effect of the CD16 genotype or of the HLA-C genotype on the NK cell responses was not detected.

Example 2

In Vivo Studies—Combination of Elotuzumab and Lirilumab

In vivo studies were performed to assess whether lirilumab could enhance the ADCC activity of elotuzumab in a MM xenograft model in KIRtg-RAG mice.

Materials and Methods

Mice

Transgenic CD158b×RAG-1KO mice (also known as KIR2DL3tg RAG⁻/⁻ or KIRtg-RAG; Cambiaggi et al., 1997, *Proc. Natl. Acad. Sci.* 94:8088-8092) were outbred at Innate Pharma animal facilities or Charles River facilities (L'Arbresle, France). They were fed and housed under sterilized conditions and had a specific and opportunistic pathogen free health status. After an acclimatization period of two weeks, animals were identified by toe ink tattoos prior to enter in experimentation. For experiments, animals were randomized according to their sex and age.

Compounds

Elotuzumab powder (humanized IgG₁ anti-CS1 monoclonal antibody), batch 1B68974 (Expiry Date: May 2012) was resuspended at 25 mg/ml in sterile deionized water and frozen in 200 µl aliquots at −15-25° C. On the day of injection, stock solution was thawed and resupended in 0.9% NaCl solution at the desired concentration.

NaCl solution 0.9%, Versol.

Human IgG₁ isotype control. An anti-Diphtheria toxin human IgG1 monoclonal antibody (clone 1D12-g1f), batch PC-DT- from BMS, at the concentration of 5.3 mg/ml. Stored at a temperature from +2 to +8° C. On the day of injection, it was diluted in PBS 1× at the desired concentration.

Human anti-KIR2DL1/L2/L3/S1/S2 human IgG4, lirilumab (IPH2102), batch IPH2102-01b-01 (Expiry Date: 22 Apr. 2012) at the initial concentration of 10 mg/ml. Stored at 4° C.

IPH2102 Diluent (IPH2102-DIL001): 2.17 mg/ml Na₂HPO₄ dihydrate, 1.22 mg/ml NaH₂PO₄ dihydrate, 75.31 mg/ml Saccharose, 0.01 mg/ml Tween 80. Stored at a temperature from +2 to +8° C.

Phosphate-Buffered Saline 1× Solution, Gibco. Reference: 14190.

Anti-NK1.1 (PK136 clone, mouse IgG₂ₐ) Batch 3 C=4.52 mg/mL (Innate Pharma production). Stored at 4° C.

Administration

Elotuzumab and its isotype control were injected intraperitoneally (IP) using a 1 ml syringe connected to 30 G1/2 needle. Lirilumab and its diluent were injected intra-venously in the caudal vein (IV) (needle 30 G1/2 connected to 1 ml syringe). The injected volumes of solutions listed above were adjusted to the body weight of each animal. Solutions were prepared in a way to inject 10 ml/kg, i.e. one mouse of 20 g received 200 µl of solution. Anti-NK1.1 administration (100 µg/100 µl/mouse, whatever its body weight) was performed intra-venously into caudal vein with 1 ml syringe connected to 30 G1/2 needle.

Cells

OPM-2 (from DSMZ, ref # ACC50) and U266-B1 (from ATCC, ref # TIB-196) are CS1 and Class-I positive human MM cell lines. These cells were characterized in Example 1 and their HLA-C typing are C1/C2 and C1/C1 respectively for OPM2 and U266-B1.

Cell Culturing Conditions

Cells were cultured in RPMI medium (Gibco) supplemented with 10% of decomplemented Fetal Bovine Serum (FBS), 1× of non-essential amino acids (Gibco, reference 11140-035), 2 mM L-Glutamine (Gibco, reference 25030-024), 1 mM Sodium Pyruvate (Gibco, 1136-039). When cells were thawed, they were re-suspended in complete medium at $3\times10^5$ cells/ml. Cells were cultured maximally for three weeks after thawing and were seeded three times a weeks at $3\times10^5$ cells/ml on Mondays and Wednesdays and at $2\times10^5$ cells/ml on Fridays.

Cell Graft Preparation of cells suspension in matrigel was performed. Briefly, cell suspension was injected SC in the flack of mice. BD Matrigel™ Basement Membrane Matrix, 5 ml *LDEV-Free #356234 (BD Biosciences). BD Matrigel™ Basement Membrane Matrix, 10 ml *LDEV-Free #354234 (BD Biosciences).

On the day of cell engraftment, the level of expression of HLA class I and CS-1 on the surface of OPM-2 ($2\times10^5$ cells/point) was determined by flow cytometry with anti-human HLA-ABC and anti-CS-1, respectively.

Tumor Cytometry Analysis

The expression of surface markers on the surface of tumor cells and tumor infiltrating NK cells were characterized (at several time points after cells engraftment) according to the following procedure. Briefly, tumors were withdrawn and mechanically dissociated in RPMI medium. Cells suspensions were centrifuged (2 min at 400 g at room temperature) and the pellets were resuspended in staining buffer (PBS 1×+1 mM EDTA+0.2% bovine serum albumin+0.02% sodium azide). These cell suspensions were stained by flow cytometry to determine if (1) NK KIR+ cells infiltrated tumors and (2) to check that tumor cells still expressed CS-1 and HLA ABC (molecules implicated in elotuzumab efficiency and NK recognition, respectively).

On days 14, 21, 33 and 42, tumor cells were separated based on FSC/SSC parameters and after exclusion of murine lymphocytes with anti-mouse CD45 mAb. The expression of HLA-ABC and CS1 on the surface of tumor cells was then analyzed by flow cytometry using respectively anti-human HLA ABC mAb and anti-human CS-1 mAb.

On days 14 and 21, tumor infiltrating NK cells were identified (NK1.1+CD45+) by the staining with anti-mouse NK-1.1 mAb and anti-mouse CD45 mAb.

On days 33 and 42, the expression of KIR2DL3 receptors on tumor infiltrating NK cells (NK1.1+CD45+) using IPH21-02 PE mAb was also analyzed.

Flow cytometry acquisition was performed on FACS CANTO II and analyzed with FACS DIVA.

Parameters

Body weights were recorded every week and tumor volumes were measured. Briefly length (A) and width (B) were measured using a digital caliper twice/week. Tumor volume was calculated as follows: $(A\times(B)^2/2)$. When the tumor volumes reached 2000 mm$^3$, mice were euthanized and considered dead on the day of sacrifice for the purpose of preparing a survival curve.

The anti-tumor activity of the different treatments was assessed using an anti-tumor parameters calculation. Briefly, exponential growth fit was extrapolated from individual tumor growth curves using GraphPad Prism V5 software and allowed calculation of tumor growth inhibition (TGI), tumor growth delay (TGD) and doubling time (DT).

Tumor growth delay (TGD) is the delay of a treated group to reach a selected volume compared to the control: TGD=T−C. T=median time (days) required for the treatment group tumors to reach a predetermined size. C=median time (days) required for the control group tumors to reach the same size.

Tumor growth inhibition (TGI) is the percentage of inhibition of growth compared to the control: TGI=(1−T/C)× 100. T=median size (tumor volume) for the treatment group tumors reached at a predetermined day. C=median size (tumor volume) for the treatment group tumors reached at the same day.

Doubling Time (Td, DT) is the time required for doubling the volume of the tumor.

When a treatment had a strong anti-tumoral activity, the exponential growth fit could not be extrapolated, avoiding the calculation of anti-tumoral parameters. The cut-off criteria is for $R^2$ of fit <0.7 for at least 2 mice out of 10 animals/group, anti-tumoral parameters were not calculated. In this case, anti-tumoral activity was evaluated mainly using the tumor growth curves profile.

For each group, the number of partial regression (PR), complete regression (CR) and temporary complete regression (TCR) was evaluated. A tumor free mouse is mouse in which a tumor has not grown.

PR is defined by two consecutive reductions of the tumor volume from a selected volume. To be significant and different from the intra-individual measure variations, each reduction has to be more than 17% from the previous measure.

CR is defined by a tumor volume that reaches 0 and is maintained to 0 until the end of study. TCR is defined by a tumor volume that reaches 0 at least once and starts again to grow.

Kaplan Meier survival curves were assessed on the basis of the first day tumor volumes above 2000 mm$^3$ was recorded. The survival medians were calculated with GraphPad Prism software. % ILS (Increase Life Span) was cal-

TABLE 1

List of Fluorochrome Linked Reagents for Flow Cytometry Analysis

| Specificity | Conjugate | Isotype | Supplier | Volume (FACS) |
| --- | --- | --- | --- | --- |
| Anti-hHLA-ABC | APC | mIgG1 | Becton Dickinson, ref: 555555 | 20 µl/point |
| Anti-CS-1 | PE | mIgG2a | Ebioscience, ref: 12-2229-73 | 20 µl/point |
| Anti-mouse CD45 | APC-eFluor 780 | RIgG2b | Ebioscience, Ref: 47-0451-82 | 1 µg/ml |
| Anti-mouse NK-1.1 | APC | mIgG2a | BD Pharmingen 550627 | 0.5 µg/ml |
| IPH2102 | PE | hIgG4 | Innate-Pharma Peak2 | 1 µg/ml |
| 7-AAD | PerCpCyn5.5 | | Pharmingen, ref 559925 | 1/100 final | culated according the formula: % ILS=100×(T−C)/C, wherein T is the median survival of treated group and C is the median survival of control group.

Survival curves were compared using the Log-rank (Mantel-Cox) test with GraphPad Prism software. Data were considered significantly different and noted * when p<0.05 or ** when p<0.01. A comparison of different groups at a determined day was performed as follows:

Analysis of the Gaussian distribution by a normality test.

If the normality test is passed, a one-way ANOVA analysis of variance was performed followed by a post-test If the normality test is not passed, a Kruskal-Wallis non-parametric test was applied followed by a Dunn's multiple comparison.

Results

Screen of MM Cell Lines for Tumoral Model

This first experiment was designed to determine the best in vivo tumor model to evaluate the combined effect of the anti-CS1 monoclonal antibody, elotuzumab, and the anti-KIR monoclonal antibody, lirilumab. For this, two MM cell lines, OPM-2 and U266B1, both expressing HLA-cw3 and CS1, were selected. In this study, it was demonstrated that OPM-2 expressed a higher level of CS-1 than U266-B1 and less Class-I than U266B1. Briefly, OPM-2 and U266B1 were engrafted either subcutaneously with matrigel or intravenously with a high concentration of cells according to the experimental design shown in Table 2.

TABLE 2

Experimental Design

| | | | | Randomization | |
|---|---|---|---|---|---|
| Exp. N° | Groups | Treatment | n = | Mean volume | Day |
| 1 | 20 · 10$^6$ OPM-2 cells/mouse IV | NA | 6 | NA | NA |
| | 20 · 10$^6$ OPM-2 cells/mouse SC matrigel | NA | 6 | | |
| | 20 · 10$^6$ U266B1 cells/mouse SC matrigel | NA | 5 | | | n = number of mice;
NA = Not Applicable

20×10$^6$ of U266B1 cells did not induce subcutaneous tumors, whereas the same concentration of OPM-2 cells did. The fact that U266-B1 cells expressed higher levels of Class-I than OPM-2 cells could explain why they were rejected more in KIRtg-RAG mice than OPM-2 cells. When OPM-2 cells were engrafted at the same concentration, they did not induce mortality, even up to 45 days. In view of these results, OPM-2 subcutaneously engrafted in KIRtg-RAG mice was selected for the following studies.

Determination of Optimal Number of OPM-2 Cells

This experiment was designed to determine the optimal number of cells to engraft subcutaneously, to obtain the more homogeneous tumor growth. Increasing numbers of OPM-2 cells in matrigel were engrafted in KIRtg-RAG mice as shown in Table 3.

TABLE 3

Experimental Design

| | | | | Randomization | |
|---|---|---|---|---|---|
| Exp. N° | Groups | Treatment | n = | Mean volume | Day |
| 2 | 5 · 10$^6$ OPM-2 cells/mouse SC matrigel | NA | 8 | NA | NA |
| | 10 · 10$^6$ OPM-2 cells/mouse SC matrigel | NA | 8 | | |
| | 15 · 10$^6$ OPM-2 cells/mouse SC matrigel | NA | 8 | | | n = number of mice;
NA = Not Applicable

Figure 13:
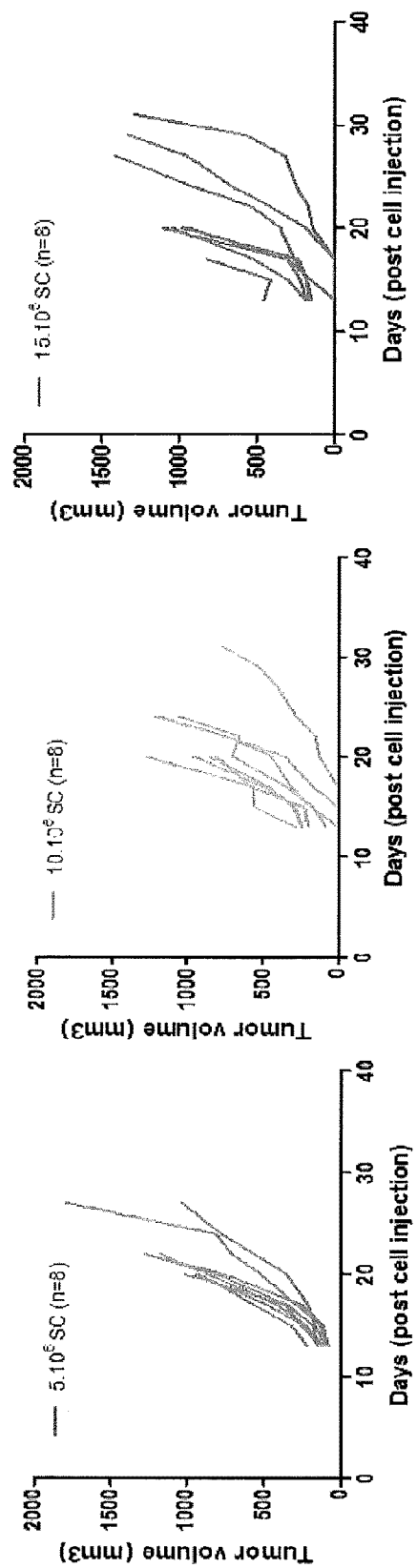
FIG. 13 is a series of graphs depicting cell dependent growth of OPM-2 SC engrafted in KIRtg-Rag mice (individual curves).

The tumoral growth was not related to the number of cells engrafted. Indeed, while the mean curve growth for each amount of tumor cells was similar, the only difference was in the variability of the growth. Specifically, the higher the cell number, the higher the tumor growth variability (FIG. 13). The growth homogeneity was best when using 5×10$^6$ OPM-2 cells. Accordingly, this number of OPM-2 cells was selected for all the following experiments.

Evaluation of NK Involvement in OPM-2 Growth Control

In order to characterize the OPM-2 tumor model, it was important to determine how NK cells modulate OPM-2 growth. OPM-2 cells were engrafted 24 hours after the injection of anti-NK1.1 mAb, a mAb known to deplete NK cells in the blood and spleen. Control animals received phosphate-buffered saline (PBS) instead of anti-NK1.1 mAb and were engrafted as shown in Table 4.

TABLE 4

Experimental Design

| | | | | Randomization | |
|---|---|---|---|---|---|
| Exp. N° | Groups | Treatment | n = | Mean volume | Day |
| 8 | PBS | D-1, D13, D27 | 10 | No random | |
| | anti-NK1.1 100 µg IV + PBS | D-1, D13, D27 | 10 | | | n = number of mice

Figure 15:
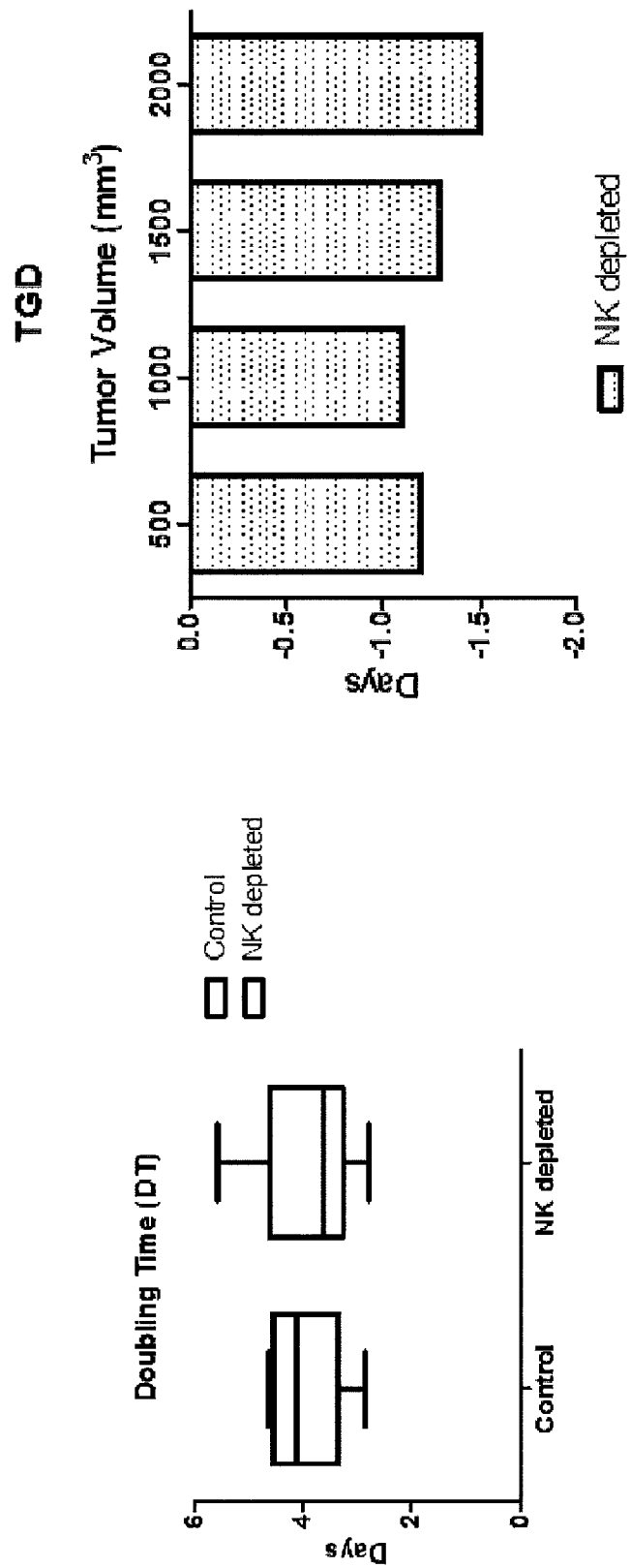
FIG. 15 shows the results of an experiment designed to evaluate NK cell involvement in OPM-2 growth control. The right panel is a graph showing the doubling time (DT) of control and NK cell depleted group (n=10) and the left panel is a graph showing tumor growth delay (TGD) of NK cell-depleted group related to control group calculated at 4 different tumor volumes.

A comparison of the two groups at different time points did not reveal any statistically significant differences between groups (FIG. 14). However, even if not statistically different, the NK depleted group had a tumor doubling time lower than the control one (respectively 3.6±0.9 vs. 4.1±0.7 days), indicating that the tumor grew faster in the NK cell-depleted group. In the same manner, at the different volumes recorded, NK cell depleted animals presented a negative tumor growth delay (TGD) compared to the control, indicating again, that the tumors in NK cell-depleted animals grew a little bit faster (FIG. 15). This study demonstrated a tendency (not significant) of OPM-2 growth control by NK cells.

Saturation Response of Lirilumab (IPH2102)

In order to assess the effects of lirilumab and elotuzumab in combination, it was necessary to (1) determine if lirilumab has anti-tumoral activity alone and (2) to determine the optimal dose of lirilumab to combine with elotuzumab.

A previous pharmacodynamy study evaluated the long duration of KIR saturation related to the dose of lirilumab in KIRtg-RAG mice without tumors. A dose of 15 mg/kg IV saturated the KIR (>95% KIR occupancy) for 18 days (432 hours) (data not shown). The first experiment to test lirilumab involved injecting it at the dose of 15 mg/kg every two weeks three times in order to fully saturate the KIR for more than 50 days (condition noted "full saturation" or "full sat"). It was previously demonstrated that anti-KIR had a greater anti-tumoral efficacy when the concentration of lirilumab is above the concentration that saturated KIR receptors (see Sola C, et al., *PNAS.* 2009; 106: 12879-12884). As a consequence, in the second experiment, lirilumab was injected every week for 5 weeks, still at the dose of 15 mg/kg IV, to reach a concentration above the concentration that saturates the KIR receptors (condition noted "over saturation" or "over sat").

TABLE 5

Experimental Design

| Exp. N° | Groups | Treatment | n = | Mean volume | Day |
|---|---|---|---|---|---|
| 3 | PBS | D13, 20, 27, 34, 41 | 10 | 61.7 ± 24.3 | 13 |
| | IPH2102 (full sat) 15 mg/kg IV every two weeks | D13, 27, 41 | 10 | 60.5 ± 23.7 | |
| | IPH2102 (over sat) 15 mg/kg IV once a week | D13, 20, 27, 34, 41 | 10 | 60.3 ± 23.7 | | n = number of mice

Lirilumab had significant anti-tumoral activity when injected in either full KIR saturation conditions or in "oversaturation" conditions. More than two mice in each treated group presented a complete regression of the tumor, avoiding the calculation of anti-tumoral parameters (i.e., TGD, DT). The analysis of curve profile did not demonstrate a significant difference between the two treatment groups. In both groups, 3 animals had a complete tumor regression. In the full saturation group there was also a temporary complete regression, and in the "oversaturation" group there was also a partial regression (FIGS. 16A-C).

Figure 17:
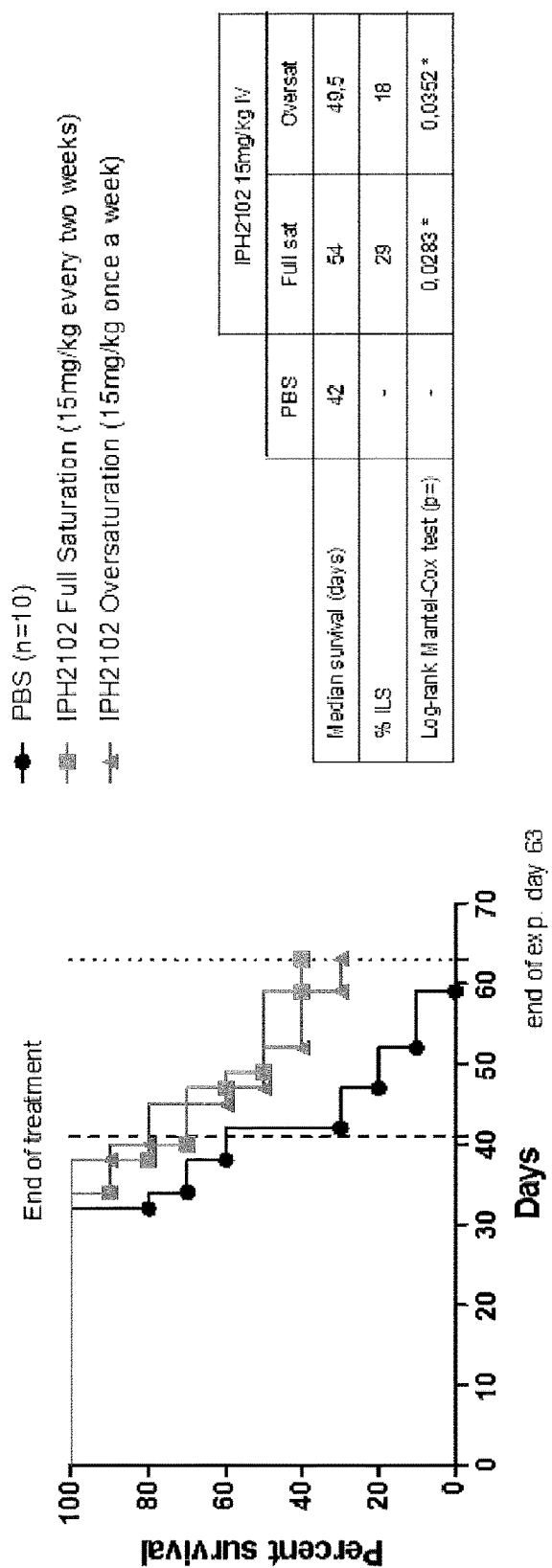
FIG. 17 is a graph showing the efficacy of lirilumab on the survival of KIRtg-RAG mice engrafted with 5×10$^6$ OPM-2 SC (n=10).

In the same way, survival curve analysis did not shown a strong difference between treatments. However, in the full saturation group, lirilumab induced a greater increase of life span of 29% compared to 18% for the oversaturation group (FIG. 17). This difference must be taken with caution, as an analysis of the profile curves highlights a difference between the two curves only at 50% of survival (the point used as reference for median survival calculation).

Figure 18:
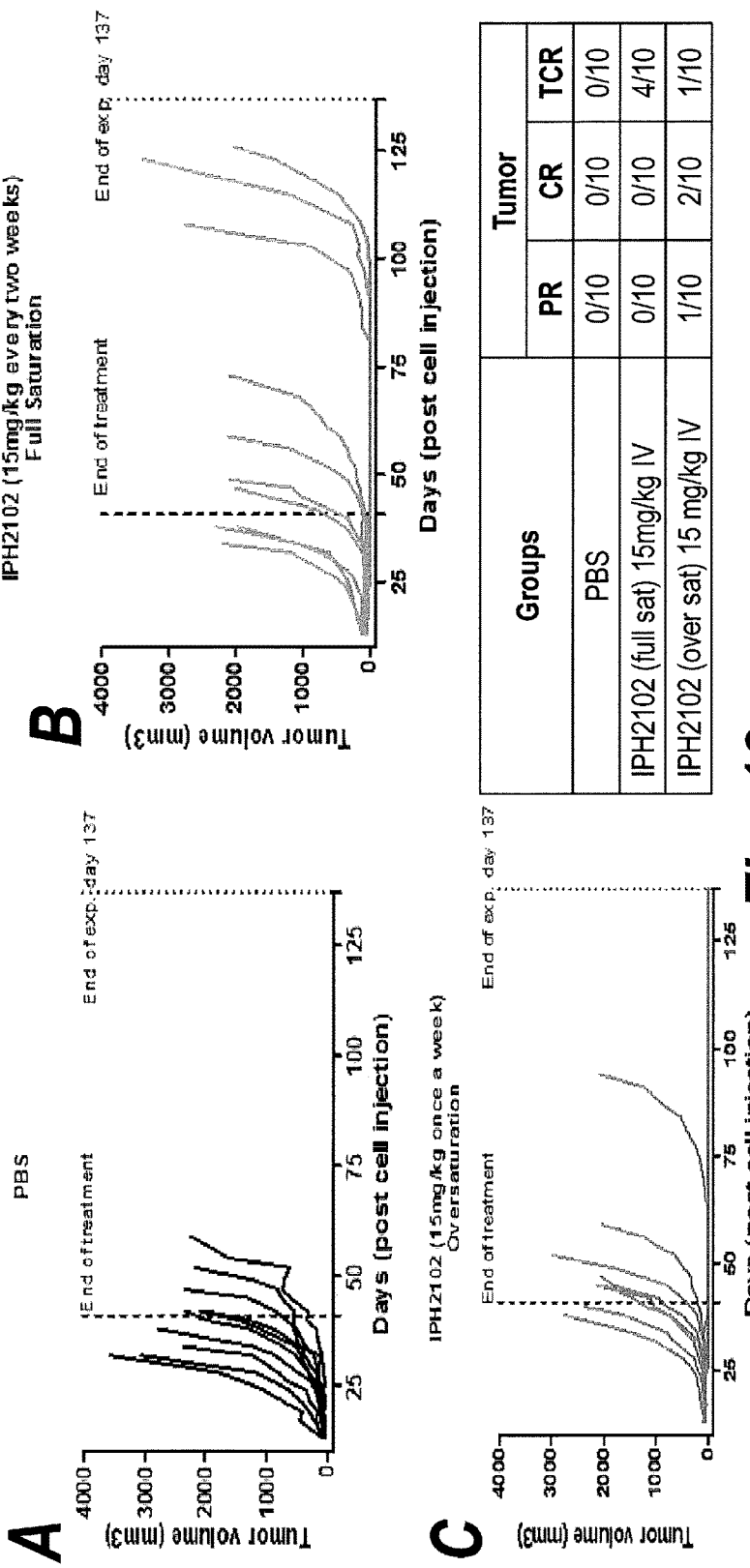
FIGS. 18A-C are a series of graphs showing the follow up until day 137 of KIRtg-RAG mice with complete OPM-2 tumor regression.

At Day 63, when almost all tumors had reached the cut-off volume of 2000 mm$^3$ (except for one in the full saturation group), animals whose tumor had completely regressed (3 in each treated group) were monitored. In the group treated with lirilumab in KIR full saturated condition, all the tumors that had completely regressed regrew after a delay from 43 to 73 days. On the other hand, in the group treated in oversaturated condition, only one tumor out of three regrew, indicating that the "oversaturation" of KIR receptor could have a greater benefit to control tumoral cells (FIGS. 18A-C).

In view of these data, the experimental condition under which lirilumab induced KIR full saturation (15 mg/kg every two weeks) was selected to combine with elotuzumab. However, before proceeding, it was important to assess whether CS1 and HLA-cw3 expression were maintained on the surface of tumor cells once engrafted in mice. Moreover, an analysis of the tumor by flow cytometry was performed to ensure that NK cells infiltrated the tumor and could mediate ADCC when targeted by elotuzumab and lirilumab.

Tumors with different volumes from 8 animals, not included in the randomization, were removed at 4 different time points and analyzed by flow cytometry.

Figure 19:
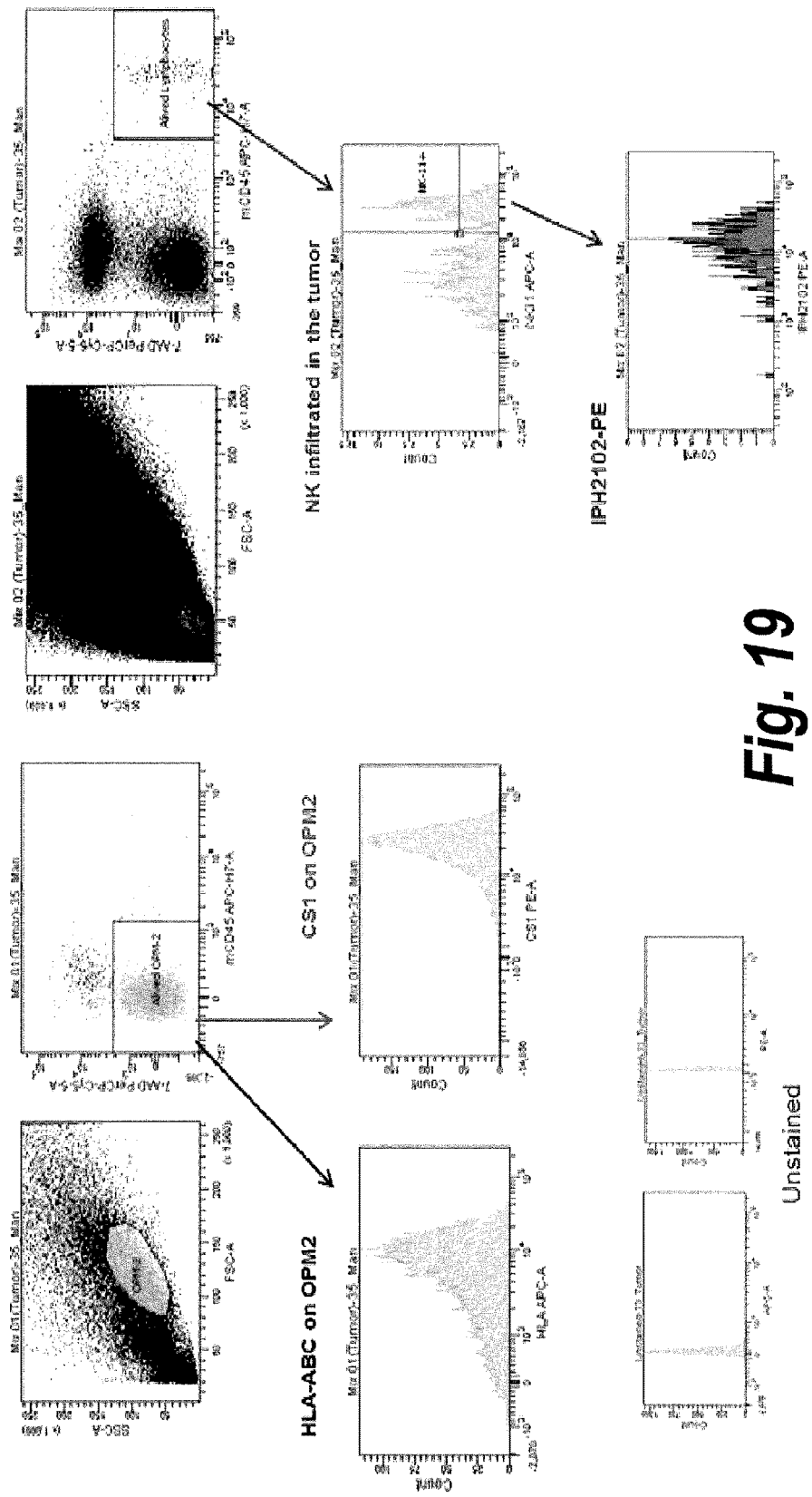
FIG. 19 depicts the gating strategy for OPM-2 and tumor infiltrating NK cells.

FIG. 19 illustrates the gating performed to analyze the expression level of CS1 and HLA-ABC on the OPM-2 surface and to evidence NK infiltrated into the tumor. In 4 out of 8 tumors, KIR2DL3 expression on infiltrated NK was also evaluated.

TABLE 6

Summary data of CS1 and HLA-ABC expression, NK infiltrated

| Day | Mouse | Tumor volume | MFI CS1 | MFI HLA-ABC | % NK among lympho | MFI IPH2102-PE on NK |
|---|---|---|---|---|---|---|
| D 14 | 26 | 114.3 | 12240 | 53688 | 65.3 | |
| | 28 | 136.6 | 10471 | 87808 | 61.3 | |
| D 21 | 36 | 500.6 | 14711 | 95025 | 41.2 | |
| | 40 | 27.2 | 8884 | 202474 | 14.9 | |
| D 33 | 30 | 2261 | 13761 | 18131 | 48.3 | 9246 |
| | 45 | 1106 | 17305 | 23834 | 46.8 | 14019 |
| D 42 | 33 | 972 | 17890 | 19957 | 42.2 | 12408 |
| | 35 | 3325 | 21900 | 7157 | 40.5 | 11080 |

Figure 20:
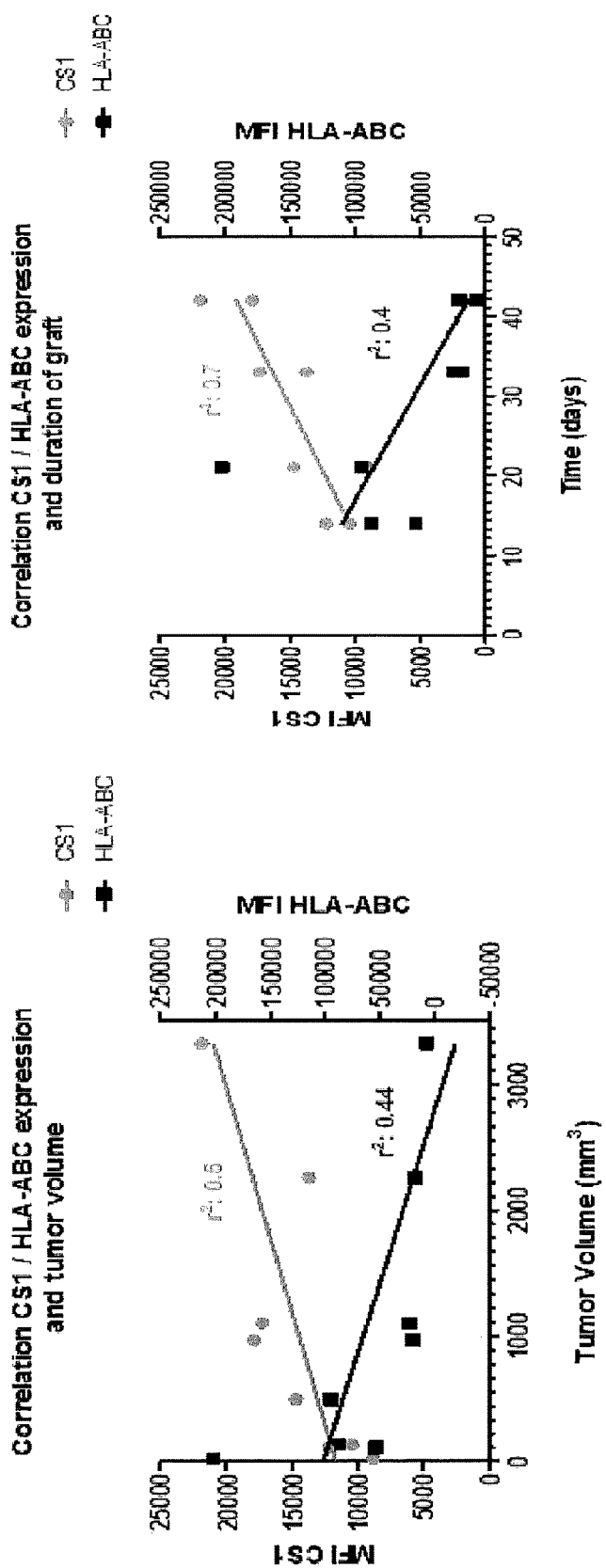
FIG. 20 are graphs which show the correlation between CS1 and Class-I expression and tumor volume (left graph) and time post engraftment (right graph).

Expression levels of both CS1 and HLA-ABC were maintained on the OPM-2 cell surface when engrafted in mice (Table 6). For CS1, there was a tendency of increased expression related to the tumor volume growth and the time post engraftment. For MHC Class-I expression (in contrast to CS1), a tendency of decreased expression was observed (except for the mouse No. 40 which had a very small tumor) (FIG. 20).

Figure 21:
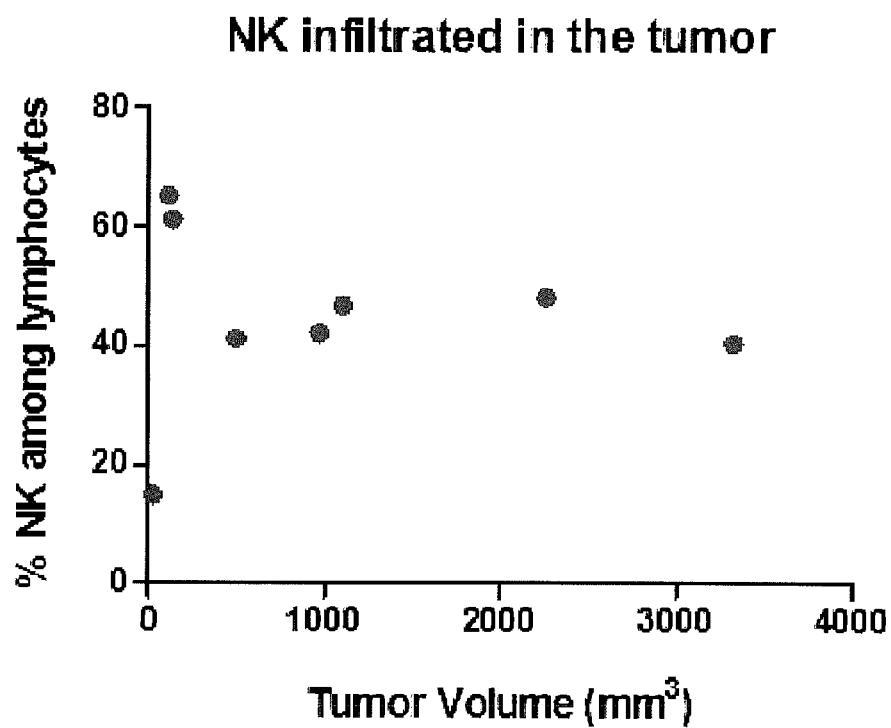
FIG. 21 is a graph showing the correlation between NK cell infiltration of the tumor and tumor volume.

Between 40 to 60% of lymphocytes found in the tumors were NK cells (except again for mouse No. 40) that expressed KIR2DL3 (Table 6). This percentage was not related to the size of the tumor (FIG. 21).

In conclusion, CS1 (target of elotuzumab) and MHC Class-I (ligand of the KIR molecule targeted by lirilumab), were expressed in vivo. Moreover, NK cells that expressed KIR2DL3 could infiltrate the tumor.

Dose Response to Elotuzumab

The anti-tumoral activity of elotuzumab against OPM-2 tumors has been characterized in SCID mice at the dosage of 0.1, 0.5, 1 and 10 mg/kg (Tai Y, et al., *Blood.* 2008; 112:1329-1337). To determine the optimal dose of elotuzumab to be combined with lirilumab, two intermediary doses were selected i.e., 0.5 and 2 mg/kg (Table 7).

TABLE 7

Experimental Design

| Exp. N° | Groups | Treatment | n = | Mean volume | Randomization Day |
|---|---|---|---|---|---|
| 5 | IC (hIgG1) 2 mg/kg IP | twice/w for 7 injections | 10 | 47.9 ± 12.9 | 10 |
|  | elotuzumab 0.5 mg/kg IP | twice/w for 7 injections | 10 | 47.6 ± 12.6 |  |
|  | elotuzumab 2 mg/kg IP | twice/w for 7 injections | 10 | 48.1 ± 16.8 |  | n = number of mice

Elotuzumab demonstrated a huge dose-dependent antitumoral activity. More than two mice in each treated group presented a complete regression of the tumor, avoiding the calculation of anti-tumoral parameters (i.e., TGD, DT). The analysis of curve profiles showed a greater number of complete and temporary complete regressions at the dose of 2 mg/kg than at 0.5 mg/kg (FIGS. 22A-C).

Figure 23:
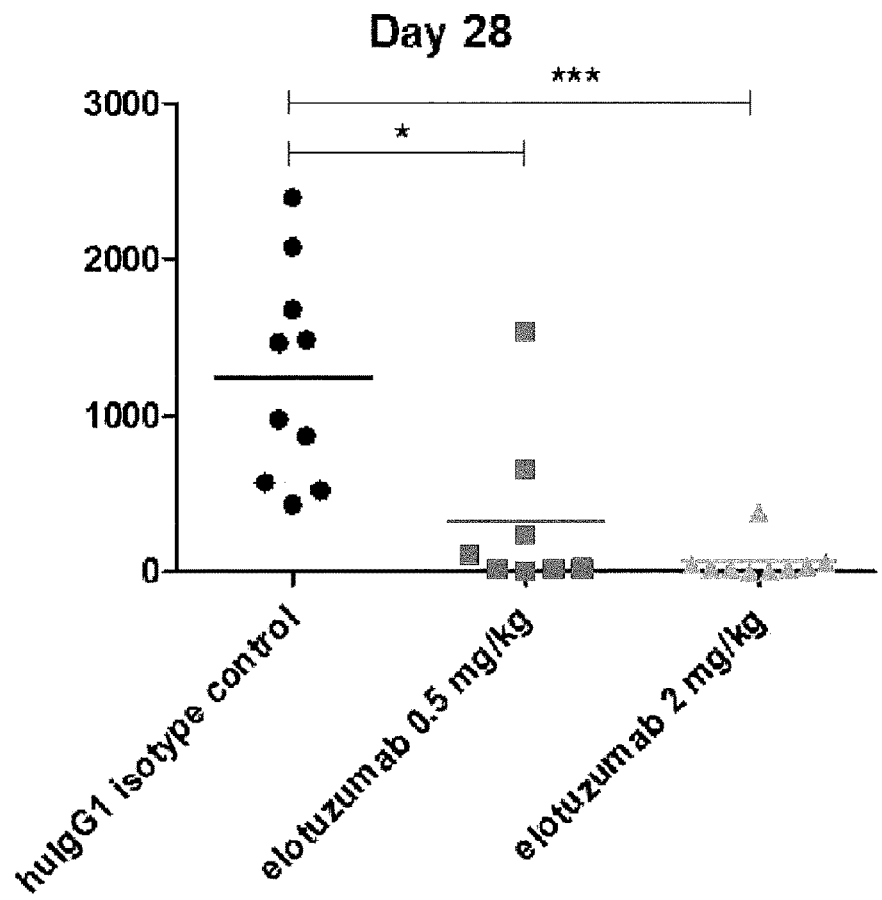
FIG. 23 is a graph which shows the comparison of elotuzumab treated groups with the control at day 28 post graft.
Figure 24:
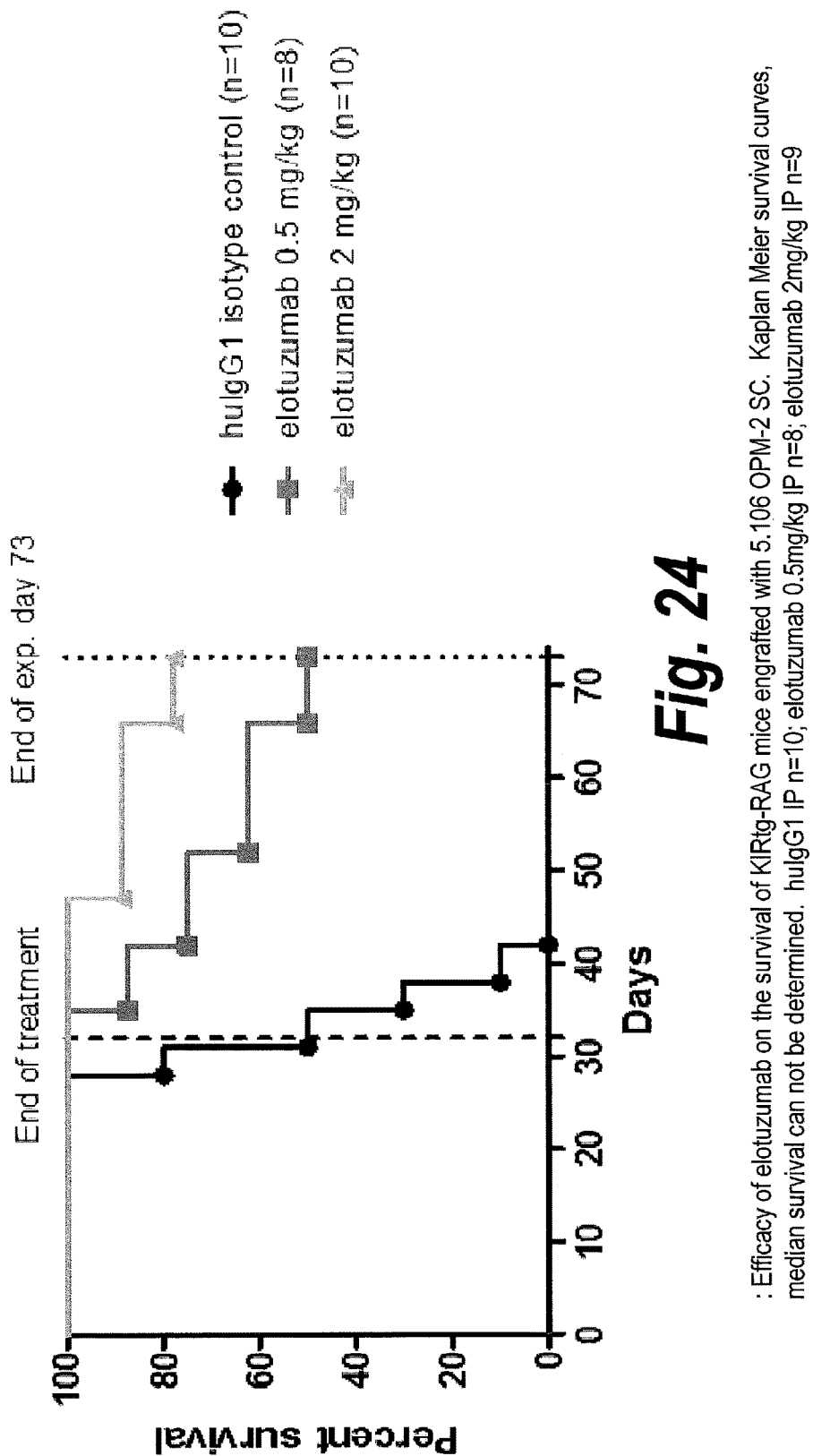
FIG. 24 is a graph which shows the efficacy of elotuzumab on the survival of KIRtg-RAG mice engrafted with 5×10$^6$ OPM-2 SC.

Comparison of the two elotuzumab treated groups with the control demonstrated that the dose of 2 mg/kg had significantly stronger anti-tumoral activity compared to the dose of 0.5 mg/kg (FIG. 23). Similarly, survival curves highlighted a greater activity for the dose of 2 mg/kg. The median survival could not be determined for either dose because more than 50% of animals were still alive at the end of the experiment, further evidencing the anti-tumoral activity (FIG. 24). In view of these results, the sub-optimal dose of elotuzumab i.e. 0.5 mg/kg was selected to combine with lirilumab in the next experiments.

Combined Effect of Elotuzumab and Lirilumab (IPH2102)

The combined activity of elotuzumab and lirilumab was evaluated according the experimental design shown in Table 8.

TABLE 8

Experimental Design

| Exp. N° | Groups | Treatment | n = | Mean volume | Randomization Day |
|---|---|---|---|---|---|
| 6 | hIgG1 0.5 mg/kg IP + Diluant IPH2102 IV | twice/w for 7 inject° + D11, D24 | 10 | 49.4 ± 15.4 | 11 |
|  | elotuzumab 0.5 mg/kg IP + Diluant IPH2102 IV | twice/w for 7 inject° + D11, D24 | 10 | 49.3 ± 14.8 |  |
|  | hIgG1 0.5 mg/kg IP + IPH2102 15 mg/kg IV | twice/w for 7 inject° + D11, D24 | 10 | 48.7 ± 13.4 |  |
|  | elotuzumab 0.5 mg/kg IP + IPH2102 15 mg/kg IV | twice/w for 7 inject° + D11, D24 | 10 | 49.4 ± 13.6 |  | n = number of mice

For the elotuzumab group, the analysis of curve profiles showed one partial regression, one complete regression, and one temporary complete regression. Lirilumab combined with elotuzumab potentiated its effect. Indeed, partial regression and temporary regression were transformed into complete regression. As a consequence the number of complete regression increased from 2 to 6 (FIG. 25).

Figure 26:
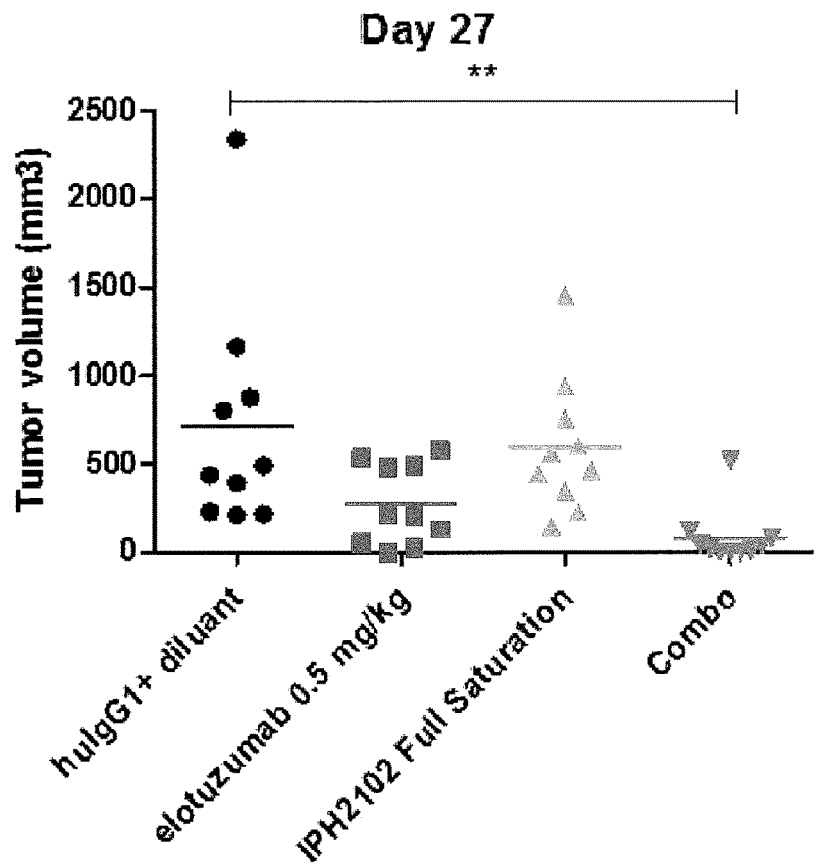
FIG. 26 is a graph which shows the comparison of elotuzumab, IPH2102 and combined treated groups with the control at day 27 post graft.
Figure 27:
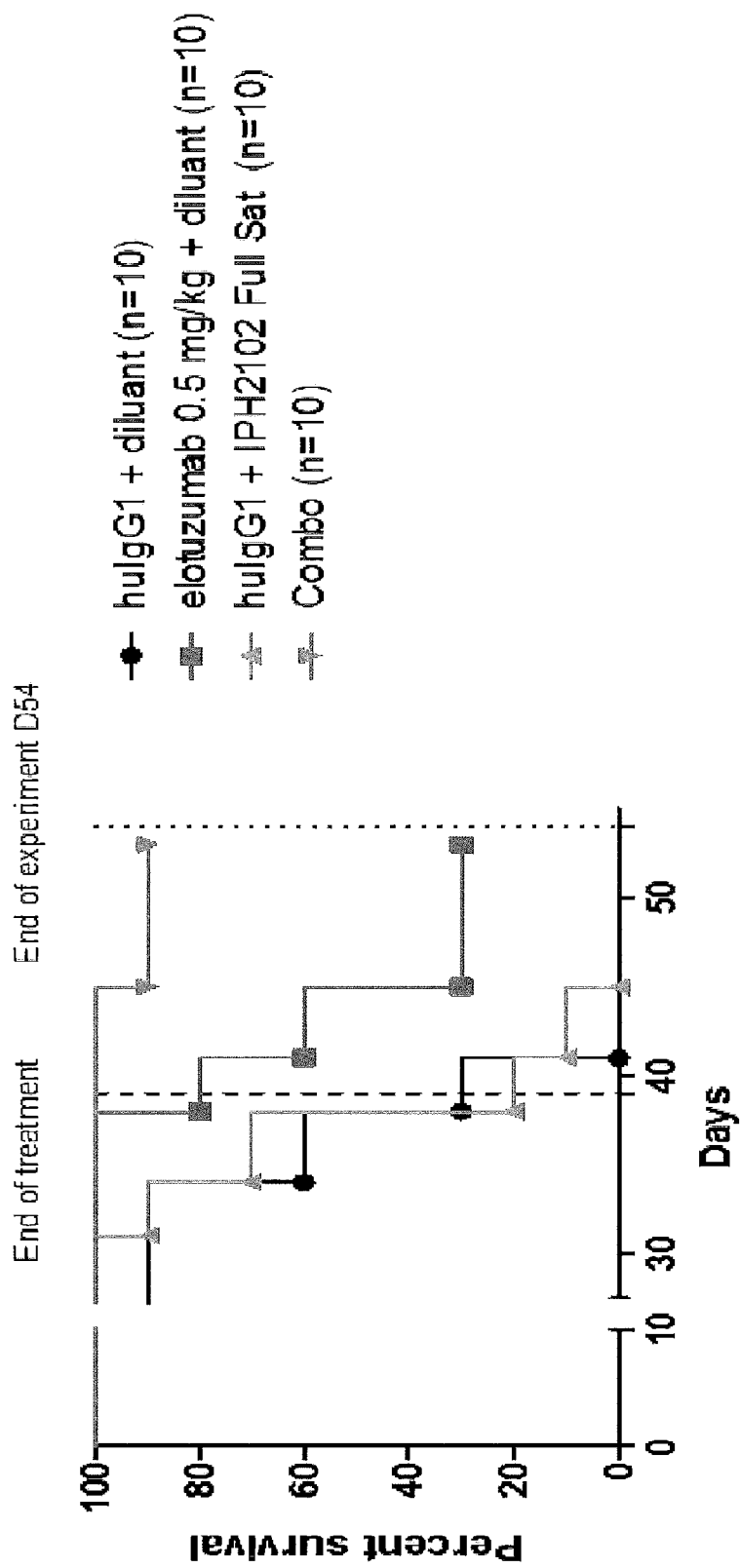
FIG. 27 is a graph which shows the efficacy of elotuzumab, IPH2102 and combined treatments on the survival of KIRtg-RAG mice.
Figure 28A:
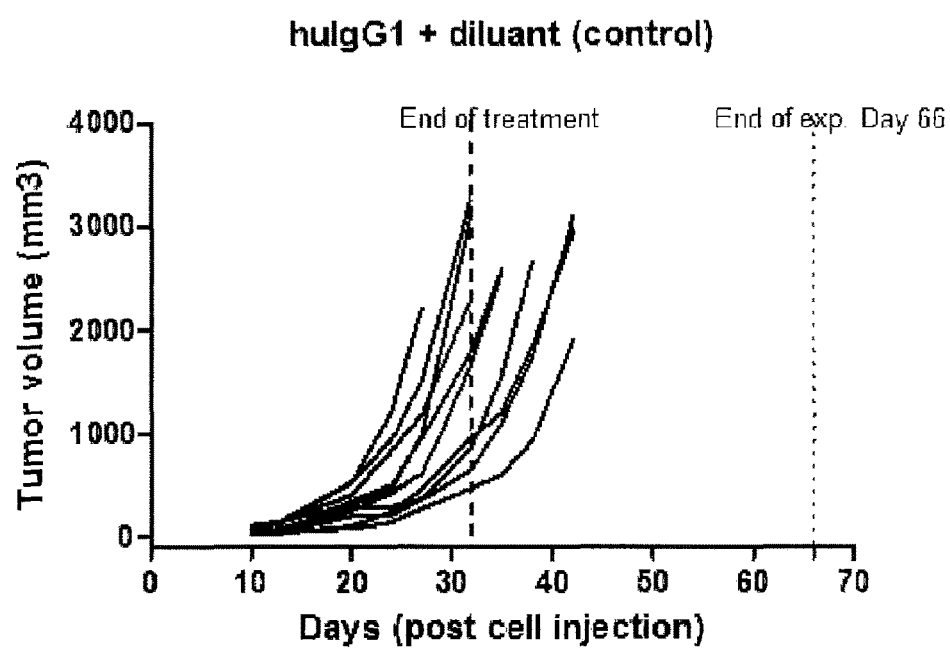

Comparison of the different groups at day 27 demonstrated a statistically significant difference between combined treatment group and control. The fact that elotuzumab group was not statistically different from the control (like in FIG. 23) is likely due to the heterogeneity of the control group (FIG. 26). The survival curves supported the same conclusions. The median survival of lirilumab group was similar to that of control (38 days), the median survival of elotuzumab group was 45 days, increasing the life span by 18%, and only one mouse of the combined group reached the tumoral volume of 2000 mm$^3$ during the experiment (FIG. 27).

Confirmation of Combined Effect of Elotuzumab and Lirilumab (IPH2102)

The next studies were performed (1) to confirm the combined anti-tumoral activity of lirilumab and elotuzumab and (2) to evaluate the involvement of NK cells in the anti-tumoral activity of both lirilumab and elotuzumab or their combination. For this, the groups of NK cell-depleted animals at the time of randomization were added as shown in Table 9.

TABLE 9

Experimental Design

| Exp. N° | Groups | Treatment | n = | Mean volume | Randomization Day |
|---|---|---|---|---|---|
| 7 | hIgG1 0.5 mg/kg IP + Diluant IPH2102 IV | twice/w for 7 inject° + D11, D25 | 10 | 66.0 ± 26.7 | 10 |
|  | elotuzumab 0.5 mg/kg IP + Diluant IPH2102 IV | twice/w for 7 inject° + D11, D25 | 10 | 66.4 ± 26.9 |  |

TABLE 9-continued

Experimental Design

| Exp. N° | Groups | Treatment | n = | Randomization Mean volume | Day |
|---|---|---|---|---|---|
| | hIgG1 0.5 mg/kg IP + IPH2102 15 mg/kg IV | twice/w for 7 inject° + D11, D25 | 10 | 66.7 ± 28.0 | |
| | elotuzumab 0.5 mg/kg IP + IPH2102 15 mg/kg IV | twice/w for 7 inject° + D11, D25 | 10 | 66.6 ± 28.7 | |
| | anti-NK1.1 100 µg IV + elotuzumab 0.5 mg/kg IP + Diluant IPH2102 | D10, D24 + twice/w for 7 inject° + D11, D25 | 10 | 66.7 ± 30.5 | |
| | anti-NK1.1 100 µg IV + elotuzumab 0.5 mg/kg IP + Diluant IPH2102 | D10, D24 + twice/w for 7 inject° + D11, D25 | 10 | 66.3 ± 30.7 | |
| | anti-NK1.1 100 µg IV + elotuzumab 0.5 mg/kg IP + Diluant IPH2102 | D10, D24 + twice/w for 7 inject° + D11, D25 | 10 | 68.3 ± 36.5 | | n = number of mice

For elotuzumab-treated animals, the analysis of curve profiles showed 2 partial regressions, 1 complete regression, and 2 temporary complete regressions (an anti-tumoral activity similar to that observed in FIGS. 28A-D). The complete regression was abrogated when NK cells were depleted in these animals. Moreover, tumor growth delay (FIG. 29) and doubling time (FIG. 30) was reduced when NK cells were depleted, indicating that the activity of elotuzumab was partly mediated by NK cells.

Figure 29:
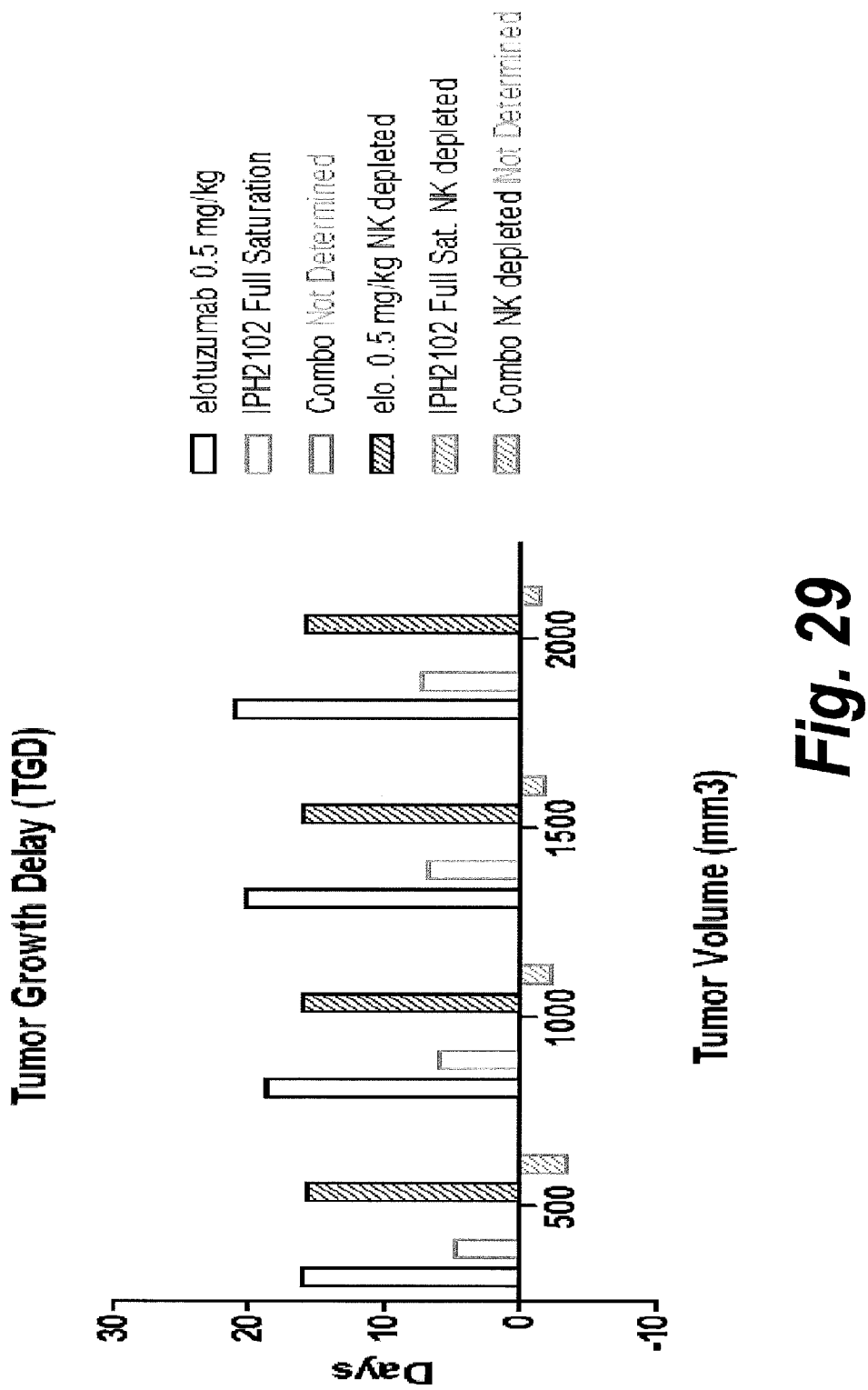
FIG. 29 is a graph which shows tumor growth delay of the different treated groups related to the control (huIgG1+diluent) calculated at 4 predetermined tumor volumes. For elotuzumab and IPH2102, TGD was calculated with n=8 mice.
Figure 30:
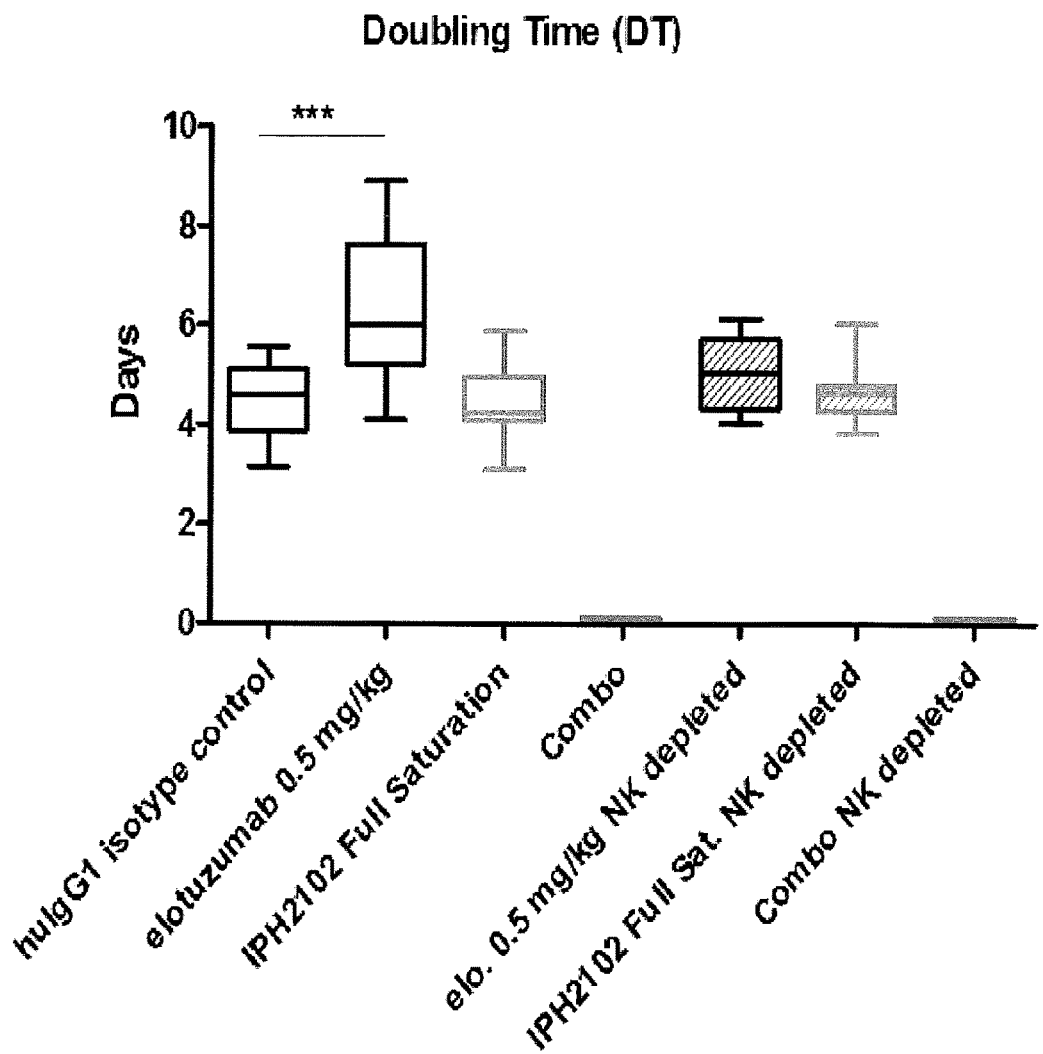
FIG. 30 is a graph which shows the doubling time of the different treated groups.

In this experiment, lirilumab confirmed its slight anti-tumoral activity with 1 complete regression and one temporary complete regression (FIGS. 28A-D). Even where lirilumab efficacy was not sustained, reduction and even abrogation of its activity were observed when NK cells were depleted. This was deduced by the abrogation of the complete or temporary complete regression, by the reduction of doubling time to reach that of the control (FIG. 30) and by the abrogation of the tumor growth delay (FIG. 29). This conclusion was also confirmed when the lirilumab group was compared to lirilumab NK cell-depleted group at day 27 (FIG. 31). These data indicate that the anti-tumoral activity of lirilumab was mediated by NK cells. For the elotuzumab and lirilumab groups, TGD and DT were calculated respectively from 8 out of 10 and 9 out of 10 mice because excluded mice reached the cut-off criteria for exponential growth fit.

The synergistic effect seen with combining elotuzumab and lirilumab was confirmed for the second time with 6 complete regressions (FIGS. 28A-D) and a strong statistical difference compared to the control at day 27 (FIG. 31). As expected, NK cell depletion strongly reduced this combined effect as complete regressions decreased from 6 to 2 (FIGS. 28A-D) and there was no statistically significant difference with the control group (FIG. 31).

Figure 32:
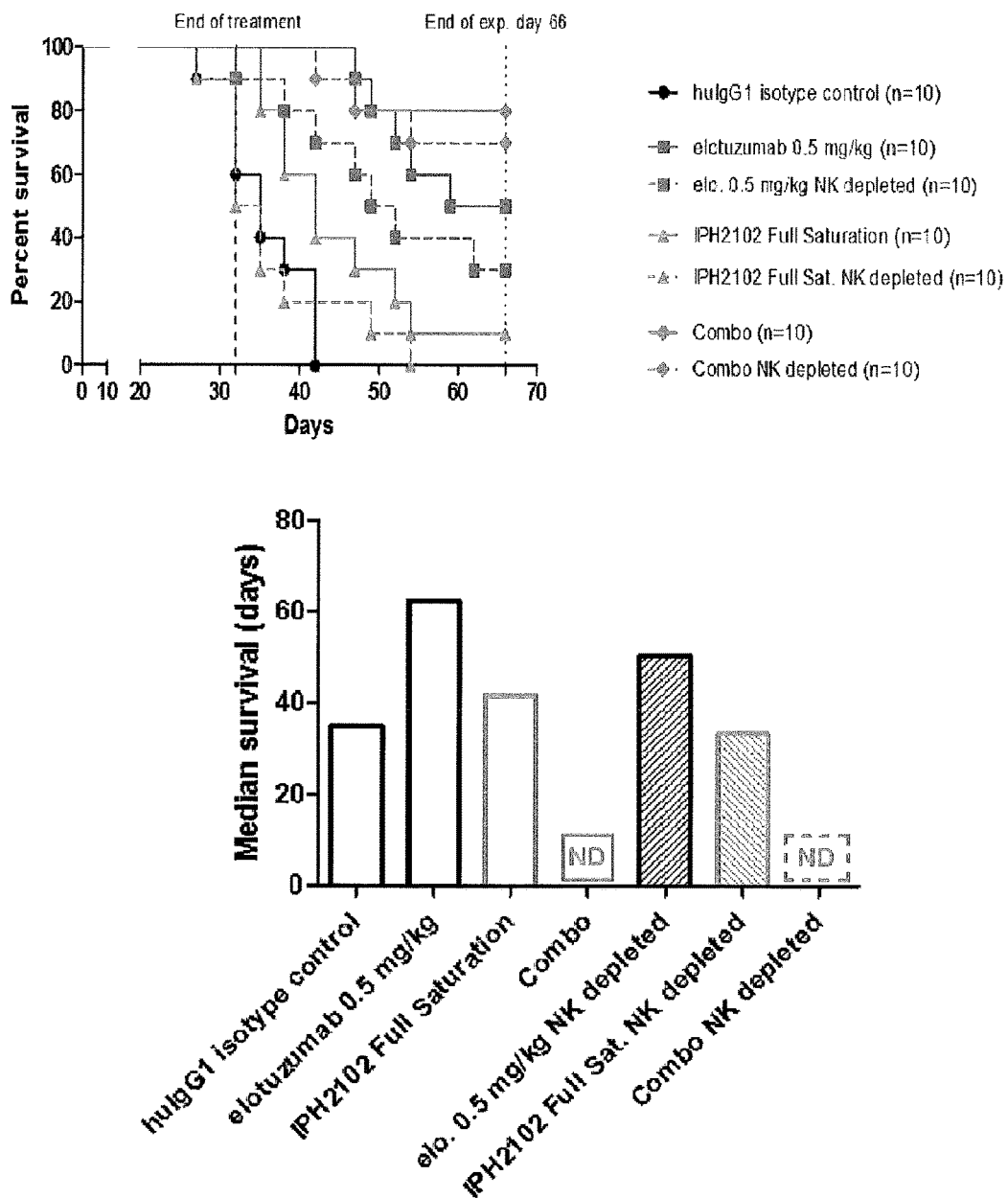
FIG. 32 are graphs which show the involvement of NK cells in the combined activity of elotuzumab and lirilumab, and the effect of the combination treatment on the survival of KIRtg-RAG mice engrafted with 5×10$^6$ OPM-2 SC. Kaplan-Meier survival curves (n=10).

All the parameters analyzed converged to the same conclusion. Indeed, survival analysis clearly demonstrated the strong combined efficacy of both compounds. Moreover, the median survival analysis confirmed the partial involvement of NK cells in the effect of elotuzumab and the full involvement in lirilumab activity (FIG. 32). In conclusion, the combination of elotuzumab and lirilumab induced a synergistic anti-tumoral activity, strongly mediated by NK cells.

Confirmation of Effect of Elotuzumab and Lirilumab at High Tumoral Volume

In view of the strong anti-tumoral activity of elotuzumab and lirilumab combination, the anti-tumoral activity on high-volume tumors (around 140 mm$^3$) was also evaluated based on the experimental design shown in Table 10.

TABLE 10

Experimental Design

| Exp. N° | Groups | Treatment | n = | Randomization Mean volume | Day |
|---|---|---|---|---|---|
| 9 | hIgG1 0.5 mg/kg IP + Diluant IPH2102 IV | twice/w for 7 inject° + D18, D32 | 10 | 133.68 ± 78.03 | 17 |
| | elotuzumab 0.5 mg/kg IP + Diluant IPH2102 IV | twice/w for 7 inject° + D18, D32 | 10 | 139.32 ± 79.28 | |
| | hIgG1 0.5 mg/kg IP + IPH2102 15 mg/kg IV | twice/w for 7 inject° + D18, D32 | 10 | 140.23 ± 79.33 | |
| | elotuzumab 0.5 mg/kg IP + IPH2102 15 mg/kg IV | twice/w for 7 inject° + D18, D32 | 10 | 142.76 ± 83.73 | | n = number of mice

When administered at high tumoral volume, elotuzumab did not induce partial or complete regression (FIG. 33), but increased the tumor doubling time and induced a tumor growth delay (FIG. 34). Lirilumab had no anti-tumoral activity in this setting, but it potentiated the anti-tumoral activity of elotuzumab when combined, i.e., DT and TGD were increased (FIG. 34).

For the combined group, DT was calculated for 8 out of 10 mice (because the two excluded mice reached the cut-off criteria for exponential growth fit).

Figure 35:
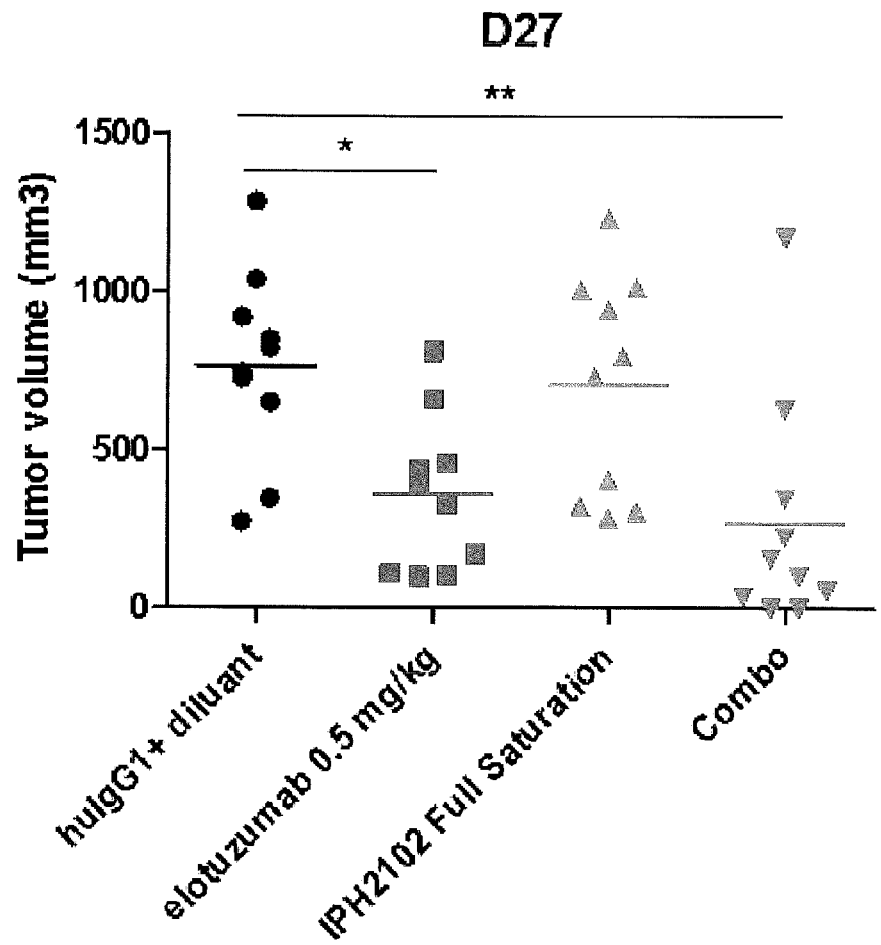
FIG. 35 is a graph which shows the comparison at day 27 post graft of the different groups treated at high tumoral volume.

Detailed analysis performed at day 27 shows that the synergistic activity of the combination of elotuzumab and lirilumab was maintained on tumors with high volume (FIG. 35).

Figure 36:
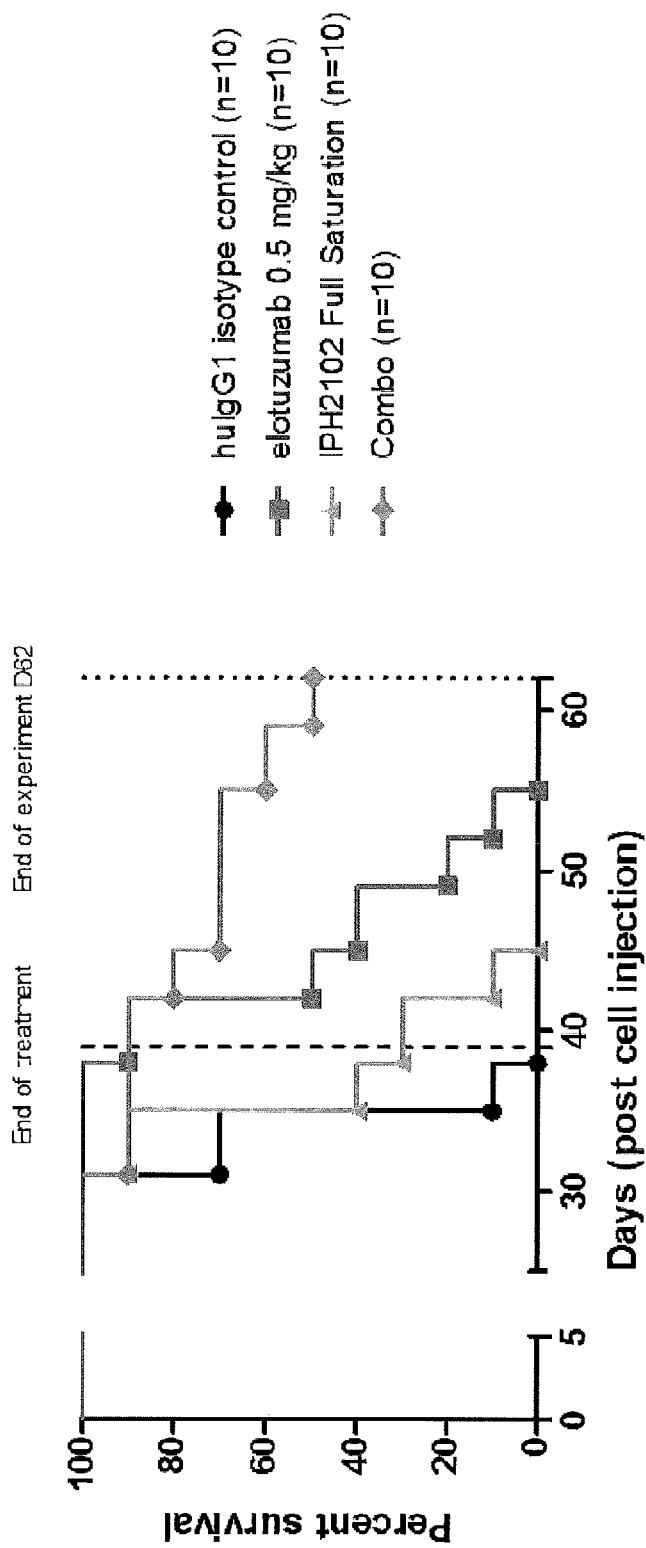
FIG. 36 is a graph which shows the efficacy of elotuzumab, IPH2102 and combined treatments, administered at high tumoral volume, on the survival of KIRtg-RAG mice engrafted with 5×10$^6$ OPM-2 SC.

Survival analysis further confirmed the conclusions. Elotuzumab had prolonged median survival of 43 days versus 35 for the control, increasing the life span by 23%. Mice treated with lirilumab had the same median survival as the control, but median survival was strongly increased when lirilumab was combined with elotuzumab to reach 60 days, an increase in life span of 71% (FIG. 36).

Accordingly, even when administered at high tumoral volume, the combination of elotuzumab and lirilumab was highly effective and exhibited a synergistic effect in prolonging survival.

Conclusion

CS1 (target of elotuzumab) and MHC Class-I (ligand of the KIR molecule targeted by lirilumab) were expressed on the surface of OPM-2 cells in vivo. Moreover, NK cells that expressed KIR2DL3 could infiltrate the tumor.

Lirilumab was shown to have slight anti-tumoral activity against OPM-2 solid tumors in KIRtg-RAG mice. This activity is related to the saturation level of KIR2DL3, with a more pronounced effect seen when receptors are oversaturated. The activity of lirilumab is mediated by NK cells, since the lirilumab anti-tumoral effect is abrogated when NK cells are depleted.

Elotuzumab demonstrates a strong dose-related anti-tumoral effect on OPM-2 tumors. This activity is partly mediated by NK cells.

The combination of lirilumab and elotuzumab demonstrated a synergistic anti-tumoral activity mediated by NK cells. This effect is also observed when the combined therapy is administered in animals with high tumor volumes.

This study highlights the synergistic therapeutic efficacy of combination therapy with an antibody that blocks NK cell inhibition mediated by the interaction of KIR2DL3 and HLA-cw3 and a cytotoxic antibody, elotuzumab, that targets CS1, a tumoral antigen located on MM cells, by ADCC.

Example 3

Additional In Vivo Studies—Combination of Elotuzumab and Lirilumab

Additional in vivo studies were performed to assess the therapeutic efficacy of lirilumab (IPH2102) and elotuzumab in vivo, in a novel strain of double-transgenic mice expressing human KIR2DL3, as well as its ligand, HLA-cw3, on a Rag1$^{-/-}$ background (KIR-cw3-tgRAG mice), to allow engraftment of human MM tumor cells expressing SLAMF7.

In brief, Rag–/– mice and KIR2DL3 transgenic (tg) mice were crossed to obtain KIR2DL3tg, Rag–/– mice. HLA-Cw3 transgenic mice were crossed with KbDb–/– mice, resulting in Cw3tg, KbDb–/– mice. The mice are described in Romagne et al., (2009) *Blood* 114: 2667-2677 as well as in Sola et al. (2009) *P.N.A.S.*, U.S.A 106(31):12879-12884.

Figure 37:
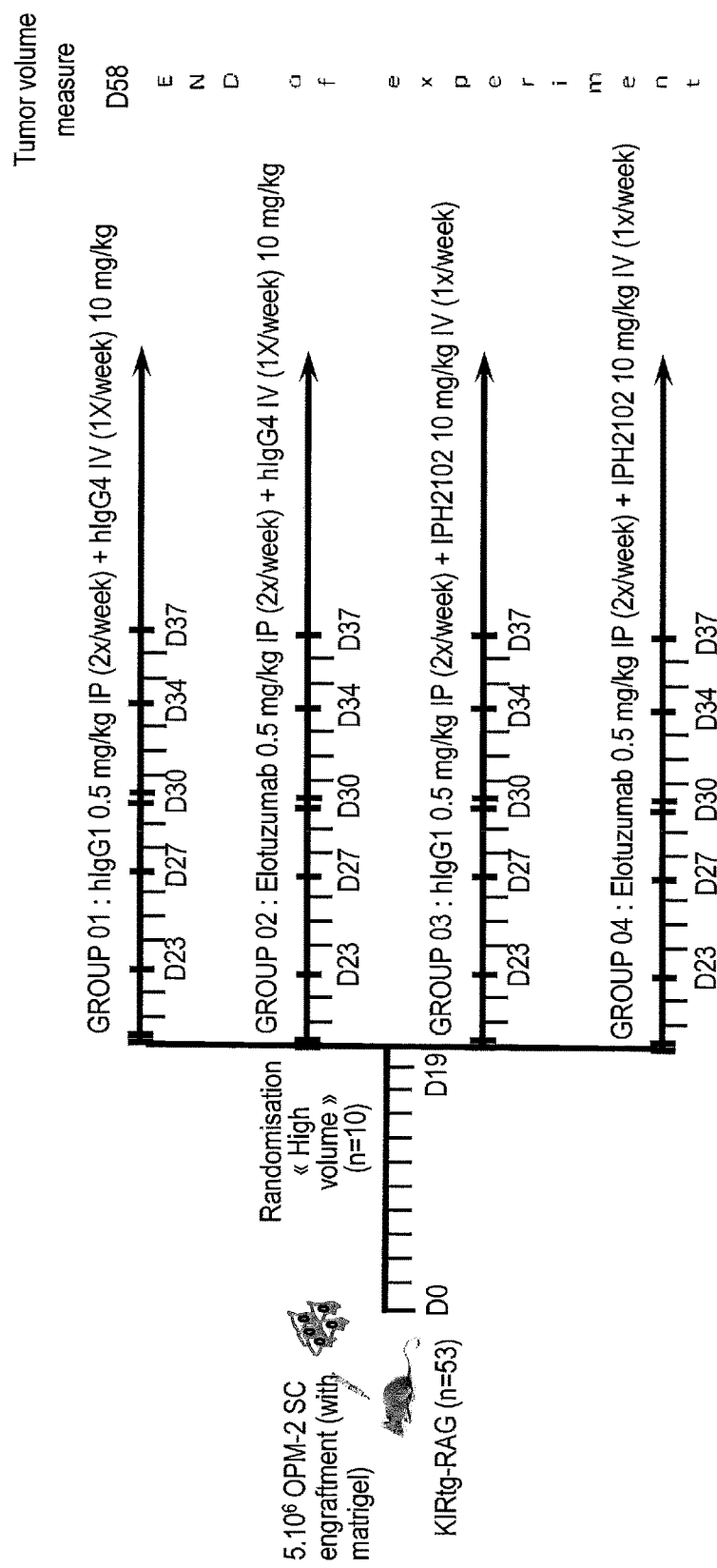
FIG. 37 is a schematic depicting the experimental design of an in vivo study to assess the therapeutic efficacy of lirilumab and elotuzumab in vivo, in KIR-cw3-tgRAG mice.

The OPM-2 MM cell line was sub-cutaneously engrafted in these mice and when high tumor volumes (140 mm$^3$) were reached, mice were treated with lirilumab once weekly (together with hIgG1 isotype control for elotuzumab), elotuzumab twice weekly (together with hIgG4 isotype control for lirilumab), or a combination of both. FIG. 37 depicts the experimental design.

Figure 38:
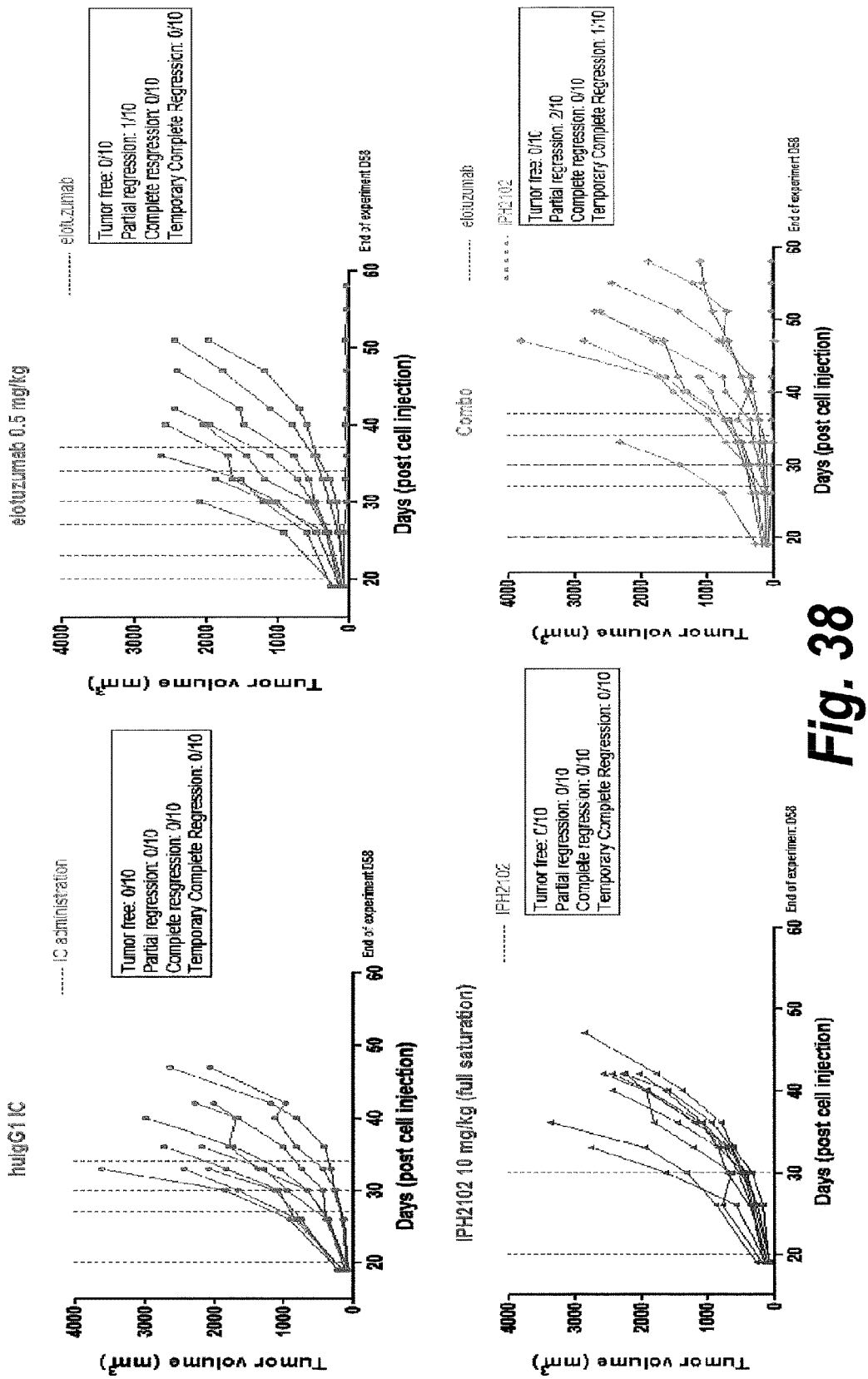
FIG. 38 are graphs depicting the antitumoral activity of individual KIR-cw3-tgRAG mice treated with a control, elotuzumab, lirilumab, or lirilumab in combination with elotuzumab.
Figure 39:
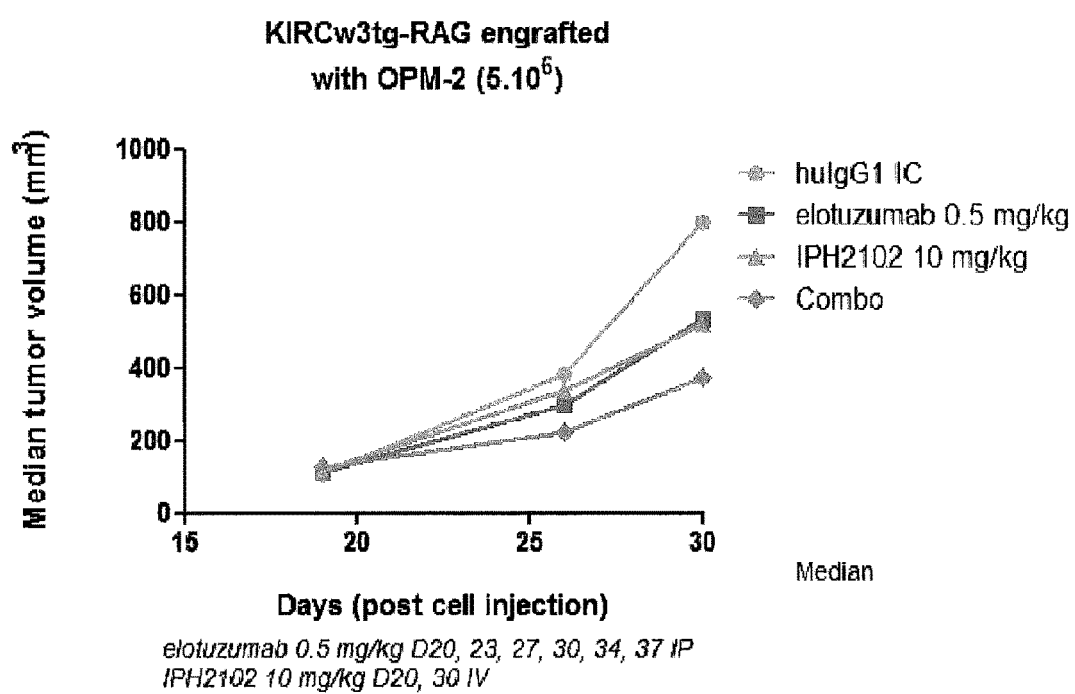
FIG. 39 is a graph comparing the median antitumoral activity of KIR-cw3-tgRAG mice treated with a control, elotuzumab, lirilumab, or lirilumab in combination with elotuzumab.

As shown in the results set forth in FIGS. 38 and 39, each monoclonal antibody had some therapeutic effect as a monotherapy, while the combination of both antibodies resulted in a significantly stronger anti-tumor effect and increased survival. Specifically, the median survival of mice treated with huIgG control was 38 days, 41 days with lirilumab, 42 days with elotuzumab and 51 days with both antibodies in combination.

In sum, the results show that blockade of KIR checkpoint receptors with lirilumab augmented elotuzumab mediated ADCC in vitro and synergized with elotuzumab to mediate potent anti-MM activity in vivo.

Example 4

Pharmacokinetics in Patients

Plasma concentrations of anti-KIR antibody are determined by ELISA as briefly described below.

The plates are coated with KIR2DL3 coating solution (1000/well) and incubated overnight at about 4° C. The plates are then washed 3 times with wash buffer using an automated plate washer (400 µl/well). Blocking buffer is added (200 µl per well) and plates are incubated for approximately 2 hours on a plate shaker at room temperature. After this, the plates are once again washed 3 times with wash buffer (400 µl/well).

Standards, quality controls and samples are added to the plates (100 µl/well) before incubation for approximately 2 hours on the plate shaker at room temperature. Before adding mouse anti-human IgG4:peroxidase working solution (100 µl/well) the plates are washed another 3 times (as above). The plates are then again incubated for approximately 2 hours on a plate shaker at room temperature, after which they are washed once again.

TMB is added to the plates (100 µl/well), which are then incubated for approximately 30 minutes on a plate shaker at room temperature. The enzymatic reaction is terminated with addition of stop solution (50 µl/well). Absorbances are read at 450 nm (reference filter 650 nm). The lower limit of quantification for this study is 5.000 ng/mL and the upper limit of quantification for this study is 110.0 ng/mL.

Example 5

KIR Occupancy Assay

Receptor occupancy is evaluated on human whole blood samples by four-color fluorescence analysis. Briefly, free and bound KIR2D receptor levels are assessed on T and NK lymphocytes in EDTA anti-coagulated peripheral blood. Free site assay assesses unbound KIR2D by staining with PE-conjugated anti-KIR antibody, which binds to the KIR2D molecule. Bound site assay assesses KIR2D receptors occupied by the anti-KIR antibody by staining with a PE-conjugated mouse anti-human IgG4 monoclonal antibody that recognizes the anti-KIR antibody bound to the KIR2D receptors. The Free and Bound Assays allows for assessment of both percentage positive staining, as well as the fluorescence intensity [MESF] for the PE-conjugated anti-KIR antibody or anti-hIgG4-PE. The following combinations of conjugated antibodies are used in the following two assays:

Free Site Assay: CD3/anti-KIR antibody/CD45/CD56
Bound Assay: CD3/hIgG4/CD45/CD56

Samples are analyzed on a Becton Dickinson FACScalibur using the Becton Dickinson Cellquest software. T cells are defined as CD45+CD3+ lymphocytes and NK cells are defined as CD45+CD3−CD56+ cells.

Example 6

Phase I Trial in Patients with Multiple Myeloma

A phase 1 trial of an anti-KIR antibody (lirilumab) and an anti-CS1 antibody (elotuzumab) is conducted in patients having MM to demonstrate the efficacy of administering these two therapeutics as a combination treatment.

The trial consists of two segments. Segment 1 includes dose escalation of lirilumab in combination with elotuzumab in subjects with MM. Segment 2 follows segment 1 and includes dose expansion of lirilumab in combination with elotuzumab in subjects with relapsed/refractory MM, and subjects with post autologous transplant. In both segments, subjects receive elotuzumab and lirilumab in two stages (Induction and Maintenance). During Induction, subjects are administered intravenous (IV) doses of elotuzumab weekly for 8 doses and IV doses of lirilumab every 4 weeks for 2 doses. During Maintenance, subjects are administered IV doses of elotuzumab every 2 weeks and lirilumab every 4 weeks, for up to two years of study therapy.

1. Objectives

The primary objective of this study is to assess the safety and tolerability of elotuzumab administered in combination with lirilumab and to identify dose limiting toxicities (DLTs) and the maximally tolerated dose (MTD) of the combination, in subjects with MM.

Secondary objectives include assessing the preliminary anti-tumor activity of the combination, characterizing the pharmacokinetics (PK) of the combination, monitoring immunogenicity of the combination, and assessing the pharmacodynamic effects of the combination on cell number and function of bone marrow plasma cells and natural killer cells.

Exploratory objectives include assessing the pharmacodynamic effects of the combination on peripheral natural killer and T cell function, exploring the relationship of safety and efficacy with changes in plasma cells and natural killer and T cell function, and assessing the landmark overall survival at three years following the start of therapy with the combination.

2. Overview of Study

This is a randomized phase I, open label study that includes the following select subjects with MM: subjects with relapsed and or refractory disease, or subjects who are post autologous transplant and have achieved very good partial response (VGPR) or better response. This study is performed in two segments: dose escalation and cohort expansion. Dose escalation is performed to characterize the safety and tolerability of elotuzumab administered in combination with lirilumab in subjects with MM, and is followed by a cohort expansion. Cohort expansion groups establish expanded safety experience with the combination and enable characterization of the immunoregulatory (biomarker) activity and preliminary antitumor efficacy of elotuzumab with lirilumab. Study treatment in both segments is divided into two distinct parts: Induction and Maintenance.

In both segments, subjects complete up to four periods of the study: Screening (up to 28 days), Treatment (Induction and Maintenance, up to a maximum of two years of study therapy), Clinical Follow-up (100 days), and Survival Follow-up (up to 3 years following the first dose of study drug).

Study Treatment—Induction Phase:

Subjects receive intravenous (IV) doses of elotuzumab weekly for 8 doses and lirilumab every 4 weeks for 2 doses.

Study Treatment—Maintenance Phase:

Subjects receive IV doses of elotuzumab every 2 weeks and lirilumab every 4 weeks, for up to two years of study therapy.

Subjects in the cohort expansion segment are treated at the maximally tolerated dose (MTD), the maximally administered dose (MAD), or at an alternative dose.

The decision to treat a subject with additional cycles of study therapy is based on disease assessment. Subjects with an overall response of CR unconfirmed, PR, SD, or PD-unconfirmed continue therapy until they develop PD-confirmed, CR-confirmed, experience clinical deterioration, develop adverse events requiring discontinuation, withdraw consent, or complete both Induction and Maintenance.

Subjects who: (1) complete Induction and Maintenance or (2) develop toxicity requiring discontinuation of the study therapies enter the Clinical Follow-up period until they have PD-confirmed, initiate new treatment, or complete all Clinical Follow-up (Follow-up Visit 1 (50 days post last treatment) and Follow-up Visit 2 (100 days post last treatment). Subjects who have PD-confirmed on study therapy enter Clinical Follow-up to continue monitoring for adverse events. At each Clinical Follow-up visit, assessments include physical examinations, adverse event assessment, safety laboratory testing, and disease assessment. If an adverse event has not resolved by the end of the Clinical Follow-up period, the subject continues follow-up until the adverse event has resolved to grade ≤1 or baseline, or is deemed irreversible. After completion of the Clinical Follow-up period, subjects enter the Survival Follow-up period. During this period, clinic visits or telephone contact every 3 months is performed to assess survival status. The duration of this period is up to 3 years following the first dose of study drug. Subjects in survival follow-up who have progression of disease are eligible to receive anti-cancer therapy as appropriate. A study schematic is presented in FIG. 40.

3. Dose Escalation

Three to nine subjects with MM are enrolled in successive cohorts assessing escalating doses of lirilumab administered in combination with elotuzumab. A 3+3+3 design is used to assess safety of elotuzumab given in combination with lirilumab. The dose selection is provided in Table 11.

TABLE 11

Schedule of Planned Dose Escalation

| Dose Cohort | Lirilumab mg/kg | Elotuzumab mg/kg | Number of Subjects |
| --- | --- | --- | --- |
| 1 | 0.3 | 10 | approximately 3-9 |
| 2 | 1 | 10 | approximately 3-9 |
| 3 | 3 | 10 | approximately 3-9 |

The Dose Limiting Toxicity (DLT) observation period lasts 4 weeks from initiation of study therapy. Three subjects are treated initially at each dose level. If 0 DLTs occur in a cohort of 3 subjects, a new cohort of 3 subjects is treated at the next higher dose level. If 1 of 3 subjects experience a DLT, that cohort is expanded to 6 subjects. If 1 of 6 subjects experiences a DLT, a new cohort of 3 subjects is treated at the next higher dose level. If 2 of 6 subjects experience a DLT, that cohort is expanded to 9 subjects. If 2 of 9 subjects experience a DLT, a new cohort of 3 subjects is treated at the next higher dose level. If 2 of 3, 3 of 6, or 3 of 9 subjects experience DLTs within a cohort, then that dose level is determined to have exceeded the maximum tolerated dose (MTD). Exploration of intermediate dose ranges is added to expand the safety data at various dose levels of lirilumab given in combination with elotuzumab. Statistical modeling is used to help support decision to move forward with a dose at or below the MTD. After determining the MTD, MAD, or completion of dose escalation without identifying the MTD and to further explore pharmacodynamic/biomarker objectives, 3-9 additional subjects are enrolled in each dose level for a total of up to 12 subjects at any dose level (original 3-9 subjects from dose escalation plus additional subjects required to have a total cohort size of 12).

No intra-subject dose escalation or reduction is allowed. Subjects who withdraw from the study during the DLT period for reasons other than toxicity are replaced within the same dose cohort. Subjects in dose escalation are continually monitored beyond the DLT period as well, to evaluate safety beyond the DLT period.

All available clinical and laboratory data, and the nature, time of onset, and time to resolution of DLTs observed during dose escalation are reviewed to determine whether an alternate dose schedule should be examined. If the MTD is exceeded in the first cohort, the evaluation of alternate doses and schedules of lirilumab is investigated.

4. Cohort Expansion

Cohort expansion is initiated at the MTD, the maximum administered dose (MAD), or an alternate dose, if recommended. Subjects are randomized to receive elotuzumab with lirilumab. Enrollment is limited to one of two specified patient populations with MM; Treatment Group A) subjects with relapsed and/or refractory disease, and Treatment Group B) subjects who are post an autologous transplant and have achieved VGPR or better response. Approximately 16 subjects are enrolled in each of the treatment groups.

Dose escalation has up to 9 subjects in each dose cohort. Any surplus subjects from dose cohorts that do not use 9 subjects are added to dose expansion cohorts. For example, if no DLT is observed and each cohort escalates to the next cohort using only 3 subjects, a surplus of 30 unused subjects is added to dose expansion.

Figure 40:
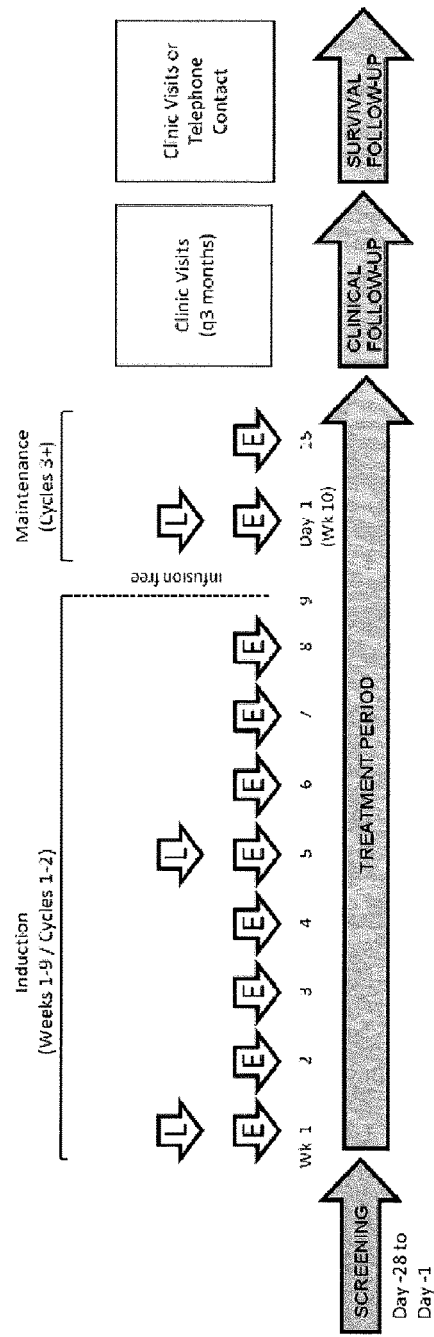
FIG. 40 is a schematic depicting the study design for the phase I trial.

Treatment Groups A & B:

Approximately 16 subjects undergo study treatment in both Induction and Maintenance segments as outlined in FIG. 40. Additional subjects, not used in dose escalation phase, may be added uniformly in treatment groups A and B.

Clinical safety monitoring of subjects enrolled during the cohort expansion segment of the study is identical to that conducted during the dose escalation segment of the study. As enrollment proceeds during cohort expansion, if the combined incidence of study drug related DLTs requiring dose modification exceeds 33% of treated subjects, further enrollment to that cohort is interrupted and the findings are be discussed. An agreement is reached whether a lower dose or an alternate dose or dose schedule of the combination is examined, or whether any additional treatment guidelines are to be implemented prior to enrollment of additional subjects.

5. Dose Limiting Toxicity

For the purpose of guiding dose escalation decision making, DLTs are determined based on the incidence and severity of study drug-related adverse events (AE) occurring within 4 weeks (28 days) of initiation of study therapy. Adverse events are graded according to the National Cancer Institute (NCI) Common Terminology Criteria for Adverse Events version 4.0 (CTCAEv4). For the purposes of subject management, DLTs generally lead to dose interruptions regardless of the cycle in which a DLT occurs.

6. Duration of Study

The Screening Period lasts up to 28 days. The Treatment Period (Induction & Maintenance) lasts up to 2 years. The Clinical Follow-up Period lasts 100 days. The Survival Follow-up Period lasts up to 3 years following the first dose of study therapy (Week 1). The total time on study for any individual subject does not exceed 3 years. The total duration of the study is expected to be 4.5 years from the time of the first visit of the first subject to the required survival follow-up of the last subject enrolled.

7. Study Population

Male and female subjects as determined by medical history, physical examination, 12-lead electrocardiogram (ECG), and clinical laboratory evaluations are eligible to participate in the study. Subjects must have histological confirmation of MM with measurable disease, and who meet all eligibility criteria.

Women of childbearing potential (WOCBP) must not be nursing or pregnant and must be using an acceptable method of contraception for at least 4 weeks before dosing. WOCBP must have a negative pregnancy test within 24 hours prior to dosing with study medication.

8. Study Assessments

Safety Outcome Measures: Adverse events are assessed continuously during the study and for 100 days after the last treatment. Adverse events are coded using the most current version of MedDRA and reviewed for potential significance and importance. Subjects are followed until all treatment related adverse events have recovered to grade ≤1 or baseline, or are deemed irreversible.

Safety assessments are based on medical review of adverse event reports and the results of vital sign measurements, ECGs, physical examinations, and clinical laboratory tests. The incidence of observed adverse events is tabulated and reviewed for potential significance and clinical importance.

Efficacy Assessments: Disease assessment with serum and urine myeloma lab tests, bone marrow assessment and computed tomography (CT) and/or magnetic resonance imaging (MRI), as appropriate, are performed at baseline. From induction until the start of maintenance, disease assessment occurs every 4 weeks (weeks 5, and 10 before starting maintenance). From the start of maintenance, disease assessment occurs every 12 weeks prior to dose administration. Disease assessments continue until there is confirmed disease progression, at the completion of follow-up, or until subjects withdraw from the study. In the absence of clinical deterioration, any initial assessment of progressive disease (PD) or complete remission (CR) is confirmed by a repeat evaluation at the next tumor assessment time point, but no sooner than 4 weeks later. Pharmacokinetic Measures: Pharmacokinetic parameters (Cmax, Cmin, Tmax, AUC(INF), AUC(TAU), T-HALF, % UR, CLT/F, CLR, Vss, and AI) are derived from plasma concentration versus time and urinary excretion data.

All subjects in cohort expansion are offered the opportunity of undergoing biopsies. All subjects who undergo biopsies are required to have peripheral blood collected in parallel for comparison of effects on bone marrow and peripheral immune and tumor cells.

9. Statistical Considerations

Dose Escalation: The same size at each dose depends on observed toxicity and cannot be precisely determined. There are 3-9 subjects in each cohort.

Cohort Expansion: A sample size of approximately 16 subjects allows for better estimation of the toxicity rate and provide greater precision around estimates around preliminary efficacy.

10. Endpoints

The primary endpoint of this phase 1 study is safety as measured by the rate of adverse events (AEs), serious, adverse events (SAEs), deaths, and grade 3/4 clinically significant laboratory abnormalities. Safety is evaluated on treatment, and for up to 100 days after the last dose of study drug is received. All subjects who receive any lirilumab or elotuzumab are included in the safety analyses.

Secondary efficacy endpoints vary by disease state. Among all subjects, the rate of progression free survival (PFSr) at pre-specified time points is summarized. Additionally, the objective response rate is determined (e.g., rate of PR or CR responses).

Secondary endpoints also include summary of select PK parameters, such as Cmax, AUC (TAU) and CLT based on concentration time data obtained from lirilumab during the induction phase of treatment. In addition, Cmax and Cmin are captured at steady state for lirilumab and elotuzumab based on the concentration time data from in the maintenance phase.

The concentration data obtained in this study may be combined with data from other studies in the clinical development program to develop or refine a population PK mode. This model can be used to evaluate the effects of intrinsic and extrinsic covariates on the PK of lirilumab and elotuzumab to determine measures of individual exposure. In addition, model determined exposures can be used for exposure-response analyses.

Immunogenicity of lirilumab and elotuzumab are reported for ADA positive status (such as persistent positive, transient positive, only last sample positive, baseline positive) and ADA negative status, relative to baseline. In addition, presence of neutralizing antibodies is reported, if applicable. Effect of immunogenicity on safety are explored if there is a sufficient number of subjects with persistent positive ADA.

Biomarkers: Measures of NK, T, and Plasma cell number and phenotype are determined using flow cytometry on serial bone marrow aspirate samples and peripheral blood samples from all patients, and measures of soluble factors.

11. Analyses:

Unless otherwise specified, safety data are summarized: 1) overall, across dose escalation and cohort expansion by dose level, and 2) overall and by treatment group (A, B, or C) in cohort expansion. Efficacy data are summarized for each arm by treatment group in cohort expansion.

All subjects who receive study drug therapy are included in the analysis of safety endpoints. All recorded AEs are listed and tabulated by system organ class, preferred term, relationship to study drug, and treatment. Coding is performed according to the most current version of MedDRA. Vital signs and select clinical laboratory tests results are listed and summarized by treatment. Any significant physical examination finding and results of clinical laboratory tests are listed. Any electrocardiogram (ECG) abnormalities identified are listed.

Efficacy is listed for subjects in dose escalation and summarized by treatment group in cohort expansion. The decision to do this is made because not all efficacy endpoints are relevant for all treatment groups. Summary of escalation data is provided by dose level and treatment group for subjects in escalation who meet criteria for one of the treatment groups in cohort expansion. Relevant endpoints vary by treatment group in cohort expansion.

The landmark progression free survival rate and corresponding 95% confidence intervals are estimated at preselected timepoints using kaplan meier methodology. In addition, the Kaplan-Meier plots are generated by treatment group in cohort expansion. Objective response rate (e.g., CR+PR), the rate of conversion from minimal residual disease positive to minimal residual disease negative, and the rate of CR responses are tabulated; exact binomial 95% confidence intervals are provided using the clopper-pearson method. The distribution of the raw values and change from baseline in m-protein levels are summarized at each timepoint using descriptive statistics. Spider plots depicting changes in tumor burden over time can be generated for patients with measurable disease. In addition, plots can be produced showing m-protein levels as a function of time. Depending on the purpose of the analysis, response can reported for all treated subjects, or for response-evaluable subjects. The 1- and 2-year overall survival rates re evaluated using Kaplan-Meier methodology in subjects in the smouldering treatment group of expansion.

The pharmacodynamic effect on immune cell number and function is assessed by summary statistics and plots. In addition, the correlation of bone marrow immune cell number and function with measures of peripheral blood markers is explored graphically, or by appropriate statistical methods based on data availability, for assessing associations. The pharmacodynamic effect of treatment on markers in peripheral blood and serum proteins is assessed by summary statistics, and investigated graphically to explore patterns of change over time, and how the patterns differ among dose levels and exposure. If there is a meaningful indication in the pattern over time, further analysis (e.g, by linear mixed model) can be performed to characterize the relationship. Associations between biomarker measures from peripheral blood or bone marrow aspirate and clinical outcomes are explored graphically, and further assessed as needed by methods such as, but not limited to, logistic regression, and characterized by appropriate statistics.

SEQUENCE SUMMARY

| SEQ ID NO: | SEQUENCE |
|---|---|
| 1 | Heavy Chain Amino Acid Sequence Anti-KIR mAb (IPH2102 / lirilumab) (CDRs underlined; in addition, the P that is substituted for S in the hinge region of lirilumab is underlined.) QVQLVQSGAE VKKPGSSVKV SCKASGGTFS FYAISWVRQA PGQGLEWMGG FIPIFGAANY AQKFQGRVTI TADESTSTAY MELSSLRSDD TAVYYCARIP SGSYYYDYDM DVWGQGTTVT VSSASTKGPS VFPLAPCSRS TSESTAALGC LVKDYFPEPV TVSWNSGALT SGVHTFPAVL QSSGLYSLSS VVTVPSSSLG TKTYTCNVDH KPSNTKVDKR VESKYGPPCP PCPAPEFLGG PSVFLFPPKP KDTLMISRTP EVTCVVVDVS QEDPEVQFNW YVDGVEVHNA KTKPREEQFN STYRVVSVLT VLHQDWLNGK EYKCKVSNKG LPSSIEKTIS KAKGQPREPQ VYTLPPSQEE MTKNQVSLTC LVKGFYPSDI AVEWESNGQP ENNYKTTPPV LDSDGSFFLY SRLTVDKSRW QEGNVFSCSV MHEALHNHYT QKSLSLSLGK |
| 2 | Light Chain Amino Acid Sequence Anti-KIR mAb (IPH2102 / lirilumab) (CDRs underlined) EIVLTQSPVT LSLSPGERAT LSCRASQSVS SYLAWYQQKP GQAPRLLIYD ASNRATGIPA RFSGSGSGTD FTLTISSLEP EDFAVYYCQQ RSNWMYTFGQ GTKLEIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC |

SEQUENCE SUMMARY

| SEQ ID NO: | SEQUENCE |
|---|---|
| 3 | Heavy Chain Variable Region (VH) Amino Acid Sequence Anti-KIR mAb (IPH2102 / lirilumab) - (SEQ ID NO: 17 from WO 2006/003179)<br>QVQLVQSGAEVKKPGSSVKVSCKASGGTFSFYAISWVRQAPGQGLEWMGGFIPIFGAANYAQKFQGRVTITADESTSTAYMELSSLRSDDTAVYYCARIPSGSYYYDYDMDVWGQGTTVTVSS |
| 4 | Heavy Chain Variable Region (VH) Nucleotide Sequence Anti-KIR mAb (IPH2102 / lirilumab) - (SEQ ID NO: 18 from WO 2006/003179)<br>caggtccagc tggtgcagtc tggggctgag gtgaagaagc ctgggtcctc ggtgaaggtc tcctgcaagg cttctggagg caccttcagt ttctatgcta tcagctgggt gcgacaggcc cctggacaag gcttgagtg gatgggaggg ttcatcccta tctttggtgc agcaaactac gcacagaagt tccagggcag agtcacgatt accgcggacg aatccacgag cacagcctac atggaactga gcagcctgag atctgacgac acggccgtgt attactgtgc gagaatccct agtgggagct actactacga ctacgatatg gacgtctggg gccaagggac cacggtcacc gtctcctca |
| 5 | Light Chain Variable Region (VL) Amino Acid Sequence Anti-KIR mAb (IPH2102 / lirilumab) - (SEQ ID NO: 15 from WO 2006/003179)<br>EIVLTQSPVTLSLSPGERATLSCRASQSVSSYLAWYQQKPGQAPRLLIYDASNRATGIPARFSGSGSGTDFTLTISSLEPEDFAVYYCQQRSNWMYTFGQGTKLEIKRT |
| 6 | Light Chain Variable Region (VL) Nucleotide Sequence Anti-KIR mAb (IPH2102 / lirilumab) - (SEQ ID NO: 16 from WO 2006/003179)<br>gaaattgtgt tgacacagtc tccagtcacc ctgtctttgt ctccagggga aagagccacc ctctcctgca gggccagtca gagtgttagc agctacttag cctggtacca acagaaacct ggccaggctc ccaggctcct catctatgat gcatccaaca gggccactgg catcccagcc aggttcagt gcagtgggtc tgggacagac ttcactctca ccatcagcag cctagagcct gaagattttg cagtttatta ttgtcagcag cgtagcaact ggatgtacac ttttggccag gggaccaagc tggagatcaa acgaact |
| 7 | Heavy Chain CDR1 Amino Acid Sequence Anti-KIR mAb (IPH2102 / lirilumab) - (from FIG. 15 of WO 2006/003179) (corresponds to amino acid residues 31-35 of SEQ ID NO: 1)<br>FYAIS |
| 8 | Heavy Chain CDR2 Amino Acid Sequence Anti-KIR mAb (IPH2102 / lirilumab) - (from FIG. 15 from WO 2006/003179) (corresponds to amino acid residues 50-65 of SEQ ID NO: 1)<br>GFIPIFGAANYAQKFQ |
| 9 | Heavy Chain CDR3 Amino Acid Sequence Anti-KIR mAb (IPH2102 / lirilumab) - (from FIG. 15 from WO 2006/003179) (corresponds to amino acid residues 99-112 of SEQ ID NO: 1)<br>IPSGSYYYDYDMDV |
| 10 | Light Chain CDR1 Amino Acid Sequence Anti-KIR mAb (IPH2102 / lirilumab) - (from FIG. 15 from WO 2006/003179) (corresponds to amino acid residues 24-34 of SEQ ID NO: 3)<br>RASQSVSSYLA |
| 11 | Light Chain CDR2 Amino Acid Sequence Anti-KIR mAb (IPH2102 / lirilumab) - (from FIG. 15 from WO 2006/003179) (corresponds to amino acid residues 50-56 of SEQ ID NO: 3)<br>DASNRAT |
| 12 | Light Chain CDR3 Amino Acid Sequence Anti-KIR mAb (IPH2102 / lirilumab) - (from FIG. 15 from WO 2006/003179) (corresponds to amino acid residues 89-97 of SEQ ID NO: 3)<br>QQRSNWMYT |

SEQUENCE SUMMARY

| SEQ ID NO: | SEQUENCE |
|---|---|
| 13 | KIR2DL1 Extracellular Domain<br>(SEQ ID NO: 23 from WO 2006/003179)<br>HEGVHRKPSLLAHPGXLVKSEETVILQCWSDVMFEHFLLHREGMFNDT<br>LRLIGEHHDGVSKANFSISRMTQDLAGTYRCYGSVTHSPYQVSAPSDPLD<br>IVIIGLYEKPSLSAQXGPTVLAGENVTLSCSSRSSYDMYHLSREGEAHER<br>RLPAGPKVNGTFQADFPLGPATHGGTYRCFGSFHDSPYEWSKSSDPLLVS<br>VTGNPSNSWPSPTEPSSKTGNPRHLH |
| 14 | KIR2DL2 Extracellular Domain<br>(SEQ ID NO: 24 from WO 2006/003179)<br>HEGVHRKPSLLAHPGRLVKSEETVILQCWSDVRFEHFLLHREGKFKDTLH<br>LIGEHHDGVSKANFSIGPMMQDLAGTYRCYGSVTHSPYQLSAPSDPLDIV<br>ITGLYEKPSLSAQPGPTVLAGESVTLSCSSRSSYDMYHLSREGEAHECRF<br>SAGPKVNGTFQADFPLGPATHGGTYRCFGSFRDSPYEWSNSSDPLLVSVI<br>GNPSNSWPSPTEPSSKTGNPRHLH |
| 15 | KIR2DL3 Extracellular Domain<br>(SEQ ID NO: 25 from WO 2006/003179)<br>HEGVHRKPSLLAHPGPLVKSEETVILQCWSDVRFQHFLLHREGKFKDTLH<br>LIGEHHDGVSKANFSIGPMMQDLAGTYRCYGSVTHSPYQLSAPSDPLDIV<br>ITGLYEKPSLSAQPGPTVLAGESVTLSCSSRSSYDMYHLSREGEAHERRF<br>SAGPKVNGTFQADFPLGPATHGGTYRCFGSFRDSPYEWSNSSDPLLVSVT<br>GNPSNSWPSPTEPSSETGNPRHLH |
| 16 | KIR2DS4 Extracellular Domain<br>(SEQ ID NO: 38 from WO 2006/003179)<br>QEGVHRKPSFLALPGHLVKSEETVILQCWSDVMFEHFLLHREGKFNNTLH<br>LIGEHHDGVSKANFSIGPMMPVLAGTYRCYGSVPHSPYQLSAPSDPLDMV |
| 17 | Heavy Chain Amino Acid Sequence<br>Anti-CS1 mAb (HuLuc63; elotuzumab) |
| 18 | Light Chain Amino Acid Sequence<br>Anti-CS1 mAb (HuLuc63; elotuzumab) |
| 19 | Heavy Chain Variable Region (VH) Amino Acid Sequence<br>Anti-CS1 mAb (HuLuc63; elotuzumab)<br>EVQLVESGGGLVQPGGSLRLSCAASGFDFSRYWMSWVRQAPGKGLEWIGE<br>INPDSSTINYAPSLKDKFIISRDNAKNSLYLQMNSLRAEDTAVYYCARPD<br>GNYWYFDVWGQGT LVTVS S |
| 20 | Heavy Chain Variable Region (VH) Nucleotide Sequence<br>Anti-CS1 mAb (HuLuc63; elotuzumab) |
| 21 | Light Chain Variable Region (VL) Amino Acid Sequence<br>Anti-CS1 mAb (HuLuc63; elotuzumab)<br>DIQMTQSPSSLSASVGDRVTITCKASQDVGIAVAWYQQKPGKVPKLLIYWA<br>STRHTGVPDRFSGSGSGTDFTLTISSLQPEDVATYYCQQYSSYPYTFGQGT<br>KVEIK |
| 22 | Light Chain Variable Region (VL) Nucleotide Sequence<br>Anti-CS1 mAb (HuLuc63; elotuzumab) |
| 23 | Heavy Chain CDR1 Amino Acid Sequence<br>Anti-CS1 mAb (HuLuc63; elotuzumab)<br>RYWMS |
| 24 | Heavy Chain CDR2 Amino Acid Sequence<br>Anti-CS1 mAb (HuLuc63; elotuzumab)<br>EINPDSSTINYAPSLKD |
| 25 | Heavy Chain CDR3 Amino Acid Sequence<br>Anti-CS1 mAb (HuLuc63; elotuzumab)<br>PDGNYWYFDV |
| 26 | Light Chain CDR1 Amino Acid Sequence<br>Anti-CS1 mAb (HuLuc63; elotuzumab)<br>KASQDVGIAVA |
| 27 | Light Chain CDR2 Amino Acid Sequence<br>Anti-CS1 mAb (HuLuc63; elotuzumab)<br>WASTRHT |

SEQUENCE SUMMARY

| SEQ ID NO: | SEQUENCE |
|---|---|
| 28 | Light Chain CDR3 Amino Acid Sequence Anti-CS1 mAb (HuLuc63; elotuzumab)<br>QQYSSYPYT |
| 29 | Complete CS1 sequence (GenBank Accession No.: NM_021181.3)<br>MAGSPTCLTLIYILWQLTGSAASGPVKELVGSVGGAVTFPLKSKVKQVDSIVWT<br>FNTTPLVTIQPEGGTIIVTQNRNRERVDFPDGGYSLKLSKLKKNDSGIYYVGIY<br>SSSLQQPSTQEYVLHVYEHLSKPKVTMGLQSNKNGTCVTNLTCCMEHGEEDVIY<br>TWKALGQAANESHNGSILPISWRWGESDMTFICVARNPVSRNFSSPILARKLCE<br>GAADDPDSSMVLLCLLLVPLLLSLFVLGLFLWFLKRERQEEYIEEKKRVDICRET<br>PNICPHSGENTEYDTIPHTNRTILKEDPANTVYSTVEIPKKMENPHSLLTMPDTP<br>RLFAYENV |

What is claimed is:

1. A method of treating multiple myeloma in a human patient, the method comprising administering to the patient:
  (a) an IgG4 anti-KIR antibody comprising the CDR1, CDR2 and CDR3 domains in a heavy chain variable region having the sequence set forth in SEQ ID NO:3, and the CDR1, CDR2 and CDR3 domains in a light chain variable region having the sequence set forth in SEQ ID NO:5 at a dose of 0.1-20 mg/kg body weight, and
  (b) an IgG1 anti-CS1 antibody comprising the CDR1, CDR2 and CDR3 domains in a heavy chain variable region having the sequence set forth in SEQ ID NO:19, and the CDR1, CDR2 and CDR3 domains in a light chain variable region having the sequence set forth in SEQ ID NO:21 at a dose of 0.1-6.0 mg/kg body weight,
    wherein (A) the anti-CS1 antibody is administered weekly for a total of 8 doses over 8 weeks and the anti-KIR antibody is administered every 4 weeks for a total of 2 doses over 8 weeks during an induction phase, followed by (B) administration of the anti-CS1 antibody every 2 weeks and administration of the anti-KIR antibody every 4 weeks during a maintenance phase,
  wherein administration of the anti-KIR and anti-CSI antibodies has a synergistic effect on treatment compared to administration of either antibody alone, and
  wherein the antibodies are formulated separately or together in a pharmaceutically acceptable carrier.

2. The method of claim 1, wherein the anti-KIR antibody and anti-CS1 antibody are administered at the following doses during the induction and/or maintenance phase:
  (a) 0.1 mg/kg anti-KIR antibody and 6.0 mg/kg of anti-CS1 antibody;
  (b) 0.3 mg/kg anti-KIR antibody and 6.0 mg/kg of anti-CS1 antibody;
  (c) 1 mg/kg anti-KIR antibody and 6.0 mg/kg of anti-CS1 antibody; or
  (d) 3 mg/kg anti-KIR antibody and 6.0 mg/kg of anti-CS1 antibody.

3. The method of claim 1, wherein the anti-KIR and anti-CS1 antibodies are formulated for intravenous administration.

4. The method of claim 1, wherein the anti-KIR and anti-CS1 antibodies are administered simultaneously.

5. The method of claim 1, wherein the anti-KIR and anti-CS1 antibodies are administered separately.

6. The method of claim 1, wherein the treatment produces at least one therapeutic effect chosen from complete response, very good partial response, partial response, and stable disease.

7. The method of claim 1, wherein the anti-KIR antibody comprises (a) a heavy chain variable region CDR1 having the sequence set forth in SEQ ID NO:7;
  (b) a heavy chain variable region CDR2 having the sequence set forth in SEQ ID NO:8;
  (c) a heavy chain variable region CDR3 having the sequence set forth in SEQ ID NO:9;
  (d) a light chain variable region CDR1 having the sequence set forth in SEQ ID NO: 10;
  (e) a light chain variable region CDR2 having the sequence set forth in SEQ ID NO:11; and
  (f) a light chain variable region CDR3 having the sequence set forth in SEQ ID NO:12.

8. The method of claim 1, wherein the anti-KIR antibody comprises heavy and light chain variable regions having the sequences set forth in SEQ ID NOs:3 and 5, respectively.

9. The method of claim 1, wherein the anti-KIR antibody comprises heavy and light chains having the sequences set forth in SEQ ID NOs:1 and 2, respectively.

10. The method of claim 1, wherein the anti-CS1 antibody comprises
  (a) a heavy chain variable region CDR1 having the sequence set forth in SEQ ID NO:23;
  (b) a heavy chain variable region CDR2 having the sequence set forth in SEQ ID NO:24;
  (c) a heavy chain variable region CDR3 having the sequence set forth in SEQ ID NO:25;
  (d) a light chain variable region CDR1 having the sequence set forth in SEQ ID NO:26;
  (e) a light chain variable region CDR2 having the sequence set forth in SEQ ID NO:27; and
  (f) a light chain variable region CDR3 having the sequence set forth in SEQ ID NO:28.

11. The method of claim 1, wherein the anti-CS1 antibody comprises heavy and light chain variable regions having the sequences set forth in SEQ ID NOs:19 and 21, respectively.

12. A composition comprising:
  (a) an IgG4 anti-KIR antibody comprising the CDR1, CDR2 and CDR3 domains in a heavy chain variable region having the sequence set forth in SEQ ID NO:3, and the CDR1, CDR2 and CDR3 domains in a light chain variable region having the sequence set forth in SEQ ID NO:5 at a dose of 0.1-20 mg/kg body weight, and
  (b) an IgG1 anti-CS1 antibody comprising the CDR1, CDR2 and CDR3 domains in a heavy chain variable region having the sequence set forth in SEQ ID NO:19, and the CDR1, CDR2 and CDR3 domains in a light chain variable region having the sequence set forth in SEQ ID NO:21 at a dose of 0.1-6.0 mg/kg body weight,
    wherein the anti-KIR and anti-CS1 antibodies are formulated at doses that have a synergistic effect on treatment compared to administration of either antibody alone when (A) the anti-CS1 antibody is administered weekly for a total of 8 doses over 8 weeks and the anti-KIR antibody is administered every 4 weeks for a total of 2 doses over 8 weeks during an induction phase, followed by (B) administration of the anti-CS1 antibody every 2 weeks and administration of the anti-KIR antibody every 4 weeks during a maintenance phase.

13. A method of treating multiple myeloma in a human patient, the method comprising administering to the patient the composition of claim 12.

14. A kit for treating multiple myeloma in a human patient, the kit comprising:
(a) an IgG4 anti-KIR antibody comprising the CDR1, CDR2 and CDR3 domains in a heavy chain variable region having the sequence set forth in SEQ ID NO:3, and the CDR1, CDR2 and CDR3 domains in a light chain variable region having the sequence set forth in SEQ ID NO:5 at a dose of 0.1-20 mg/kg body weight;
(b) an IgG1 anti-CS1 antibody comprising the CDR1, CDR2 and CDR3 domains in a heavy chain variable region having the sequence set forth in SEQ ID NO:19, and the CDR1, CDR2 and CDR3 domains in a light chain variable region having the sequence set forth in SEQ ID NO:21 at a dose of 0.1-6.0 mg/kg body weight; wherein the anti-KIR and anti-CS1 antibodies are formulated at doses that have a synergistic effect on treatment compared to administration of either antibody alone when (A) the anti-CS1 antibody is administered weekly for a total of 8 doses over 8 weeks and the anti-KIR antibody is administered every 4 weeks for a total of 2 doses over 8 weeks during an induction phase, followed by (B) administration of the anti-CS1 antibody every 2 weeks and administration of the anti-KIR antibody every 4 weeks during a maintenance phase, and
(c) instructions for using the anti-KIR antibody and anti-CS1 antibody in a method of treating multiple myeloma in a human patient.

\* \* \* \* \*

SEQUENCE LISTING

<160> NUMBER OF SEQ ID NOS: 32

<210> SEQ ID NO 1
<211> LENGTH: 450
<212> TYPE: PRT
<213> ORGANISM: Homo sapiens

<400> SEQUENCE: 1

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Phe Tyr
            20                  25                  30

Ala Ile Ser Trp Val Arg Gln Ala Pro Gly Gln Gly Leu Glu Trp Met
        35                  40                  45

Gly Gly Phe Ile Pro Ile Phe Gly Ala Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Asp Asp Thr Ala Val Tyr Tyr Cys
                85                  90                  95

Ala Arg Ile Pro Ser Gly Ser Tyr Tyr Tyr Asp Tyr Asp Met Asp Val
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
    210                 215                 220

Tyr Gly Pro Pro Cys Pro Pro Cys Pro Ala Pro Glu Phe Leu Gly Gly
225                 230                 235                 240
```

```
Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Gln Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Leu
        435                 440                 445

Gly Lys
    450

<210> SEQ ID NO 2
<211> LENGTH: 214
<212> TYPE: PRT
<213> ORGANISM: Homo sapiens

<400> SEQUENCE: 2

Glu Ile Val Leu Thr Gln Ser Pro Val Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Met Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160
```

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 3
<211> LENGTH: 123
<212> TYPE: PRT
<213> ORGANISM: Homo sapiens

<400> SEQUENCE: 3

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Phe Tyr
            20                  25                  30

Ala Ile Ser Trp Val Arg Gln Ala Pro Gly Gln Gly Leu Glu Trp Met
        35                  40                  45

Gly Gly Phe Ile Pro Ile Phe Gly Ala Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Asp Thr Ala Val Tyr Tyr Cys
                85                  90                  95

Ala Arg Ile Pro Ser Gly Ser Tyr Tyr Tyr Asp Tyr Asp Met Asp Val
            100                 105                 110

Trp Gly Gln Gly Thr Thr Val Thr Val Ser Ser
            115                 120

<210> SEQ ID NO 4
<211> LENGTH: 369
<212> TYPE: DNA
<213> ORGANISM: Homo sapiens

<400> SEQUENCE: 4
caggtccagc tggtgcagtc tggggctgag gtgaagaagc ctgggtcctc ggtgaaggtc     60
tcctgcaagg cttctggagg caccttcagt ttctatgcta tcagctgggt gcgacaggcc    120
cctggacaag gccttgagtg gatgggaggg ttcatcccta tctttggtgc agcaaactac    180
gcacagaagt tccagggcag agtcacgatt accgcggacg aatccacgag cacagcctac    240
atggaactga gcagcctgag atctgacgac acggccgtgt attactgtgc gagaatccct    300
agtgggagct actactacga ctacgatatg gacgtctggg gccaagggac cacggtcacc    360
gtctcctca                                                            369

<210> SEQ ID NO 5
<211> LENGTH: 109
<212> TYPE: PRT
<213> ORGANISM: Homo sapiens

<400> SEQUENCE: 5

Glu Ile Val Leu Thr Gln Ser Pro Val Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

```
Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Met Tyr
                 85                  90                  95

Thr Phe Gly Gln Gly Thr Lys Leu Glu Ile Lys Arg Thr
            100                 105
```

<210> SEQ ID NO 6
<211> LENGTH: 327
<212> TYPE: DNA
<213> ORGANISM: Homo sapiens

<400> SEQUENCE: 6

```
gaaattgtgt tgacacagtc tccagtcacc ctgtctttgt ctccagggga aagagccacc    60
ctctcctgca gggccagtca gagtgttagc agctacttag cctggtacca acagaaacct   120
ggccaggctc ccaggctcct catctatgat gcatccaaca gggccactgg catcccagcc   180
aggttcagtg gcagtgggtc tgggacagac ttcactctca ccatcagcag cctagagcct   240
gaagattttg cagtttatta ttgtcagcag cgtagcaact ggatgtacac ttttggccag   300
gggaccaagc tggagatcaa acgaact                                       327
```

<210> SEQ ID NO 7
<211> LENGTH: 5
<212> TYPE: PRT
<213> ORGANISM: Homo sapiens

<400> SEQUENCE: 7

```
Phe Tyr Ala Ile Ser
 1               5
```

<210> SEQ ID NO 8
<211> LENGTH: 16
<212> TYPE: PRT
<213> ORGANISM: Homo sapiens

<400> SEQUENCE: 8

```
Gly Phe Ile Pro Ile Phe Gly Ala Ala Asn Tyr Ala Gln Lys Phe Gln
 1               5                  10                  15
```

<210> SEQ ID NO 9
<211> LENGTH: 14
<212> TYPE: PRT
<213> ORGANISM: Homo sapiens

<400> SEQUENCE: 9

```
Ile Pro Ser Gly Ser Tyr Tyr Tyr Asp Tyr Asp Met Asp Val
 1               5                  10
```

<210> SEQ ID NO 10
<211> LENGTH: 11
<212> TYPE: PRT
<213> ORGANISM: Homo sapiens

<400> SEQUENCE: 10

```
Arg Ala Ser Gln Ser Val Ser Ser Tyr Leu Ala
 1               5                  10
```

-continued

```
<210> SEQ ID NO 11
<211> LENGTH: 7
<212> TYPE: PRT
<213> ORGANISM: Homo sapiens

<400> SEQUENCE: 11

Asp Ala Ser Asn Arg Ala Thr
1               5

<210> SEQ ID NO 12
<211> LENGTH: 9
<212> TYPE: PRT
<213> ORGANISM: Homo sapiens

<400> SEQUENCE: 12

Gln Gln Arg Ser Asn Trp Met Tyr Thr
1               5

<210> SEQ ID NO 13
<211> LENGTH: 224
<212> TYPE: PRT
<213> ORGANISM: Homo sapiens
<220> FEATURE:
<221> NAME/KEY: VARIANT
<222> LOCATION: (16)..(16)
<223> OTHER INFORMATION: /replace="Arg"
<220> FEATURE:
<221> NAME/KEY: VARIANT
<222> LOCATION: (114)..(114)
<223> OTHER INFORMATION: /replace="Leu"
<220> FEATURE:
<221> NAME/KEY: MISC_FEATURE
<222> LOCATION: (1)..(224)
<223> OTHER INFORMATION: /note="Variant residues given in the sequence
      have no preference with respect to those in the annotations for
      variant positions"

<400> SEQUENCE: 13

His Glu Gly Val His Arg Lys Pro Ser Leu Leu Ala His Pro Gly Pro
1               5                   10                  15

Leu Val Lys Ser Glu Glu Thr Val Ile Leu Gln Cys Trp Ser Asp Val
                20                  25                  30

Met Phe Glu His Phe Leu Leu His Arg Glu Gly Met Phe Asn Asp Thr
            35                  40                  45

Leu Arg Leu Ile Gly Glu His His Asp Gly Val Ser Lys Ala Asn Phe
        50                  55                  60

Ser Ile Ser Arg Met Thr Gln Asp Leu Ala Gly Thr Tyr Arg Cys Tyr
65                  70                  75                  80

Gly Ser Val Thr His Ser Pro Tyr Gln Val Ser Ala Pro Ser Asp Pro
                85                  90                  95

Leu Asp Ile Val Ile Ile Gly Leu Tyr Glu Lys Pro Ser Leu Ser Ala
                100                 105                 110

Gln Leu Gly Pro Thr Val Leu Ala Gly Glu Asn Val Thr Leu Ser Cys
            115                 120                 125

Ser Ser Arg Ser Ser Tyr Asp Met Tyr His Leu Ser Arg Glu Gly Glu
        130                 135                 140

Ala His Glu Arg Arg Leu Pro Ala Gly Pro Lys Val Asn Gly Thr Phe
145                 150                 155                 160

Gln Ala Asp Phe Pro Leu Gly Pro Ala Thr His Gly Gly Thr Tyr Arg
                165                 170                 175

Cys Phe Gly Ser Phe His Asp Ser Pro Tyr Glu Trp Ser Lys Ser Ser
                180                 185                 190
```

```
Asp Pro Leu Leu Val Ser Val Thr Gly Asn Pro Ser Asn Ser Trp Pro
        195                 200                 205

Ser Pro Thr Glu Pro Ser Ser Lys Thr Gly Asn Pro Arg His Leu His
        210                 215                 220
```

<210> SEQ ID NO 14
<211> LENGTH: 224
<212> TYPE: PRT
<213> ORGANISM: Homo sapiens

<400> SEQUENCE: 14

```
His Glu Gly Val His Arg Lys Pro Ser Leu Leu Ala His Pro Gly Arg
1               5                   10                  15

Leu Val Lys Ser Glu Glu Thr Val Ile Leu Gln Cys Trp Ser Asp Val
            20                  25                  30

Arg Phe Glu His Phe Leu Leu His Arg Glu Gly Lys Phe Lys Asp Thr
        35                  40                  45

Leu His Leu Ile Gly Glu His His Asp Gly Val Ser Lys Ala Asn Phe
    50                  55                  60

Ser Ile Gly Pro Met Met Gln Asp Leu Ala Gly Thr Tyr Arg Cys Tyr
65                  70                  75                  80

Gly Ser Val Thr His Ser Pro Tyr Gln Leu Ser Ala Pro Ser Asp Pro
                85                  90                  95

Leu Asp Ile Val Ile Thr Gly Leu Tyr Glu Lys Pro Ser Leu Ser Ala
            100                 105                 110

Gln Pro Gly Pro Thr Val Leu Ala Gly Glu Ser Val Thr Leu Ser Cys
        115                 120                 125

Ser Ser Arg Ser Ser Tyr Asp Met Tyr His Leu Ser Arg Glu Gly Glu
    130                 135                 140

Ala His Glu Cys Arg Phe Ser Ala Gly Pro Lys Val Asn Gly Thr Phe
145                 150                 155                 160

Gln Ala Asp Phe Pro Leu Gly Pro Ala Thr His Gly Gly Thr Tyr Arg
                165                 170                 175

Cys Phe Gly Ser Phe Arg Asp Ser Pro Tyr Glu Trp Ser Asn Ser Ser
            180                 185                 190

Asp Pro Leu Leu Val Ser Val Ile Gly Asn Pro Ser Asn Ser Trp Pro
        195                 200                 205

Ser Pro Thr Glu Pro Ser Ser Lys Thr Gly Asn Pro Arg His Leu His
        210                 215                 220
```

<210> SEQ ID NO 15
<211> LENGTH: 224
<212> TYPE: PRT
<213> ORGANISM: Homo sapiens

<400> SEQUENCE: 15

```
His Glu Gly Val His Arg Lys Pro Ser Leu Leu Ala His Pro Gly Pro
1               5                   10                  15

Leu Val Lys Ser Glu Glu Thr Val Ile Leu Gln Cys Trp Ser Asp Val
            20                  25                  30

Arg Phe Gln His Phe Leu Leu His Arg Glu Gly Lys Phe Lys Asp Thr
        35                  40                  45

Leu His Leu Ile Gly Glu His His Asp Gly Val Ser Lys Ala Asn Phe
    50                  55                  60
```

Ser Ile Gly Pro Met Met Gln Asp Leu Ala Gly Thr Tyr Arg Cys Tyr
65                  70                  75                  80

Gly Ser Val Thr His Ser Pro Tyr Gln Leu Ser Ala Pro Ser Asp Pro
                85                  90                  95

Leu Asp Ile Val Ile Thr Gly Leu Tyr Glu Lys Pro Ser Leu Ser Ala
            100                 105                 110

Gln Pro Gly Pro Thr Val Leu Ala Gly Glu Ser Val Thr Leu Ser Cys
            115                 120                 125

Ser Ser Arg Ser Ser Tyr Asp Met Tyr His Leu Ser Arg Glu Gly Glu
            130                 135                 140

Ala His Glu Arg Arg Phe Ser Ala Gly Pro Lys Val Asn Gly Thr Phe
145                 150                 155                 160

Gln Ala Asp Phe Pro Leu Gly Pro Ala Thr His Gly Gly Thr Tyr Arg
                165                 170                 175

Cys Phe Gly Ser Phe Arg Asp Ser Pro Tyr Glu Trp Ser Asn Ser Ser
                180                 185                 190

Asp Pro Leu Leu Val Ser Val Thr Gly Asn Pro Ser Asn Ser Trp Pro
            195                 200                 205

Ser Pro Thr Glu Pro Ser Ser Glu Thr Gly Asn Pro Arg His Leu His
210                 215                 220

<210> SEQ ID NO 16
<211> LENGTH: 100
<212> TYPE: PRT
<213> ORGANISM: Homo sapiens

<400> SEQUENCE: 16

Gln Glu Gly Val His Arg Lys Pro Ser Phe Leu Ala Leu Pro Gly His
1                   5                   10                  15

Leu Val Lys Ser Glu Glu Thr Val Ile Leu Gln Cys Trp Ser Asp Val
            20                  25                  30

Met Phe Glu His Phe Leu Leu His Arg Glu Gly Lys Phe Asn Asn Thr
        35                  40                  45

Leu His Leu Ile Gly Glu His His Asp Gly Val Ser Lys Ala Asn Phe
    50                  55                  60

Ser Ile Gly Pro Met Met Pro Val Leu Ala Gly Thr Tyr Arg Cys Tyr
65                  70                  75                  80

Gly Ser Val Pro His Ser Pro Tyr Gln Leu Ser Ala Pro Ser Asp Pro
                85                  90                  95

Leu Asp Met Val
            100

<210> SEQ ID NO 17

<400> SEQUENCE: 17

000

<210> SEQ ID NO 18

<400> SEQUENCE: 18

000

<210> SEQ ID NO 19
<211> LENGTH: 119
<212> TYPE: PRT
<213> ORGANISM: Homo sapiens

<400> SEQUENCE: 19

Glu Val Gln Leu Val Glu Ser Gly Gly Leu Val Gln Pro Gly Gly
1               5                   10                  15

Ser Leu Arg Leu Ser Cys Ala Ala Ser Gly Phe Asp Phe Ser Arg Tyr
            20                  25                  30

Trp Met Ser Trp Val Arg Gln Ala Pro Gly Lys Gly Leu Glu Trp Ile
        35                  40                  45

Gly Glu Ile Asn Pro Asp Ser Ser Thr Ile Asn Tyr Ala Pro Ser Leu
    50                  55                  60

Lys Asp Lys Phe Ile Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Pro Asp Gly Asn Tyr Trp Tyr Phe Asp Val Trp Gly Gln Gly
            100                 105                 110

Thr Leu Val Thr Val Ser Ser
        115

<210> SEQ ID NO 20

<400> SEQUENCE: 20

000

<210> SEQ ID NO 21
<211> LENGTH: 107
<212> TYPE: PRT
<213> ORGANISM: Homo sapiens

<400> SEQUENCE: 21

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Gly Ile Ala
            20                  25                  30

Val Ala Trp Tyr Gln Gln Lys Pro Gly Lys Val Pro Lys Leu Leu Ile
        35                  40                  45

Tyr Trp Ala Ser Thr Arg His Thr Gly Val Pro Asp Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Gln Tyr Ser Ser Tyr Pro Tyr
                85                  90                  95

Thr Phe Gly Gln Gly Thr Lys Val Glu Ile Lys
            100                 105

<210> SEQ ID NO 22

<400> SEQUENCE: 22

000

<210> SEQ ID NO 23
<211> LENGTH: 5
<212> TYPE: PRT
<213> ORGANISM: Homo sapiens

<400> SEQUENCE: 23

Arg Tyr Trp Met Ser
1               5

<210> SEQ ID NO 24
<211> LENGTH: 17
<212> TYPE: PRT
<213> ORGANISM: Homo sapiens

<400> SEQUENCE: 24

Glu Ile Asn Pro Asp Ser Ser Thr Ile Asn Tyr Ala Pro Ser Leu Lys
1               5                   10                  15
Asp

<210> SEQ ID NO 25
<211> LENGTH: 10
<212> TYPE: PRT
<213> ORGANISM: Homo sapiens

<400> SEQUENCE: 25

Pro Asp Gly Asn Tyr Trp Tyr Phe Asp Val
1               5                   10

<210> SEQ ID NO 26
<211> LENGTH: 11
<212> TYPE: PRT
<213> ORGANISM: Homo sapiens

<400> SEQUENCE: 26

Lys Ala Ser Gln Asp Val Gly Ile Ala Val Ala
1               5                   10

<210> SEQ ID NO 27
<211> LENGTH: 7
<212> TYPE: PRT
<213> ORGANISM: Homo sapiens

<400> SEQUENCE: 27

Trp Ala Ser Thr Arg His Thr
1               5

<210> SEQ ID NO 28
<211> LENGTH: 9
<212> TYPE: PRT
<213> ORGANISM: Homo sapiens

<400> SEQUENCE: 28

Gln Gln Tyr Ser Ser Tyr Pro Tyr Thr
1               5

<210> SEQ ID NO 29
<211> LENGTH: 334
<212> TYPE: PRT
<213> ORGANISM: Homo sapiens

<400> SEQUENCE: 29

Met Ala Gly Ser Pro Thr Cys Leu Thr Leu Ile Tyr Ile Leu Trp Gln
1               5                   10                  15

Leu Thr Gly Ser Ala Ala Ser Gly Pro Val Lys Glu Leu Val Gly Ser
                20                  25                  30

Val Gly Gly Ala Val Thr Phe Pro Leu Lys Ser Lys Val Lys Gln Val
            35                  40                  45

Asp Ser Ile Val Trp Thr Phe Asn Thr Thr Pro Leu Val Thr Ile Gln
        50                  55                  60

```
Pro Glu Gly Gly Thr Ile Val Thr Gln Asn Arg Asn Arg Glu Arg
65                  70                  75                  80

Val Asp Phe Pro Asp Gly Gly Tyr Ser Leu Lys Leu Ser Lys Leu Lys
                85                  90                  95

Lys Asn Asp Ser Gly Ile Tyr Tyr Val Gly Ile Tyr Ser Ser Leu
            100                 105                 110

Gln Gln Pro Ser Thr Gln Glu Tyr Val Leu His Val Tyr Glu His Leu
            115                 120                 125

Ser Lys Pro Lys Val Thr Met Gly Leu Gln Ser Asn Lys Asn Gly Thr
    130                 135                 140

Cys Val Thr Asn Leu Thr Cys Cys Met Glu His Gly Glu Glu Asp Val
145                 150                 155                 160

Ile Tyr Thr Trp Lys Ala Leu Gly Gln Ala Ala Asn Glu Ser His Asn
                165                 170                 175

Gly Ser Ile Leu Pro Ile Ser Trp Arg Trp Gly Glu Ser Asp Met Thr
            180                 185                 190

Phe Ile Cys Val Ala Arg Asn Pro Val Ser Arg Asn Phe Ser Ser Pro
        195                 200                 205

Ile Leu Ala Arg Lys Leu Cys Glu Gly Ala Ala Asp Asp Pro Asp Ser
    210                 215                 220

Ser Met Val Leu Leu Cys Leu Leu Val Pro Leu Leu Leu Ser Leu
225                 230                 235                 240

Phe Val Leu Gly Leu Phe Leu Trp Phe Leu Lys Arg Glu Arg Gln Glu
                245                 250                 255

Glu Tyr Ile Glu Glu Lys Lys Arg Val Asp Ile Cys Arg Glu Thr Pro
            260                 265                 270

Asn Ile Cys Pro His Ser Gly Glu Asn Thr Glu Tyr Asp Thr Ile Pro
            275                 280                 285

His Thr Asn Arg Thr Ile Leu Lys Glu Asp Pro Ala Asn Thr Val Tyr
    290                 295                 300

Ser Thr Val Glu Ile Pro Lys Lys Met Glu Asn Pro His Ser Leu Leu
305                 310                 315                 320

Thr Met Pro Asp Thr Pro Arg Leu Phe Ala Tyr Glu Asn Val
                325                 330
```

<210> SEQ ID NO 30
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 30
tattgggacc gggagacaca                                            20

<210> SEQ ID NO 31
<211> LENGTH: 16
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 31
cgcaggttcc gcaggc                                                16

```
<210> SEQ ID NO 32
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 32
gcgcagtttc cgcaggt                                                    17
```